(12) United States Patent
Noyes et al.

(10) Patent No.: US 12,233,356 B2
(45) Date of Patent: Feb. 25, 2025

(54) PROCESS FOR PREPARING EXTRACELLULAR VESICLES

(71) Applicant: LONZA SALES AG, Basel (CH)

(72) Inventors: Aaron Noyes, Melrose, MA (US); Michael Doherty, Somerville, MA (US); Kimberly Ellis, Somerville, MA (US); Raymond Bourdeau, Watertown, MA (US); Kayla Desanty, Bedford, MA (US)

(73) Assignee: LONZA SALES AG, Basel (CH)

( * ) Notice: Subject to any disclaimer, the term of this patent is extended or adjusted under 35 U.S.C. 154(b) by 425 days.

(21) Appl. No.: 17/593,613

(22) PCT Filed: Mar. 20, 2020

(86) PCT No.: PCT/US2020/024038
§ 371 (c)(1),
(2) Date: Sep. 21, 2021

(87) PCT Pub. No.: WO2020/191369
PCT Pub. Date: Sep. 24, 2020

(65) Prior Publication Data
US 2022/0387906 A1 Dec. 8, 2022

Related U.S. Application Data

(60) Provisional application No. 62/984,141, filed on Mar. 2, 2020, provisional application No. 62/946,895, filed
(Continued)

(51) Int. Cl.
B01D 15/36 (2006.01)
A61K 39/00 (2006.01)
C12M 1/00 (2006.01)

(52) U.S. Cl.
CPC ............ *B01D 15/362* (2013.01); *A61K 39/00* (2013.01); *B01D 15/363* (2013.01); *C12M 29/10* (2013.01)

(58) Field of Classification Search
None
See application file for complete search history.

(56) References Cited

U.S. PATENT DOCUMENTS

2008/0177048 A1 7/2008 Gagnon
2015/0353920 A1 12/2015 Enderle et al.

FOREIGN PATENT DOCUMENTS

CN 107858324 A 3/2018
WO 2012/087241 A1 6/2012
(Continued)

OTHER PUBLICATIONS

Zhang, et al., Biochem Biophys Res Commun. Feb. 8, 2008; 366(2): 579-584 (Year: 2008).*
(Continued)

Primary Examiner — Krishnan S Menon
(74) Attorney, Agent, or Firm — MEDLER FERRO WOODHOUSE & MILLS PLLC

(57) ABSTRACT

The present disclosure relates to multistep chromatographic methods for preparing extracellular vesicles (EVs). The methods were demonstrated to be effective in preparing highquality EVs in a large scale. The methods enable preparation of EVs for therapeutic and diagnostic applications, and isolation and/or sub-fractionation of EVs with desired properties for specific use.

10 Claims, 18 Drawing Sheets

Specification includes a Sequence Listing.

Related U.S. Application Data on Dec. 11, 2019, provisional application No. 62/903,524, filed on Sep. 20, 2019, provisional application No. 62/835,436, filed on Apr. 17, 2019, provisional application No. 62/822,013, filed on Mar. 21, 2019.

(56) References Cited

FOREIGN PATENT DOCUMENTS

| | | |
|---|---|---|
| WO | 2016/176500 A1 | 11/2016 |
| WO | 2017/197399 A1 | 11/2017 |
| WO | 2020/027185 A1 | 2/2020 |

OTHER PUBLICATIONS

Choudhary et al., "[3] Ion-Exchange Chromatography," Methods in Enzymology. vol. 2711 (Year: 1996).*
International Search Report in PCT/US2020/024038, ISA EPO, dated Oct. 8, 2020.
Kim et al., "Chromatographically isolated CD63+CD81+ extracellular vesicles from mesenchymal stromal cells rescue cognitive impairments after TBI," PNAS 113(1): 170-175 (2016).
Tengattini, "Chromatographic Approaches for Purification and Analytical Characterization of Extracellular Vesicles: Recent Advancements," Chromatographia 82(1): 415-424 (2018).
United States Patent and Trademark Office, Non-Final Office Action in U.S. Pat. No. 18,050,011, dated Mar. 29, 2024.
United States Patent and Trademark Office, Final Office Action in U.S. Appl. No. 18/050,011, dated Oct. 10, 2025.

* cited by examiner

|  | 50 LA | 50 LB | 50 LC | 50 LD |
|---|---|---|---|---|
| Benzonase/Filtration | 110% | 81% | NA | NA |
| UFDF1 | 71% | 106% | 85% | 67% |
| UFDF1 Pool Filtration |  | 85% | 68% | 86% |
| CEX Chromatography | 50% | 75% | 75% | 86% |
| CEX Pool Filtration | NA | 100% | 93% | 101% |
| AEX Chromatography | 37% | 34% | 49% | 24% |
| AEX Pool Filtration | NA | 83% | 102% | 119% |
| MMC Chromatography | 92% | 83% | 88% | 70% |
| MMC Pool Filtration | NA | 113% | 99% | 91% |
| UFDF2 | 30% | 64% | 113% | 75% |
| Final Filtration | 98% | 91% | 85% | 91% |
| Overall Process Yield | 4% | 8% | 15% | 6% |

Process development improved yield across batches →

FIG. 3

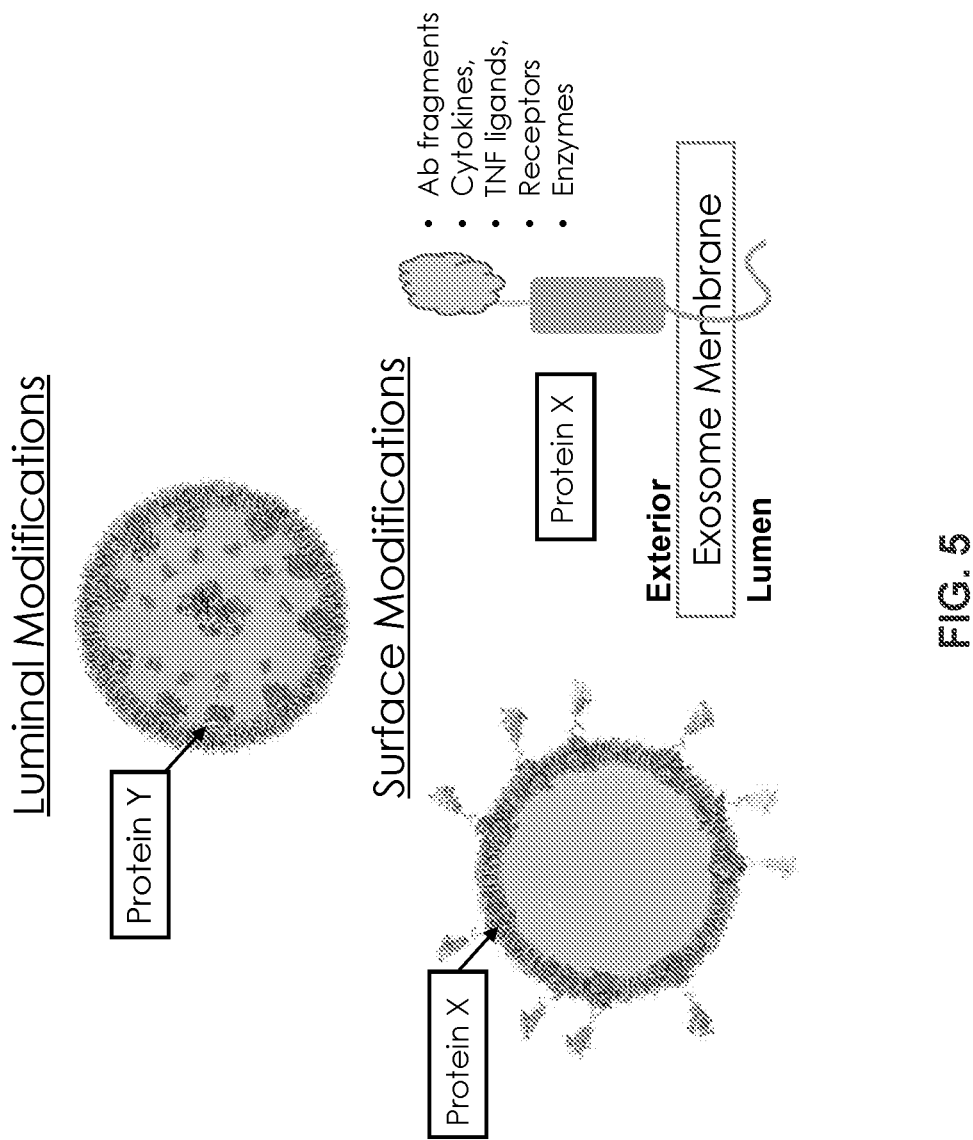

SEQUENCE LISTING

```
<160> NUMBER OF SEQ ID NOS: 168

<210> SEQ ID NO 1
<211> LENGTH: 879
<212> TYPE: PRT
<213> ORGANISM: Homo sapiens

<400> SEQUENCE: 1

Met Gly Arg Leu Ala Ser Arg Pro Leu Leu Leu Ala Leu Leu Ser Leu
 1               5                   10                  15

Ala Leu Cys Arg Gly Arg Val Val Arg Val Pro Thr Ala Thr Leu Val
            20                  25                  30
```

-continued

Arg Val Val Gly Thr Glu Leu Val Ile Pro Cys Asn Val Ser Asp Tyr
         35                  40                  45

Asp Gly Pro Ser Glu Gln Asn Phe Asp Trp Ser Phe Ser Ser Leu Gly
 50                  55                  60

Ser Ser Phe Val Glu Leu Ala Ser Thr Trp Glu Val Gly Phe Pro Ala
 65                  70                  75                  80

Gln Leu Tyr Gln Glu Arg Leu Gln Arg Gly Glu Ile Leu Leu Arg Arg
                 85                  90                  95

Thr Ala Asn Asp Ala Val Glu Leu His Ile Lys Asn Val Gln Pro Ser
             100                 105                 110

Asp Gln Gly His Tyr Lys Cys Ser Thr Pro Ser Thr Asp Ala Thr Val
         115                 120                 125

Gln Gly Asn Tyr Glu Asp Thr Val Gln Val Lys Val Leu Ala Asp Ser
 130                 135                 140

Leu His Val Gly Pro Ser Ala Arg Pro Pro Ser Leu Ser Leu Arg
145                 150                 155                 160

Glu Gly Glu Pro Phe Glu Leu Arg Cys Thr Ala Ala Ser Ala Ser Pro
                 165                 170                 175

Leu His Thr His Leu Ala Leu Leu Trp Glu Val His Arg Gly Pro Ala
             180                 185                 190

Arg Arg Ser Val Leu Ala Leu Thr His Glu Gly Arg Phe His Pro Gly
         195                 200                 205

Leu Gly Tyr Glu Gln Arg Tyr His Ser Gly Asp Val Arg Leu Asp Thr
 210                 215                 220

Val Gly Ser Asp Ala Tyr Arg Leu Ser Val Ser Arg Ala Leu Ser Ala
225                 230                 235                 240

Asp Gln Gly Ser Tyr Arg Cys Ile Val Ser Glu Trp Ile Ala Glu Gln
                 245                 250                 255

Gly Asn Trp Gln Glu Ile Gln Glu Lys Ala Val Glu Val Ala Thr Val
             260                 265                 270

Val Ile Gln Pro Ser Val Leu Arg Ala Ala Val Pro Lys Asn Val Ser
         275                 280                 285

Val Ala Glu Gly Lys Glu Leu Asp Leu Thr Cys Asn Ile Thr Thr Asp
 290                 295                 300

Arg Ala Asp Asp Val Arg Pro Glu Val Thr Trp Ser Phe Ser Arg Met
305                 310                 315                 320

Pro Asp Ser Thr Leu Pro Gly Ser Arg Val Leu Ala Arg Leu Asp Arg
                 325                 330                 335

Asp Ser Leu Val His Ser Ser Pro His Val Ala Leu Ser His Val Asp
             340                 345                 350

Ala Arg Ser Tyr His Leu Leu Val Arg Asp Val Ser Lys Glu Asn Ser
         355                 360                 365

Gly Tyr Tyr Tyr Cys His Val Ser Leu Trp Ala Pro Gly His Asn Arg
 370                 375                 380

Ser Trp His Lys Val Ala Glu Ala Val Ser Ser Pro Ala Gly Val Gly
385                 390                 395                 400

Val Thr Trp Leu Glu Pro Asp Tyr Gln Val Tyr Leu Asn Ala Ser Lys
                 405                 410                 415

Val Pro Gly Phe Ala Asp Pro Thr Glu Leu Ala Cys Arg Val Val
             420                 425                 430

Asp Thr Lys Ser Gly Glu Ala Asn Val Arg Phe Thr Val Ser Trp Tyr
         435                 440                 445

Tyr Arg Met Asn Arg Arg Ser Asp Asn Val Val Thr Ser Glu Leu Leu

```
            450                 455                 460
Ala Val Met Asp Gly Asp Trp Thr Leu Lys Tyr Gly Glu Arg Ser Lys
465                 470                 475                 480

Gln Arg Ala Gln Asp Gly Asp Phe Ile Phe Ser Lys Glu His Thr Asp
                485                 490                 495

Thr Phe Asn Phe Arg Ile Gln Arg Thr Thr Glu Glu Asp Arg Gly Asn
                500                 505                 510

Tyr Tyr Cys Val Val Ser Ala Trp Thr Lys Gln Arg Asn Asn Ser Trp
            515                 520                 525

Val Lys Ser Lys Asp Val Phe Ser Lys Pro Val Asn Ile Phe Trp Ala
        530                 535                 540

Leu Glu Asp Ser Val Leu Val Lys Ala Arg Gln Pro Lys Pro Phe
545                 550                 555                 560

Phe Ala Ala Gly Asn Thr Phe Glu Met Thr Cys Lys Val Ser Ser Lys
                565                 570                 575

Asn Ile Lys Ser Pro Arg Tyr Ser Val Leu Ile Met Ala Glu Lys Pro
            580                 585                 590

Val Gly Asp Leu Ser Ser Pro Asn Glu Thr Lys Tyr Ile Ile Ser Leu
        595                 600                 605

Asp Gln Asp Ser Val Val Lys Leu Glu Asn Trp Thr Asp Ala Ser Arg
            610                 615                 620

Val Asp Gly Val Val Leu Glu Lys Val Gln Glu Asp Glu Phe Arg Tyr
625                 630                 635                 640

Arg Met Tyr Gln Thr Gln Val Ser Asp Ala Gly Leu Tyr Arg Cys Met
                645                 650                 655

Val Thr Ala Trp Ser Pro Val Arg Gly Ser Leu Trp Arg Glu Ala Ala
                660                 665                 670

Thr Ser Leu Ser Asn Pro Ile Glu Ile Asp Phe Gln Thr Ser Gly Pro
            675                 680                 685

Ile Phe Asn Ala Ser Val His Ser Asp Thr Pro Ser Val Ile Arg Gly
        690                 695                 700

Asp Leu Ile Lys Leu Phe Cys Ile Ile Thr Val Glu Gly Ala Ala Leu
705                 710                 715                 720

Asp Pro Asp Asp Met Ala Phe Asp Val Ser Trp Phe Ala Val His Ser
                725                 730                 735

Phe Gly Leu Asp Lys Ala Pro Val Leu Leu Ser Ser Leu Asp Arg Lys
            740                 745                 750

Gly Ile Val Thr Thr Ser Arg Arg Asp Trp Lys Ser Asp Leu Ser Leu
        755                 760                 765

Glu Arg Val Ser Val Leu Glu Phe Leu Leu Gln Val His Gly Ser Glu
770                 775                 780

Asp Gln Asp Phe Gly Asn Tyr Tyr Cys Ser Val Thr Pro Trp Val Lys
785                 790                 795                 800

Ser Pro Thr Gly Ser Trp Gln Lys Glu Ala Glu Ile His Ser Lys Pro
                805                 810                 815

Val Phe Ile Thr Val Lys Met Asp Val Leu Asn Ala Phe Lys Tyr Pro
            820                 825                 830

Leu Leu Ile Gly Val Gly Leu Ser Thr Val Ile Gly Leu Leu Ser Cys
        835                 840                 845

Leu Ile Gly Tyr Cys Ser Ser His Trp Cys Lys Lys Glu Val Gln
    850                 855                 860

Glu Thr Arg Arg Glu Arg Arg Arg Leu Met Ser Met Glu Met Asp
865                 870                 875
```

```
<210> SEQ ID NO 2
<211> LENGTH: 192
<212> TYPE: PRT
<213> ORGANISM: Homo sapiens

<400> SEQUENCE: 2

Gly Pro Ile Phe Asn Ala Ser Val His Ser Asp Thr Pro Ser Val Ile
1               5                   10                  15

Arg Gly Asp Leu Ile Lys Leu Phe Cys Ile Ile Thr Val Glu Gly Ala
            20                  25                  30

Ala Leu Asp Pro Asp Asp Met Ala Phe Asp Val Ser Trp Phe Ala Val
        35                  40                  45

His Ser Phe Gly Leu Asp Lys Ala Pro Val Leu Leu Ser Ser Leu Asp
    50                  55                  60

Arg Lys Gly Ile Val Thr Thr Ser Arg Arg Asp Trp Lys Ser Asp Leu
65                  70                  75                  80

Ser Leu Glu Arg Val Ser Val Leu Glu Phe Leu Leu Gln Val His Gly
                85                  90                  95

Ser Glu Asp Gln Asp Phe Gly Asn Tyr Tyr Cys Ser Val Thr Pro Trp
            100                 105                 110

Val Lys Ser Pro Thr Gly Ser Trp Gln Lys Glu Ala Glu Ile His Ser
        115                 120                 125

Lys Pro Val Phe Ile Thr Val Lys Met Asp Val Leu Asn Ala Phe Lys
    130                 135                 140

Tyr Pro Leu Leu Ile Gly Val Gly Leu Ser Thr Val Ile Gly Leu Leu
145                 150                 155                 160

Ser Cys Leu Ile Gly Tyr Cys Ser Ser His Trp Cys Cys Lys Lys Glu
                165                 170                 175

Val Gln Glu Thr Arg Arg Glu Arg Arg Arg Leu Met Ser Met Glu Met
            180                 185                 190

<210> SEQ ID NO 3
<211> LENGTH: 227
<212> TYPE: PRT
<213> ORGANISM: Homo sapiens

<400> SEQUENCE: 3

Met Gly Gly Lys Leu Ser Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Gly Glu Lys Asp Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala Ala
        115                 120                 125

Pro Ala Glu Ser Ala Ala Pro Ala Ala Gly Glu Glu Pro Ser Lys Glu
    130                 135                 140
```

```
Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
            195                 200                 205

Pro Lys Pro Val Glu Ala Pro Ala Ala Asn Ser Asp Gln Thr Val Thr
        210                 215                 220

Val Lys Glu
225

<210> SEQ ID NO 4
<211> LENGTH: 9
<212> TYPE: PRT
<213> ORGANISM: Artificial Sequence
<220> FEATURE:
<223> OTHER INFORMATION: Scaffold Y Effector Domain
<220> FEATURE:
<221> NAME/KEY: MISC_FEATURE
<222> LOCATION: (3)..(3)
<223> OTHER INFORMATION: Xaa is Alanine, or any other amino acid

<400> SEQUENCE: 4

Met Gly Xaa Lys Leu Ser Lys Lys Lys
1               5

<210> SEQ ID NO 5
<211> LENGTH: 4
<212> TYPE: PRT
<213> ORGANISM: artificial sequence
<220> FEATURE:
<223> OTHER INFORMATION: Scaffold Y Effector Domain

<400> SEQUENCE: 5

Lys Lys Lys Lys
1

<210> SEQ ID NO 6
<211> LENGTH: 5
<212> TYPE: PRT
<213> ORGANISM: artificial sequence
<220> FEATURE:
<223> OTHER INFORMATION: Scaffold Y Effector Domain

<400> SEQUENCE: 6

Lys Lys Lys Lys Lys
1               5

<210> SEQ ID NO 7
<211> LENGTH: 4
<212> TYPE: PRT
<213> ORGANISM: artificial sequence
<220> FEATURE:
<223> OTHER INFORMATION: Scaffold Y Effector Domain

<400> SEQUENCE: 7

Arg Arg Arg Arg
1

<210> SEQ ID NO 8
<211> LENGTH: 5
<212> TYPE: PRT
```

```
<213> ORGANISM: artificial sequence
<220> FEATURE:
<223> OTHER INFORMATION: Scaffold Y Effector Domain

<400> SEQUENCE: 8

Arg Arg Arg Arg Arg
1               5

<210> SEQ ID NO 9
<211> LENGTH: 4
<212> TYPE: PRT
<213> ORGANISM: artificial sequence
<220> FEATURE:
<223> OTHER INFORMATION: Scaffold Y Effector Domain
<220> FEATURE:
<221> NAME/KEY: Misc_Feature
<222> LOCATION: (1)..(1)
<223> OTHER INFORMATION: Xaa is Lys or Arg
<220> FEATURE:
<221> NAME/KEY: Misc_Feature
<222> LOCATION: (2)..(2)
<223> OTHER INFORMATION: Xaa is Lys or Arg
<220> FEATURE:
<221> NAME/KEY: Misc_Feature
<222> LOCATION: (3)..(3)
<223> OTHER INFORMATION: Xaa is Lys or Arg
<220> FEATURE:
<221> NAME/KEY: Misc_Feature
<222> LOCATION: (4)..(4)
<223> OTHER INFORMATION: Xaa is Lys or Arg

<400> SEQUENCE: 9

Xaa Xaa Xaa Xaa
1

<210> SEQ ID NO 10
<211> LENGTH: 5
<212> TYPE: PRT
<213> ORGANISM: artificial sequence
<220> FEATURE:
<223> OTHER INFORMATION: Scaffold Y Effector Domain
<220> FEATURE:
<221> NAME/KEY: Misc_Feature
<222> LOCATION: (1)..(1)
<223> OTHER INFORMATION: Xaa is Lys or Arg
<220> FEATURE:
<221> NAME/KEY: Misc_Feature
<222> LOCATION: (2)..(2)
<223> OTHER INFORMATION: Xaa is Lys or Arg
<220> FEATURE:
<221> NAME/KEY: Misc_Feature
<222> LOCATION: (3)..(3)
<223> OTHER INFORMATION: Xaa is Lys or Arg
<220> FEATURE:
<221> NAME/KEY: Misc_Feature
<222> LOCATION: (4)..(4)
<223> OTHER INFORMATION: Xaa is Lys or Arg
<220> FEATURE:
<221> NAME/KEY: Misc_Feature
<222> LOCATION: (5)..(5)
<223> OTHER INFORMATION: Xaa is Lys or Arg

<400> SEQUENCE: 10

Xaa Xaa Xaa Xaa Xaa
1               5

<210> SEQ ID NO 11
<211> LENGTH: 7
<212> TYPE: PRT
<213> ORGANISM: artificial sequence
<220> FEATURE:
<223> OTHER INFORMATION: Scaffold Y Fragment
```

```
<400> SEQUENCE: 11

Gly Gly Lys Leu Ser Lys Lys
1               5

<210> SEQ ID NO 12
<211> LENGTH: 7
<212> TYPE: PRT
<213> ORGANISM: artificial sequence
<220> FEATURE:
<223> OTHER INFORMATION: Scaffold Y Fragment

<400> SEQUENCE: 12

Gly Ala Lys Leu Ser Lys Lys
1               5

<210> SEQ ID NO 13
<211> LENGTH: 7
<212> TYPE: PRT
<213> ORGANISM: artificial sequence
<220> FEATURE:
<223> OTHER INFORMATION: Scaffold Y Fragment

<400> SEQUENCE: 13

Gly Gly Lys Gln Ser Lys Lys
1               5

<210> SEQ ID NO 14
<211> LENGTH: 7
<212> TYPE: PRT
<213> ORGANISM: artificial sequence
<220> FEATURE:
<223> OTHER INFORMATION: Scaffold Y Fragment

<400> SEQUENCE: 14

Gly Gly Lys Leu Ala Lys Lys
1               5

<210> SEQ ID NO 15
<211> LENGTH: 6
<212> TYPE: PRT
<213> ORGANISM: artificial sequence
<220> FEATURE:
<223> OTHER INFORMATION: Scaffold Y N-Terminal Domain

<400> SEQUENCE: 15

Gly Gly Lys Leu Ser Lys
1               5

<210> SEQ ID NO 16
<211> LENGTH: 6
<212> TYPE: PRT
<213> ORGANISM: artificial sequence
<220> FEATURE:
<223> OTHER INFORMATION: Scaffold Y N-Terminal Domain

<400> SEQUENCE: 16

Gly Ala Lys Leu Ser Lys
1               5

<210> SEQ ID NO 17
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 17
```

```
Gly Gly Lys Gln Ser Lys
1               5

<210> SEQ ID NO 18
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 18

Gly Gly Lys Leu Ala Lys
1               5

<210> SEQ ID NO 19
<211> LENGTH: 4
<212> TYPE: PRT
<213> ORGANISM: artificial sequence
<220> FEATURE:
<223> OTHER INFORMATION: Scaffold Y Effector Domain

<400> SEQUENCE: 19

Lys Lys Lys Gly
1

<210> SEQ ID NO 20
<211> LENGTH: 5
<212> TYPE: PRT
<213> ORGANISM: artificial sequence
<220> FEATURE:
<223> OTHER INFORMATION: Scaffold Y Effector Domain

<400> SEQUENCE: 20

Lys Lys Lys Gly Tyr
1               5

<210> SEQ ID NO 21
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 21

Lys Lys Lys Gly Tyr Asn
1               5

<210> SEQ ID NO 22
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 22

Lys Lys Lys Gly Tyr Asn Val
1               5

<210> SEQ ID NO 23
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 23
```

```
Lys Lys Lys Gly Tyr Asn Val Asn
1               5

<210> SEQ ID NO 24
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 24

Lys Lys Lys Gly Tyr Ser
1               5

<210> SEQ ID NO 25
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 25

Lys Lys Lys Gly Tyr Gly
1               5

<210> SEQ ID NO 26
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 26

Lys Lys Lys Gly Tyr Gly Gly
1               5

<210> SEQ ID NO 27
<211> LENGTH: 5
<212> TYPE: PRT
<213> ORGANISM: artificial sequence
<220> FEATURE:
<223> OTHER INFORMATION: Scaffold Y Effector Domain

<400> SEQUENCE: 27

Lys Lys Lys Gly Ser
1               5

<210> SEQ ID NO 28
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 28

Lys Lys Lys Gly Ser Gly
1               5

<210> SEQ ID NO 29
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 29

Lys Lys Lys Gly Ser Gly Ser
```

```
1               5
```

<210> SEQ ID NO 30
<211> LENGTH: 4
<212> TYPE: PRT
<213> ORGANISM: artificial sequence
<220> FEATURE:
<223> OTHER INFORMATION: Scaffold Y Effector Domain

<400> SEQUENCE: 30

```
Lys Lys Lys Ser
1
```

<210> SEQ ID NO 31
<211> LENGTH: 5
<212> TYPE: PRT
<213> ORGANISM: artificial sequence
<220> FEATURE:
<223> OTHER INFORMATION: Scaffold Y Effector Domain

<400> SEQUENCE: 31

```
Lys Lys Lys Ser Gly
1               5
```

<210> SEQ ID NO 32
<211> LENGTH: 6
<212> TYPE: PRT
<213> ORGANISM: artificial sequence
<220> FEATURE:
<223> OTHER INFORMATION: Scaffold Y Effector Domain

<400> SEQUENCE: 32

```
Lys Lys Lys Ser Gly Gly
1               5
```

<210> SEQ ID NO 33
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 33

```
Lys Lys Lys Ser Gly Gly Ser
1               5
```

<210> SEQ ID NO 34
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 34

```
Lys Lys Lys Ser Gly Gly Ser Gly
1               5
```

<210> SEQ ID NO 35
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 35

```
Lys Lys Ser Gly Gly Ser Gly Gly
1               5
```

<210> SEQ ID NO 36
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 36

Lys Lys Lys Ser Gly Gly Ser Gly Gly Ser
1               5                   10

<210> SEQ ID NO 37
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 37

Lys Arg Phe Ser Phe Lys Lys Ser
1               5

<210> SEQ ID NO 38
<211> LENGTH: 8
<212> TYPE: PRT
<213> ORGANISM: artificial sequence
<220> FEATURE:
<223> OTHER INFORMATION: Scaffold Y Fragment

<400> SEQUENCE: 38

Gly Gly Lys Leu Ser Lys Lys Lys
1               5

<210> SEQ ID NO 39
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 39

Gly Gly Lys Leu Ser Lys Lys Ser
1               5

<210> SEQ ID NO 40
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 40

Gly Ala Lys Leu Ser Lys Lys Lys
1               5

<210> SEQ ID NO 41
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 41

Gly Ala Lys Leu Ser Lys Lys Ser
1               5

```
<210> SEQ ID NO 42
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 42

Gly Gly Lys Gln Ser Lys Lys Lys
1               5

<210> SEQ ID NO 43
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 43

Gly Gly Lys Gln Ser Lys Lys Ser
1               5

<210> SEQ ID NO 44
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 44

Gly Gly Lys Leu Ala Lys Lys Lys
1               5

<210> SEQ ID NO 45
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 45

Gly Gly Lys Leu Ala Lys Lys Ser
1               5

<210> SEQ ID NO 46
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 46

Gly Gly Lys Leu Ser Lys Lys Lys Gly Tyr Asn Val Asn
1               5                   10

<210> SEQ ID NO 47
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 47

Gly Ala Lys Leu Ser Lys Lys Lys Lys Gly Tyr Asn Val Asn
1               5                   10
```

```
<210> SEQ ID NO 48
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 48

Gly Gly Lys Gln Ser Lys Lys Lys Gly Tyr Asn Val Asn
1               5                   10

<210> SEQ ID NO 49
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 49

Gly Gly Lys Leu Ala Lys Lys Lys Gly Tyr Asn Val Asn
1               5                   10

<210> SEQ ID NO 50
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 50

Gly Gly Lys Leu Ser Lys Lys Lys Gly Tyr Ser Gly Gly
1               5                   10

<210> SEQ ID NO 51
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 51

Gly Gly Lys Leu Ser Lys Lys Lys Gly Ser Gly Gly Ser
1               5                   10

<210> SEQ ID NO 52
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 52

Gly Gly Lys Leu Ser Lys Lys Lys Ser Gly Gly Ser Gly
1               5                   10

<210> SEQ ID NO 53
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 53

Gly Gly Lys Leu Ser Lys Lys Lys Ser Gly Gly Ser Gly Gly
1               5                   10

<210> SEQ ID NO 54
```

```
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 54

Gly Gly Lys Leu Ser Lys Ser Gly Gly Ser Gly Gly Ser
1               5                   10

<210> SEQ ID NO 55
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 55

Gly Gly Lys Leu Ser Lys Ser Gly Gly Ser Gly Gly Ser Val
1               5                   10

<210> SEQ ID NO 56
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 56

Gly Ala Lys Lys Ser Lys Lys Arg Phe Ser Phe Lys Lys Ser
1               5                   10

<210> SEQ ID NO 57
<211> LENGTH: 29
<212> TYPE: PRT
<213> ORGANISM: artificial sequence
<220> FEATURE:
<223> OTHER INFORMATION: Scaffold Y Effector Domain

<400> SEQUENCE: 57

Gly Gly Lys Leu Ser Lys Lys Lys Gly Tyr Asn Val Asn Asp Glu
1               5                   10                  15

Lys Ala Lys Glu Lys Asp Lys Lys Ala Glu Gly Ala Ala
            20                  25

<210> SEQ ID NO 58
<211> LENGTH: 28
<212> TYPE: PRT
<213> ORGANISM: artificial sequence
<220> FEATURE:
<223> OTHER INFORMATION: Scaffold Y Effector Domain

<400> SEQUENCE: 58

Gly Gly Lys Leu Ser Lys Lys Lys Gly Tyr Asn Val Asn Asp Glu
1               5                   10                  15

Lys Ala Lys Glu Lys Asp Lys Lys Ala Glu Gly Ala
            20                  25

<210> SEQ ID NO 59
<211> LENGTH: 27
<212> TYPE: PRT
<213> ORGANISM: artificial sequence
<220> FEATURE:
<223> OTHER INFORMATION: Scaffold Y Effector Domain

<400> SEQUENCE: 59
```

Gly Gly Lys Leu Ser Lys Lys Lys Gly Tyr Asn Val Asn Asp Glu
1               5                   10                  15

Lys Ala Lys Glu Lys Asp Lys Lys Ala Glu Gly
            20                  25

<210> SEQ ID NO 60
<211> LENGTH: 26
<212> TYPE: PRT
<213> ORGANISM: artificial sequence
<220> FEATURE:
<223> OTHER INFORMATION: Scaffold Y Effector Domain

<400> SEQUENCE: 60

Gly Gly Lys Leu Ser Lys Lys Lys Gly Tyr Asn Val Asn Asp Glu
1               5                   10                  15

Lys Ala Lys Glu Lys Asp Lys Lys Ala Glu
            20                  25

<210> SEQ ID NO 61
<211> LENGTH: 25
<212> TYPE: PRT
<213> ORGANISM: artificial sequence
<220> FEATURE:
<223> OTHER INFORMATION: Scaffold Y Effector Domain

<400> SEQUENCE: 61

Gly Gly Lys Leu Ser Lys Lys Lys Gly Tyr Asn Val Asn Asp Glu
1               5                   10                  15

Lys Ala Lys Glu Lys Asp Lys Lys Ala
            20                  25

<210> SEQ ID NO 62
<211> LENGTH: 24
<212> TYPE: PRT
<213> ORGANISM: artificial sequence
<220> FEATURE:
<223> OTHER INFORMATION: Scaffold Y Effector Domain

<400> SEQUENCE: 62

Gly Gly Lys Leu Ser Lys Lys Lys Gly Tyr Asn Val Asn Asp Glu
1               5                   10                  15

Lys Ala Lys Glu Lys Asp Lys Lys
            20

<210> SEQ ID NO 63
<211> LENGTH: 23
<212> TYPE: PRT
<213> ORGANISM: artificial sequence
<220> FEATURE:
<223> OTHER INFORMATION: Scaffold Y Effector Domain

<400> SEQUENCE: 63

Gly Gly Lys Leu Ser Lys Lys Lys Gly Tyr Asn Val Asn Asp Glu
1               5                   10                  15

Lys Ala Lys Glu Lys Asp Lys
            20

<210> SEQ ID NO 64
<211> LENGTH: 22
<212> TYPE: PRT
<213> ORGANISM: artificial sequence
<220> FEATURE:
<223> OTHER INFORMATION: Scaffold Y Effector Domain

<400> SEQUENCE: 64

```
Gly Gly Lys Leu Ser Lys Lys Lys Gly Tyr Asn Val Asn Asp Glu
1               5                   10                  15

Lys Ala Lys Glu Lys Asp
            20
```

<210> SEQ ID NO 65
<211> LENGTH: 21
<212> TYPE: PRT
<213> ORGANISM: artificial sequence
<220> FEATURE:
<223> OTHER INFORMATION: Scaffold Y Effector Domain

<400> SEQUENCE: 65

```
Gly Gly Lys Leu Ser Lys Lys Lys Gly Tyr Asn Val Asn Asp Glu
1               5                   10                  15

Lys Ala Lys Glu Lys
            20
```

<210> SEQ ID NO 66
<211> LENGTH: 20
<212> TYPE: PRT
<213> ORGANISM: artificial sequence
<220> FEATURE:
<223> OTHER INFORMATION: Scaffold Y Effector Domain

<400> SEQUENCE: 66

```
Gly Gly Lys Leu Ser Lys Lys Lys Gly Tyr Asn Val Asn Asp Glu
1               5                   10                  15

Lys Ala Lys Glu
            20
```

<210> SEQ ID NO 67
<211> LENGTH: 19
<212> TYPE: PRT
<213> ORGANISM: artificial sequence
<220> FEATURE:
<223> OTHER INFORMATION: Scaffold Y Effector Domain

<400> SEQUENCE: 67

```
Gly Gly Lys Leu Ser Lys Lys Lys Gly Tyr Asn Val Asn Asp Glu
1               5                   10                  15

Lys Ala Lys
```

<210> SEQ ID NO 68
<211> LENGTH: 18
<212> TYPE: PRT
<213> ORGANISM: artificial sequence
<220> FEATURE:
<223> OTHER INFORMATION: Scaffold Y Effector Domain

<400> SEQUENCE: 68

```
Gly Gly Lys Leu Ser Lys Lys Lys Gly Tyr Asn Val Asn Asp Glu
1               5                   10                  15

Lys Ala
```

<210> SEQ ID NO 69
<211> LENGTH: 17
<212> TYPE: PRT
<213> ORGANISM: artificial sequence
<220> FEATURE:
<223> OTHER INFORMATION: Scaffold Y Effector Domain

<400> SEQUENCE: 69

Gly Gly Lys Leu Ser Lys Lys Lys Gly Tyr Asn Val Asn Asp Glu
1               5                   10                  15

Lys

<210> SEQ ID NO 70
<211> LENGTH: 16
<212> TYPE: PRT
<213> ORGANISM: artificial sequence
<220> FEATURE:
<223> OTHER INFORMATION: Scaffold Y Effector Domain

<400> SEQUENCE: 70

Gly Gly Lys Leu Ser Lys Lys Lys Gly Tyr Asn Val Asn Asp Glu
1               5                   10                  15

<210> SEQ ID NO 71
<211> LENGTH: 15
<212> TYPE: PRT
<213> ORGANISM: artificial sequence
<220> FEATURE:
<223> OTHER INFORMATION: Scaffold Y Effector Domain

<400> SEQUENCE: 71

Gly Gly Lys Leu Ser Lys Lys Lys Gly Tyr Asn Val Asn Asp
1               5                   10                  15

<210> SEQ ID NO 72
<211> LENGTH: 13
<212> TYPE: PRT
<213> ORGANISM: artificial sequence
<220> FEATURE:
<223> OTHER INFORMATION: Scaffold Y Effector Domain

<400> SEQUENCE: 72

Gly Gly Lys Leu Ser Lys Lys Lys Gly Tyr Asn Val
1               5                   10

<210> SEQ ID NO 73
<211> LENGTH: 12
<212> TYPE: PRT
<213> ORGANISM: artificial sequence
<220> FEATURE:
<223> OTHER INFORMATION: Scaffold Y Effector Domain

<400> SEQUENCE: 73

Gly Gly Lys Leu Ser Lys Lys Lys Gly Tyr Asn
1               5                   10

<210> SEQ ID NO 74
<211> LENGTH: 11
<212> TYPE: PRT
<213> ORGANISM: artificial sequence
<220> FEATURE:
<223> OTHER INFORMATION: Scaffold Y Effector Domain

<400> SEQUENCE: 74

Gly Gly Lys Leu Ser Lys Lys Lys Gly Tyr
1               5                   10

<210> SEQ ID NO 75
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 75

```
Gly Gly Lys Leu Ser Lys Lys Lys Lys Gly
1               5                   10
```

<210> SEQ ID NO 76
<211> LENGTH: 9
<212> TYPE: PRT
<213> ORGANISM: artificial sequence
<220> FEATURE:
<223> OTHER INFORMATION: Scaffold Y Effector Domain

<400> SEQUENCE: 76

```
Gly Gly Lys Leu Ser Lys Lys Lys Lys
1               5
```

<210> SEQ ID NO 77
<211> LENGTH: 28
<212> TYPE: PRT
<213> ORGANISM: artificial sequence
<220> FEATURE:
<223> OTHER INFORMATION: Scaffold Y Effector Domain

<400> SEQUENCE: 77

```
Gly Ala Lys Lys Ser Lys Lys Arg Phe Ser Phe Lys Lys Ser Phe Lys
1               5                   10                  15

Leu Ser Gly Phe Ser Phe Lys Lys Asn Lys Lys Glu
            20                  25
```

<210> SEQ ID NO 78
<211> LENGTH: 27
<212> TYPE: PRT
<213> ORGANISM: artificial sequence
<220> FEATURE:
<223> OTHER INFORMATION: Scaffold Y Effector Domain

<400> SEQUENCE: 78

```
Gly Ala Lys Lys Ser Lys Lys Arg Phe Ser Phe Lys Lys Ser Phe Lys
1               5                   10                  15

Leu Ser Gly Phe Ser Phe Lys Lys Asn Lys Lys
            20                  25
```

<210> SEQ ID NO 79
<211> LENGTH: 26
<212> TYPE: PRT
<213> ORGANISM: artificial sequence
<220> FEATURE:
<223> OTHER INFORMATION: Scaffold Y Effector Domain

<400> SEQUENCE: 79

```
Gly Ala Lys Lys Ser Lys Lys Arg Phe Ser Phe Lys Lys Ser Phe Lys
1               5                   10                  15

Leu Ser Gly Phe Ser Phe Lys Lys Asn Lys
            20                  25
```

<210> SEQ ID NO 80
<211> LENGTH: 25
<212> TYPE: PRT
<213> ORGANISM: artificial sequence
<220> FEATURE:
<223> OTHER INFORMATION: Scaffold Y Effector Domain

<400> SEQUENCE: 80

```
Gly Ala Lys Lys Ser Lys Lys Arg Phe Ser Phe Lys Lys Ser Phe Lys
1               5                   10                  15

Leu Ser Gly Phe Ser Phe Lys Lys Asn
```

20                  25

<210> SEQ ID NO 81
<211> LENGTH: 24
<212> TYPE: PRT
<213> ORGANISM: artificial sequence
<220> FEATURE:
<223> OTHER INFORMATION: Scaffold Y Effector Domain

<400> SEQUENCE: 81

Gly Ala Lys Lys Ser Lys Lys Arg Phe Ser Phe Lys Lys Ser Phe Lys
1               5                   10                  15

Leu Ser Gly Phe Ser Phe Lys Lys
            20

<210> SEQ ID NO 82
<211> LENGTH: 23
<212> TYPE: PRT
<213> ORGANISM: artificial sequence
<220> FEATURE:
<223> OTHER INFORMATION: Scaffold Y Effector Domain

<400> SEQUENCE: 82

Gly Ala Lys Lys Ser Lys Lys Arg Phe Ser Phe Lys Lys Ser Phe Lys
1               5                   10                  15

Leu Ser Gly Phe Ser Phe Lys
            20

<210> SEQ ID NO 83
<211> LENGTH: 22
<212> TYPE: PRT
<213> ORGANISM: artificial sequence
<220> FEATURE:
<223> OTHER INFORMATION: Scaffold Y Effector Domain

<400> SEQUENCE: 83

Gly Ala Lys Lys Ser Lys Lys Arg Phe Ser Phe Lys Lys Ser Phe Lys
1               5                   10                  15

Leu Ser Gly Phe Ser Phe
            20

<210> SEQ ID NO 84
<211> LENGTH: 21
<212> TYPE: PRT
<213> ORGANISM: artificial sequence
<220> FEATURE:
<223> OTHER INFORMATION: Scaffold Y Effector Domain

<400> SEQUENCE: 84

Gly Ala Lys Lys Ser Lys Lys Arg Phe Ser Phe Lys Lys Ser Phe Lys
1               5                   10                  15

Leu Ser Gly Phe Ser
            20

<210> SEQ ID NO 85
<211> LENGTH: 20
<212> TYPE: PRT
<213> ORGANISM: artificial sequence
<220> FEATURE:
<223> OTHER INFORMATION: Scaffold Y Effector Domain

<400> SEQUENCE: 85

Gly Ala Lys Lys Ser Lys Lys Arg Phe Ser Phe Lys Lys Ser Phe Lys
1               5                   10                  15

Leu Ser Gly Phe
            20

<210> SEQ ID NO 86
<211> LENGTH: 19
<212> TYPE: PRT
<213> ORGANISM: artificial sequence
<220> FEATURE:
<223> OTHER INFORMATION: Scaffold Y Effector Domain

<400> SEQUENCE: 86

Gly Ala Lys Lys Ser Lys Lys Arg Phe Ser Phe Lys Lys Ser Phe Lys
1               5                   10                  15

Leu Ser Gly

<210> SEQ ID NO 87
<211> LENGTH: 18
<212> TYPE: PRT
<213> ORGANISM: artificial sequence
<220> FEATURE:
<223> OTHER INFORMATION: Scaffold Y Effector Domain

<400> SEQUENCE: 87

Gly Ala Lys Lys Ser Lys Lys Arg Phe Ser Phe Lys Lys Ser Phe Lys
1               5                   10                  15

Leu Ser

<210> SEQ ID NO 88
<211> LENGTH: 17
<212> TYPE: PRT
<213> ORGANISM: artificial sequence
<220> FEATURE:
<223> OTHER INFORMATION: Scaffold Y Effector Domain

<400> SEQUENCE: 88

Gly Ala Lys Lys Ser Lys Lys Arg Phe Ser Phe Lys Lys Ser Phe Lys
1               5                   10                  15

Leu

<210> SEQ ID NO 89
<211> LENGTH: 16
<212> TYPE: PRT
<213> ORGANISM: artificial sequence
<220> FEATURE:
<223> OTHER INFORMATION: Scaffold Y Effector Domain

<400> SEQUENCE: 89

Gly Ala Lys Lys Ser Lys Lys Arg Phe Ser Phe Lys Lys Ser Phe Lys
1               5                   10                  15

<210> SEQ ID NO 90
<211> LENGTH: 15
<212> TYPE: PRT
<213> ORGANISM: artificial sequence
<220> FEATURE:
<223> OTHER INFORMATION: Scaffold Y Effector Domain

<400> SEQUENCE: 90

Gly Ala Lys Lys Ser Lys Lys Arg Phe Ser Phe Lys Lys Ser Phe
1               5                   10                  15

<210> SEQ ID NO 91
<211> LENGTH: 14
<212> TYPE: PRT
<213> ORGANISM: artificial sequence

```
<220> FEATURE:
<223> OTHER INFORMATION: Scaffold Y Effector Domain

<400> SEQUENCE: 91

Gly Ala Lys Lys Ser Lys Lys Arg Phe Ser Phe Lys Lys Ser
1               5                   10

<210> SEQ ID NO 92
<211> LENGTH: 13
<212> TYPE: PRT
<213> ORGANISM: artificial sequence
<220> FEATURE:
<223> OTHER INFORMATION: Scaffold Y Effector Domain

<400> SEQUENCE: 92

Gly Ala Lys Lys Ser Lys Lys Arg Phe Ser Phe Lys Lys
1               5                   10

<210> SEQ ID NO 93
<211> LENGTH: 12
<212> TYPE: PRT
<213> ORGANISM: artificial sequence
<220> FEATURE:
<223> OTHER INFORMATION: Scaffold Y Effector Domain

<400> SEQUENCE: 93

Gly Ala Lys Lys Ser Lys Lys Arg Phe Ser Phe Lys
1               5                   10

<210> SEQ ID NO 94
<211> LENGTH: 11
<212> TYPE: PRT
<213> ORGANISM: artificial sequence
<220> FEATURE:
<223> OTHER INFORMATION: Scaffold Y Effector Domain

<400> SEQUENCE: 94

Gly Ala Lys Lys Ser Lys Lys Arg Phe Ser Phe
1               5                   10

<210> SEQ ID NO 95
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 95

Gly Ala Lys Lys Ser Lys Lys Arg Phe Ser
1               5                   10

<210> SEQ ID NO 96
<211> LENGTH: 9
<212> TYPE: PRT
<213> ORGANISM: artificial sequence
<220> FEATURE:
<223> OTHER INFORMATION: Scaffold Y Effector Domain

<400> SEQUENCE: 96

Gly Ala Lys Lys Ser Lys Lys Arg Phe
1               5

<210> SEQ ID NO 97
<211> LENGTH: 8
<212> TYPE: PRT
<213> ORGANISM: artificial sequence
<220> FEATURE:
```

```
<223> OTHER INFORMATION: Scaffold Y Effector Domain

<400> SEQUENCE: 97

Gly Ala Lys Lys Ser Lys Lys Arg
1               5

<210> SEQ ID NO 98
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 98

Gly Ala Lys Lys Ser Lys Lys
1               5

<210> SEQ ID NO 99
<211> LENGTH: 29
<212> TYPE: PRT
<213> ORGANISM: artificial sequence
<220> FEATURE:
<223> OTHER INFORMATION: Scaffold Y Effector Domain

<400> SEQUENCE: 99

Gly Ala Lys Lys Ser Lys Lys Arg Phe Ser Phe Lys Lys Ser Phe Lys
1               5                   10                  15

Leu Ser Gly Phe Ser Phe Lys Lys Asn Lys Lys Glu Ala
            20                  25

<210> SEQ ID NO 100
<211> LENGTH: 29
<212> TYPE: PRT
<213> ORGANISM: artificial sequence
<220> FEATURE:
<223> OTHER INFORMATION: Scaffold Y Effector Domain

<400> SEQUENCE: 100

Gly Ala Lys Lys Ala Lys Lys Arg Phe Ser Phe Lys Lys Ser Phe Lys
1               5                   10                  15

Leu Ser Gly Phe Ser Phe Lys Lys Asn Lys Lys Glu Ala
            20                  25

<210> SEQ ID NO 101
<211> LENGTH: 28
<212> TYPE: PRT
<213> ORGANISM: artificial sequence
<220> FEATURE:
<223> OTHER INFORMATION: Scaffold Y Effector Domain

<400> SEQUENCE: 101

Gly Ala Gln Glu Ser Lys Lys Lys Lys Lys Arg Phe Ser Phe Lys
1               5                   10                  15

Lys Ser Phe Lys Leu Ser Gly Phe Ser Phe Lys Lys
                20                  25

<210> SEQ ID NO 102
<211> LENGTH: 27
<212> TYPE: PRT
<213> ORGANISM: artificial sequence
<220> FEATURE:
<223> OTHER INFORMATION: Scaffold Y Effector Domain

<400> SEQUENCE: 102

Gly Ala Gln Glu Ser Lys Lys Lys Lys Lys Arg Phe Ser Phe Lys
```

```
                1               5                  10                  15
Lys Ser Phe Lys Leu Ser Gly Phe Ser Phe Lys
            20                  25
```

<210> SEQ ID NO 103
<211> LENGTH: 26
<212> TYPE: PRT
<213> ORGANISM: artificial sequence
<220> FEATURE:
<223> OTHER INFORMATION: Scaffold Y Effector Domain

<400> SEQUENCE: 103

```
Gly Ala Gln Glu Ser Lys Lys Lys Lys Lys Arg Phe Ser Phe Lys
1               5                  10                  15
Lys Ser Phe Lys Leu Ser Gly Phe Ser Phe
            20                  25
```

<210> SEQ ID NO 104
<211> LENGTH: 25
<212> TYPE: PRT
<213> ORGANISM: artificial sequence
<220> FEATURE:
<223> OTHER INFORMATION: Scaffold Y Effector Domain

<400> SEQUENCE: 104

```
Gly Ala Gln Glu Ser Lys Lys Lys Lys Lys Arg Phe Ser Phe Lys
1               5                  10                  15
Lys Ser Phe Lys Leu Ser Gly Phe Ser
            20                  25
```

<210> SEQ ID NO 105
<211> LENGTH: 24
<212> TYPE: PRT
<213> ORGANISM: artificial sequence
<220> FEATURE:
<223> OTHER INFORMATION: Scaffold Y Effector Domain

<400> SEQUENCE: 105

```
Gly Ala Gln Glu Ser Lys Lys Lys Lys Lys Arg Phe Ser Phe Lys
1               5                  10                  15
Lys Ser Phe Lys Leu Ser Gly Phe
            20
```

<210> SEQ ID NO 106
<211> LENGTH: 23
<212> TYPE: PRT
<213> ORGANISM: artificial sequence
<220> FEATURE:
<223> OTHER INFORMATION: Scaffold Y Effector Domain

<400> SEQUENCE: 106

```
Gly Ala Gln Glu Ser Lys Lys Lys Lys Lys Arg Phe Ser Phe Lys
1               5                  10                  15
Lys Ser Phe Lys Leu Ser Gly
            20
```

<210> SEQ ID NO 107
<211> LENGTH: 22
<212> TYPE: PRT
<213> ORGANISM: artificial sequence
<220> FEATURE:
<223> OTHER INFORMATION: Scaffold Y Effector Domain

<400> SEQUENCE: 107

```
Gly Ala Gln Glu Ser Lys Lys Lys Lys Lys Arg Phe Ser Phe Lys
1               5                   10                  15

Lys Ser Phe Lys Leu Ser
            20
```

<210> SEQ ID NO 108
<211> LENGTH: 21
<212> TYPE: PRT
<213> ORGANISM: artificial sequence
<220> FEATURE:
<223> OTHER INFORMATION: Scaffold Y Effector Domain

<400> SEQUENCE: 108

```
Gly Ala Gln Glu Ser Lys Lys Lys Lys Lys Arg Phe Ser Phe Lys
1               5                   10                  15

Lys Ser Phe Lys Leu
            20
```

<210> SEQ ID NO 109
<211> LENGTH: 20
<212> TYPE: PRT
<213> ORGANISM: artificial sequence
<220> FEATURE:
<223> OTHER INFORMATION: Scaffold Y Effector Domain

<400> SEQUENCE: 109

```
Gly Ala Gln Glu Ser Lys Lys Lys Lys Lys Arg Phe Ser Phe Lys
1               5                   10                  15

Lys Ser Phe Lys
            20
```

<210> SEQ ID NO 110
<211> LENGTH: 19
<212> TYPE: PRT
<213> ORGANISM: artificial sequence
<220> FEATURE:
<223> OTHER INFORMATION: Scaffold Y Effector Domain

<400> SEQUENCE: 110

```
Gly Ala Gln Glu Ser Lys Lys Lys Lys Lys Arg Phe Ser Phe Lys
1               5                   10                  15

Lys Ser Phe
```

<210> SEQ ID NO 111
<211> LENGTH: 18
<212> TYPE: PRT
<213> ORGANISM: artificial sequence
<220> FEATURE:
<223> OTHER INFORMATION: Scaffold Y Effector Domain

<400> SEQUENCE: 111

```
Gly Ala Gln Glu Ser Lys Lys Lys Lys Lys Arg Phe Ser Phe Lys
1               5                   10                  15

Lys Ser
```

<210> SEQ ID NO 112
<211> LENGTH: 17
<212> TYPE: PRT
<213> ORGANISM: artificial sequence
<220> FEATURE:
<223> OTHER INFORMATION: Scaffold Y Effector Domain

<400> SEQUENCE: 112

```
Gly Ala Gln Glu Ser Lys Lys Lys Lys Lys Arg Phe Ser Phe Lys
```

```
1               5                  10                  15

Lys

<210> SEQ ID NO 113
<211> LENGTH: 16
<212> TYPE: PRT
<213> ORGANISM: artificial sequence
<220> FEATURE:
<223> OTHER INFORMATION: Scaffold Y Effector Domain

<400> SEQUENCE: 113

Gly Ala Gln Glu Ser Lys Lys Lys Lys Lys Lys Arg Phe Ser Phe Lys
1               5                  10                  15

<210> SEQ ID NO 114
<211> LENGTH: 15
<212> TYPE: PRT
<213> ORGANISM: artificial sequence
<220> FEATURE:
<223> OTHER INFORMATION: Scaffold Y Effector Domain

<400> SEQUENCE: 114

Gly Ala Gln Glu Ser Lys Lys Lys Lys Lys Lys Arg Phe Ser Phe
1               5                  10                  15

<210> SEQ ID NO 115
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 115

Gly Ala Gln Glu Ser Lys Lys Lys Lys Lys Lys Arg Phe Ser
1               5                  10

<210> SEQ ID NO 116
<211> LENGTH: 13
<212> TYPE: PRT
<213> ORGANISM: artificial sequence
<220> FEATURE:
<223> OTHER INFORMATION: Scaffold Y Effector Domain

<400> SEQUENCE: 116

Gly Ala Gln Glu Ser Lys Lys Lys Lys Lys Lys Arg Phe
1               5                  10

<210> SEQ ID NO 117
<211> LENGTH: 12
<212> TYPE: PRT
<213> ORGANISM: artificial sequence
<220> FEATURE:
<223> OTHER INFORMATION: Scaffold Y Effector Domain

<400> SEQUENCE: 117

Gly Ala Gln Glu Ser Lys Lys Lys Lys Lys Lys Arg
1               5                  10

<210> SEQ ID NO 118
<211> LENGTH: 11
<212> TYPE: PRT
<213> ORGANISM: artificial sequence
<220> FEATURE:
<223> OTHER INFORMATION: Scaffold Y Effector Domain

<400> SEQUENCE: 118
```

```
Gly Ala Gln Glu Ser Lys Lys Lys Lys Lys
1               5                   10
```

<210> SEQ ID NO 119
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 119

```
Gly Ala Gln Glu Ser Lys Lys Lys Lys
1               5                   10
```

<210> SEQ ID NO 120
<211> LENGTH: 9
<212> TYPE: PRT
<213> ORGANISM: artificial sequence
<220> FEATURE:
<223> OTHER INFORMATION: Scaffold Y Effector Domain

<400> SEQUENCE: 120

```
Gly Ala Gln Glu Ser Lys Lys Lys Lys
1               5
```

<210> SEQ ID NO 121
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 121

```
Gly Ala Gln Glu Ser Lys Lys Lys
1               5
```

<210> SEQ ID NO 122
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 122

```
Gly Ala Gln Glu Ser Lys Lys
1               5
```

<210> SEQ ID NO 123
<211> LENGTH: 30
<212> TYPE: PRT
<213> ORGANISM: artificial sequence
<220> FEATURE:
<223> OTHER INFORMATION: Scaffold Y Effector Domain

<400> SEQUENCE: 123

```
Gly Ser Gln Ser Ser Lys Lys Lys Lys Lys Phe Ser Phe Lys Lys
1               5                   10                  15

Pro Phe Lys Leu Ser Gly Leu Ser Phe Lys Arg Asn Arg Lys
            20                  25                  30
```

<210> SEQ ID NO 124
<211> LENGTH: 29
<212> TYPE: PRT
<213> ORGANISM: artificial sequence
<220> FEATURE:
<223> OTHER INFORMATION: Scaffold Y Effector Domain

```
<400> SEQUENCE: 124

Gly Ser Gln Ser Ser Lys Lys Lys Lys Lys Phe Ser Phe Lys Lys
1               5                   10                  15

Pro Phe Lys Leu Ser Gly Leu Ser Phe Lys Arg Asn Arg
            20                  25

<210> SEQ ID NO 125
<211> LENGTH: 28
<212> TYPE: PRT
<213> ORGANISM: artificial sequence
<220> FEATURE:
<223> OTHER INFORMATION: Scaffold Y Effector Domain

<400> SEQUENCE: 125

Gly Ser Gln Ser Ser Lys Lys Lys Lys Lys Phe Ser Phe Lys Lys
1               5                   10                  15

Pro Phe Lys Leu Ser Gly Leu Ser Phe Lys Arg Asn
            20                  25

<210> SEQ ID NO 126
<211> LENGTH: 27
<212> TYPE: PRT
<213> ORGANISM: artificial sequence
<220> FEATURE:
<223> OTHER INFORMATION: Scaffold Y Effector Domain

<400> SEQUENCE: 126

Gly Ser Gln Ser Ser Lys Lys Lys Lys Lys Phe Ser Phe Lys Lys
1               5                   10                  15

Pro Phe Lys Leu Ser Gly Leu Ser Phe Lys Arg
            20                  25

<210> SEQ ID NO 127
<211> LENGTH: 26
<212> TYPE: PRT
<213> ORGANISM: artificial sequence
<220> FEATURE:
<223> OTHER INFORMATION: Scaffold Y Effector Domain

<400> SEQUENCE: 127

Gly Ser Gln Ser Ser Lys Lys Lys Lys Lys Phe Ser Phe Lys Lys
1               5                   10                  15

Pro Phe Lys Leu Ser Gly Leu Ser Phe Lys
            20                  25

<210> SEQ ID NO 128
<211> LENGTH: 25
<212> TYPE: PRT
<213> ORGANISM: artificial sequence
<220> FEATURE:
<223> OTHER INFORMATION: Scaffold Y Effector Domain

<400> SEQUENCE: 128

Gly Ser Gln Ser Ser Lys Lys Lys Lys Lys Phe Ser Phe Lys Lys
1               5                   10                  15

Pro Phe Lys Leu Ser Gly Leu Ser Phe
            20                  25

<210> SEQ ID NO 129
<211> LENGTH: 24
<212> TYPE: PRT
<213> ORGANISM: artificial sequence
<220> FEATURE:
<223> OTHER INFORMATION: Scaffold Y Effector Domain
```

```
<400> SEQUENCE: 129

Gly Ser Gln Ser Ser Lys Lys Lys Lys Lys Phe Ser Phe Lys Lys
1               5                   10                  15

Pro Phe Lys Leu Ser Gly Leu Ser
            20

<210> SEQ ID NO 130
<211> LENGTH: 23
<212> TYPE: PRT
<213> ORGANISM: artificial sequence
<220> FEATURE:
<223> OTHER INFORMATION: Scaffold Y Effector Domain

<400> SEQUENCE: 130

Gly Ser Gln Ser Ser Lys Lys Lys Lys Lys Phe Ser Phe Lys Lys
1               5                   10                  15

Pro Phe Lys Leu Ser Gly Leu
            20

<210> SEQ ID NO 131
<211> LENGTH: 22
<212> TYPE: PRT
<213> ORGANISM: artificial sequence
<220> FEATURE:
<223> OTHER INFORMATION: Scaffold Y Effector Domain

<400> SEQUENCE: 131

Gly Ser Gln Ser Ser Lys Lys Lys Lys Lys Phe Ser Phe Lys Lys
1               5                   10                  15

Pro Phe Lys Leu Ser Gly
            20

<210> SEQ ID NO 132
<211> LENGTH: 21
<212> TYPE: PRT
<213> ORGANISM: artificial sequence
<220> FEATURE:
<223> OTHER INFORMATION: Scaffold Y Effector Domain

<400> SEQUENCE: 132

Gly Ser Gln Ser Ser Lys Lys Lys Lys Lys Phe Ser Phe Lys Lys
1               5                   10                  15

Pro Phe Lys Leu Ser
            20

<210> SEQ ID NO 133
<211> LENGTH: 20
<212> TYPE: PRT
<213> ORGANISM: artificial sequence
<220> FEATURE:
<223> OTHER INFORMATION: Scaffold Y Effector Domain

<400> SEQUENCE: 133

Gly Ser Gln Ser Ser Lys Lys Lys Lys Lys Phe Ser Phe Lys Lys
1               5                   10                  15

Pro Phe Lys Leu
            20

<210> SEQ ID NO 134
<211> LENGTH: 19
<212> TYPE: PRT
<213> ORGANISM: artificial sequence
<220> FEATURE:
```

<223> OTHER INFORMATION: Scaffold Y Effector Domain

<400> SEQUENCE: 134

Gly Ser Gln Ser Ser Lys Lys Lys Lys Lys Phe Ser Phe Lys Lys
1               5                   10                  15

Pro Phe Lys

<210> SEQ ID NO 135
<211> LENGTH: 18
<212> TYPE: PRT
<213> ORGANISM: artificial sequence
<220> FEATURE:
<223> OTHER INFORMATION: Scaffold Y Effector Domain

<400> SEQUENCE: 135

Gly Ser Gln Ser Ser Lys Lys Lys Lys Lys Phe Ser Phe Lys Lys
1               5                   10                  15

Pro Phe

<210> SEQ ID NO 136
<211> LENGTH: 17
<212> TYPE: PRT
<213> ORGANISM: artificial sequence
<220> FEATURE:
<223> OTHER INFORMATION: Scaffold Y Effector Domain

<400> SEQUENCE: 136

Gly Ser Gln Ser Ser Lys Lys Lys Lys Lys Phe Ser Phe Lys Lys
1               5                   10                  15

Pro

<210> SEQ ID NO 137
<211> LENGTH: 16
<212> TYPE: PRT
<213> ORGANISM: artificial sequence
<220> FEATURE:
<223> OTHER INFORMATION: Scaffold Y Effector Domain

<400> SEQUENCE: 137

Gly Ser Gln Ser Ser Lys Lys Lys Lys Lys Phe Ser Phe Lys Lys
1               5                   10                  15

<210> SEQ ID NO 138
<211> LENGTH: 15
<212> TYPE: PRT
<213> ORGANISM: artificial sequence
<220> FEATURE:
<223> OTHER INFORMATION: Scaffold Y Effector Domain

<400> SEQUENCE: 138

Gly Ser Gln Ser Ser Lys Lys Lys Lys Lys Phe Ser Phe Lys
1               5                   10                  15

<210> SEQ ID NO 139
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 139

Gly Ser Gln Ser Ser Lys Lys Lys Lys Lys Phe Ser Phe
1               5                   10

```
<210> SEQ ID NO 140
<211> LENGTH: 13
<212> TYPE: PRT
<213> ORGANISM: artificial sequence
<220> FEATURE:
<223> OTHER INFORMATION: Scaffold Y Effector Domain

<400> SEQUENCE: 140

Gly Ser Gln Ser Ser Lys Lys Lys Lys Lys Lys Phe Ser
1               5                   10

<210> SEQ ID NO 141
<211> LENGTH: 12
<212> TYPE: PRT
<213> ORGANISM: artificial sequence
<220> FEATURE:
<223> OTHER INFORMATION: Scaffold Y Effector Domain

<400> SEQUENCE: 141

Gly Ser Gln Ser Ser Lys Lys Lys Lys Lys Lys Phe
1               5                   10

<210> SEQ ID NO 142
<211> LENGTH: 11
<212> TYPE: PRT
<213> ORGANISM: artificial sequence
<220> FEATURE:
<223> OTHER INFORMATION: Scaffold Y Effector Domain

<400> SEQUENCE: 142

Gly Ser Gln Ser Ser Lys Lys Lys Lys Lys Lys
1               5                   10

<210> SEQ ID NO 143
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 143

Gly Ser Gln Ser Ser Lys Lys Lys Lys Lys
1               5                   10

<210> SEQ ID NO 144
<211> LENGTH: 9
<212> TYPE: PRT
<213> ORGANISM: artificial sequence
<220> FEATURE:
<223> OTHER INFORMATION: Scaffold Y Effector Domain

<400> SEQUENCE: 144

Gly Ser Gln Ser Ser Lys Lys Lys Lys
1               5

<210> SEQ ID NO 145
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 145

Gly Ser Gln Ser Ser Lys Lys Lys
1               5

<210> SEQ ID NO 146
```

<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 146

Gly Ser Gln Ser Ser Lys Lys
1               5

<210> SEQ ID NO 147
<211> LENGTH: 28
<212> TYPE: PRT
<213> ORGANISM: artificial sequence
<220> FEATURE:
<223> OTHER INFORMATION: Scaffold Y Effector Domain

<400> SEQUENCE: 147

Gly Ala Lys Lys Ala Lys Lys Arg Phe Ser Phe Lys Lys Ser Phe Lys
1               5                   10                  15

Leu Ser Gly Phe Ser Phe Lys Lys Asn Lys Lys Glu
            20                  25

<210> SEQ ID NO 148
<211> LENGTH: 27
<212> TYPE: PRT
<213> ORGANISM: artificial sequence
<220> FEATURE:
<223> OTHER INFORMATION: Scaffold Y Effector Domain

<400> SEQUENCE: 148

Gly Ala Lys Lys Ala Lys Lys Arg Phe Ser Phe Lys Lys Ser Phe Lys
1               5                   10                  15

Leu Ser Gly Phe Ser Phe Lys Lys Asn Lys Lys
            20                  25

<210> SEQ ID NO 149
<211> LENGTH: 26
<212> TYPE: PRT
<213> ORGANISM: artificial sequence
<220> FEATURE:
<223> OTHER INFORMATION: Scaffold Y Effector Domain

<400> SEQUENCE: 149

Gly Ala Lys Lys Ala Lys Lys Arg Phe Ser Phe Lys Lys Ser Phe Lys
1               5                   10                  15

Leu Ser Gly Phe Ser Phe Lys Lys Asn Lys
            20                  25

<210> SEQ ID NO 150
<211> LENGTH: 25
<212> TYPE: PRT
<213> ORGANISM: artificial sequence
<220> FEATURE:
<223> OTHER INFORMATION: Scaffold Y Effector Domain

<400> SEQUENCE: 150

Gly Ala Lys Lys Ala Lys Lys Arg Phe Ser Phe Lys Lys Ser Phe Lys
1               5                   10                  15

Leu Ser Gly Phe Ser Phe Lys Lys Asn
            20                  25

<210> SEQ ID NO 151
<211> LENGTH: 24
<212> TYPE: PRT

```
<213> ORGANISM: artificial sequence
<220> FEATURE:
<223> OTHER INFORMATION: Scaffold Y Effector Domain

<400> SEQUENCE: 151

Gly Ala Lys Lys Ala Lys Lys Arg Phe Ser Phe Lys Lys Ser Phe Lys
1               5                   10                  15

Leu Ser Gly Phe Ser Phe Lys Lys
            20

<210> SEQ ID NO 152
<211> LENGTH: 23
<212> TYPE: PRT
<213> ORGANISM: artificial sequence
<220> FEATURE:
<223> OTHER INFORMATION: Scaffold Y Effector Domain

<400> SEQUENCE: 152

Gly Ala Lys Lys Ala Lys Lys Arg Phe Ser Phe Lys Lys Ser Phe Lys
1               5                   10                  15

Leu Ser Gly Phe Ser Phe Lys
            20

<210> SEQ ID NO 153
<211> LENGTH: 22
<212> TYPE: PRT
<213> ORGANISM: artificial sequence
<220> FEATURE:
<223> OTHER INFORMATION: Scaffold Y Effector Domain

<400> SEQUENCE: 153

Gly Ala Lys Lys Ala Lys Lys Arg Phe Ser Phe Lys Lys Ser Phe Lys
1               5                   10                  15

Leu Ser Gly Phe Ser Phe
            20

<210> SEQ ID NO 154
<211> LENGTH: 21
<212> TYPE: PRT
<213> ORGANISM: artificial sequence
<220> FEATURE:
<223> OTHER INFORMATION: Scaffold Y Effector Domain

<400> SEQUENCE: 154

Gly Ala Lys Lys Ala Lys Lys Arg Phe Ser Phe Lys Lys Ser Phe Lys
1               5                   10                  15

Leu Ser Gly Phe Ser
            20

<210> SEQ ID NO 155
<211> LENGTH: 20
<212> TYPE: PRT
<213> ORGANISM: artificial sequence
<220> FEATURE:
<223> OTHER INFORMATION: Scaffold Y Effector Domain

<400> SEQUENCE: 155

Gly Ala Lys Lys Ala Lys Lys Arg Phe Ser Phe Lys Lys Ser Phe Lys
1               5                   10                  15

Leu Ser Gly Phe
            20

<210> SEQ ID NO 156
<211> LENGTH: 19
```

```
<212> TYPE: PRT
<213> ORGANISM: artificial sequence
<220> FEATURE:
<223> OTHER INFORMATION: Scaffold Y Effector Domain

<400> SEQUENCE: 156

Gly Ala Lys Lys Ala Lys Lys Arg Phe Ser Phe Lys Lys Ser Phe Lys
1               5                   10                  15

Leu Ser Gly

<210> SEQ ID NO 157
<211> LENGTH: 18
<212> TYPE: PRT
<213> ORGANISM: artificial sequence
<220> FEATURE:
<223> OTHER INFORMATION: Scaffold Y Effector Domain

<400> SEQUENCE: 157

Gly Ala Lys Lys Ala Lys Lys Arg Phe Ser Phe Lys Lys Ser Phe Lys
1               5                   10                  15

Leu Ser

<210> SEQ ID NO 158
<211> LENGTH: 17
<212> TYPE: PRT
<213> ORGANISM: artificial sequence
<220> FEATURE:
<223> OTHER INFORMATION: Scaffold Y Effector Domain

<400> SEQUENCE: 158

Gly Ala Lys Lys Ala Lys Lys Arg Phe Ser Phe Lys Lys Ser Phe Lys
1               5                   10                  15

Leu

<210> SEQ ID NO 159
<211> LENGTH: 16
<212> TYPE: PRT
<213> ORGANISM: artificial sequence
<220> FEATURE:
<223> OTHER INFORMATION: Scaffold Y Effector Domain

<400> SEQUENCE: 159

Gly Ala Lys Lys Ala Lys Lys Arg Phe Ser Phe Lys Lys Ser Phe Lys
1               5                   10                  15

<210> SEQ ID NO 160
<211> LENGTH: 15
<212> TYPE: PRT
<213> ORGANISM: artificial sequence
<220> FEATURE:
<223> OTHER INFORMATION: Scaffold Y Effector Domain

<400> SEQUENCE: 160

Gly Ala Lys Lys Ala Lys Lys Arg Phe Ser Phe Lys Lys Ser Phe
1               5                   10                  15

<210> SEQ ID NO 161
<211> LENGTH: 14
<212> TYPE: PRT
<213> ORGANISM: artificial sequence
<220> FEATURE:
<223> OTHER INFORMATION: Scaffold Y Effector Domain

<400> SEQUENCE: 161

Gly Ala Lys Lys Ala Lys Lys Arg Phe Ser Phe Lys Lys Ser
```

-continued

```
<210> SEQ ID NO 162
<211> LENGTH: 13
<212> TYPE: PRT
<213> ORGANISM: artificial sequence
<220> FEATURE:
<223> OTHER INFORMATION: Scaffold Y Effector Domain

<400> SEQUENCE: 162

Gly Ala Lys Lys Ala Lys Lys Arg Phe Ser Phe Lys Lys
1               5                   10

<210> SEQ ID NO 163
<211> LENGTH: 12
<212> TYPE: PRT
<213> ORGANISM: artificial sequence
<220> FEATURE:
<223> OTHER INFORMATION: Scaffold Y Effector Domain

<400> SEQUENCE: 163

Gly Ala Lys Lys Ala Lys Lys Arg Phe Ser Phe Lys
1               5                   10

<210> SEQ ID NO 164
<211> LENGTH: 11
<212> TYPE: PRT
<213> ORGANISM: artificial sequence
<220> FEATURE:
<223> OTHER INFORMATION: Scaffold Y Effector Domain

<400> SEQUENCE: 164

Gly Ala Lys Lys Ala Lys Lys Arg Phe Ser Phe
1               5                   10

<210> SEQ ID NO 165
<211> LENGTH: 10
<212> TYPE: PRT
<213> ORGANISM: artificial sequence
<220> FEATURE:
<223> OTHER INFORMATION: Scaffold Y Effector Domain

<400> SEQUENCE: 165

Gly Ala Lys Lys Ala Lys Lys Arg Phe Ser
1               5                   10

<210> SEQ ID NO 166
<211> LENGTH: 9
<212> TYPE: PRT
<213> ORGANISM: artificial sequence
<220> FEATURE:
<223> OTHER INFORMATION: Scaffold Y Effector Domain

<400> SEQUENCE: 166

Gly Ala Lys Lys Ala Lys Lys Arg Phe
1               5

<210> SEQ ID NO 167
<211> LENGTH: 8
<212> TYPE: PRT
<213> ORGANISM: artificial sequence
<220> FEATURE:
<223> OTHER INFORMATION: Scaffold Y Effector Domain

<400> SEQUENCE: 167

Gly Ala Lys Lys Ala Lys Lys Arg
1               5
```

```
<210> SEQ ID NO 168
<211> LENGTH: 7
<212> TYPE: PRT
<213> ORGANISM: artificial sequence
<220> FEATURE:
<223> OTHER INFORMATION: Scaffold Y Effector Domain

<400> SEQUENCE: 168

Gly Ala Lys Lys Ala Lys Lys
1               5
```

PROCESS FOR PREPARING EXTRACELLULAR VESICLES

CROSS-REFERENCE TO RELATED APPLICATIONS

This application claims the benefit of U.S. Provisional Patent Application No. 62/822,013, filed Mar. 21, 2019; U.S. Provisional Patent Application No. 62/835,436, filed Apr. 17, 2019; U.S. Provisional Patent Application No. 62/903,524, filed Sep. 20, 2019; U.S. Provisional Patent Application No. 62/946,895, filed Dec. 11, 2019; and U.S. Provisional Patent Application No. 62/984,141, filed Mar. 2, 2020, each of which is incorporated herein by reference in its entirety.

REFERENCE TO SEQUENCE LISTING SUBMITTED ELECTRONICALLY VIA EFS-WEB

The content of the electronically submitted sequence listing (Name: 4000_0350005_Seqlisting_ST25.txt; Size: 54,131 bytes; and Date of Creation: Jun. 13, 2022) submitted in this application is incorporated herein by reference in its entirety.

FIELD OF DISCLOSURE

The present disclosure provides multistep chromatographic methods for preparing extracellular vesicles (EVs). The methods are effective in preparing high-quality EVs on a large scale.

BACKGROUND OF DISCLOSURE

Extracellular vesicles (EVs) are important mediators of intercellular communication. They are also important biomarkers in the diagnosis of many diseases, such as cancer. As drug delivery vehicles, EVs offer many advantages over traditional drug delivery methods, especially for gene therapy. The use of EVs for therapeutic purposes requires that EVs be free or mostly free of impurities including, but not limited to, undesirable host cell proteins, DNA, carbohydrates, and lipids. Current purification methods do not offer sufficient selectivity to remove significant amounts of these impurities so additional processes are desired to improve purity.

Furthermore, synthetic nano- and/or micro-carriers such as EVs often struggle to meet clinical expectations because of heterogeneity in their physicochemical parameters that confer targeting efficiency, immune evasion, and controlled drug release. This is mainly due to the complexity of nanoparticle properties (composition, size, shape, rigidity, surface charge, hydrophilicity, stability, and ligand type and density), payload properties (drug type, solubility, loading, potency, dosing, immune response, and release kinetics), and in vivo physiological barriers to nanoparticle trafficking (immune surveillance, particle extravasation, tissue targeting, tissue penetration, and cellular uptake). Although a considerable amount of effort has been made, effective methods for isolating discrete sub-populations of EVs (especially at scale) are not yet readily available.

In addition, therapeutic use of EVs requires larger-scale production and preparation of EVs. The heterogeneity and complexity of EVs make it difficult and costly to provide EVs in a large amount, while ensuring their quality. Inherent variability of the production and preparation process make it both expensive and unpredictable.

Therefore, effective and efficient methods for large-scale production, isolation and/or sub-fractionation of EVs are needed to enable use of EVs for therapeutic purposes.

SUMMARY OF DISCLOSURE

In some aspects, the present disclosure provides a method of preparing purified extracellular vesicles (EVs) from a sample comprising EVs comprising: (i) contacting the sample with a cation exchange chromatography (CEX) resin ("CEX-process") and (ii) contacting the sample with an anion exchange chromatography (AEX) resin ("AEX-process").

In a first embodiment of the first aspect, the CEX process is performed prior to the AEX process. In a second embodiment of the first aspect, the pH of the CEX process is the same as the pH of the AEX process. In a third embodiment of the first aspect, the pH of the CEX process is lower than the pH of the AEX process. In a fourth embodiment of the first aspect, the CEX process is in a flow-through mode.

In a fifth embodiment of the first aspect, the pH of the CEX process is lower at least by 0.1, at least by 0.2, at least by 0.3, at least by 0.4, at least by 0.5, at least by 0.6, at least by 0.7, at least by 0.8, at least by 0.9, at least by 1.0, at least by 1.1, at least by 1.2, at least by 1.3, at least by 1.4, at least by 1.5, at least by 1.6, at least by 1.7, at least by 1.8, at least by 1.9, at least by 2.0, at least by 2.1, at least by 2.2, at least by 2.3, at least by 2.4, at least by 2.5, at least by 2.6, at least by 2.7, at least by 2.8, at least by 2.9, at least by 3.0, at least by 3.1, at least by 3.2, at least by 3.3, at least by 3.4, at least by 3.5, at least by 3.6, at least by 3.7, at least by 3.8, at least by 3.9, at least by 4.0, at least by 4.1, at least by 4.2, at least by 4.3, at least by 4.4, at least by 4.5, at least by 4.6, at least by 4.7, at least 4.8, at least by 4.9, or at least by 5.0 than the pH of the AEX process.

In a sixth embodiment of the first aspect:
(a) the pH of the CEX process is between 5 and 6 and the pH of the AEX process is between 6 and 7;
(b) the pH of the CEX process is between 5 and 6 and the pH of the AEX process is between 7 and 8;
(c) the pH of the CEX process is between 5 and 6 and the pH of the AEX process is between 8 and 10;
(d) the pH of the CEX process is between 5 and 6 and the pH of the AEX process is between 8 and 9;
(e) the pH of the CEX process is between 5 and 6 and the pH of the AEX process is between 9 and 10;
(f) the pH of the CEX process is between 6 and 7 and the pH of the AEX process is between 7 and 8;
(g) the pH of the CEX process is between 6 and 8 and the pH of the AEX process is between 8 and 10;
(h) the pH of the CEX process is between 7 and 8 and the pH of the AEX process is between 8 and 9;
(i) the pH of the CEX process is between 7 and 8 and the pH of the AEX process is between 9 and 10;
(j) the pH of the CEX process is between 8 and 9 and the pH of the AEX process is between 9 and 10;
(k) the pH of the CEX process is between 6 and 7 and the pH of the AEX process is between 8 and 9; or
(l) the pH of the CEX process is between 6 and 7 and the pH of the AEX process is between 9 and 10.

In a seventh embodiment of the first aspect, the method further comprises contacting the AEX-processed sample with a mixed-mode chromatography, hydrophobic charge induction chromatography, or a hydrophobic interaction chromatography. In an eighth embodiment of the first aspect, the method further comprises contacting the AEX-processed sample with a mixed-mode chromatography.

In a ninth embodiment of the first aspect, the sample is run in the following sequence:
(a) CEX-AEX-MMC;
(b) CEX-MMC-AEX;
(c) AEX-CEX-MMC;
(d) AEX-MMC-CEX;
(e) MMC-CEX-AEX; or
(f) MMC-AEX-CEX.

In a tenth embodiment of the first aspect, the CEX process is repeated at least two times, at least three times, at least four times, at least five times, or at least six times. In an eleventh embodiment of the first aspect, the AEX process is repeated at least two times, at least three times, at least four times, or at least five times.

In a second aspect, the present disclosure provides a method of preparing EVs comprising:
(a) contacting a sample which comprises the EVs with an anion exchange chromatography (AEX) resin, thereby obtaining an AEX-processed sample, and
(b) contacting the AEX-processed sample with a mixed-mode chromatography (MMC) resin, thereby obtaining an MM-processed sample.

In a first embodiment of the second aspect, the sample has been processed by a cation exchange chromatography (CEX) process prior to the AEX process. In a second embodiment of the second aspect, the MMC process immediately follows the AEX process.

In a third aspect, the present disclosure provides a method of preparing extracellular vesicles (EVs) comprising:
(a) contacting a sample which comprises the EVs with a CEX resin, thereby obtaining a CEX-processed sample, and
(b) contacting the CEX-processed sample with a MMC resin, thereby obtaining an MMC-processed sample,
wherein the sample is processed by an anion exchange chromatography between the CEX process and the MMC process.

In a fourth aspect, the present disclosure provides a method of preparing EVs comprising:
(a) contacting a sample comprising the EVs with a CEX resin, thereby obtaining a CEX-processed sample;
(b) contacting the CEX-processed sample with an AEX resin, thereby obtaining an AEX-processed sample; and
(c) contacting the AEX-processed sample with an MMC resin, thereby obtaining an MMC-processed sample, wherein (a), (b), and (c) are in any order.

In a first embodiment of the fourth aspect, the AEX process immediately follows the CEX process.

In a second embodiment of the fourth aspect, the MMC process immediately follows the AEX process.

In a third embodiment of the fourth aspect, the pH of the CEX process is lower than the pH of the AEX process and/or the MMC process. In a fifth embodiment of the fourth aspect, the pH of the CEX process is lower at least by 0.1, at least by 0.2, at least by 0.3, at least by 0.4, at least by 0.5, at least by 0.6, at least by 0.7, at least by 0.8, at least by 0.9, at least by 1.0, at least by 1.1, at least by 1.2, at least by 1.3, at least by 1.4, at least by 1.5, at least by 1.6, at least by 1.7, at least by 1.8, at least by 1.9, at least by 2.0, at least by 2.1, at least by 2.2, at least by 2.3, at least by 2.4, at least by 2.5, at least by 2.6, at least by 2.7, at least by 2.8, at least by 2.9, at least by 3.0, at least by 3.1, at least by 3.2, at least by 3.3, at least by 3.4, at least by 3.5, at least by 3.6, at least by 3.7, at least by 3.8, at least by 3.9, or at least by 4.0 than the pH of the AEX process.

In a sixth embodiment of the fourth aspect:
(a) the pH of the CEX process is between 5 and 6 and the pH of the AEX process is between 6 and 7;
(b) the pH of the CEX process is between 5 and 6 and the pH of the AEX process is between 7 and 8;
(c) the pH of the CEX process is between 5 and 6 and the pH of the AEX process is between 8 and 10;
(d) the pH of the CEX process is between 5 and 6 and the pH of the AEX process is between 8 and 9;
(e) the pH of the CEX process is between 5 and 6 and the pH of the AEX process is between 9 and 10;
(f) the pH of the CEX process is between 6 and 7 and the pH of the AEX process is between 7 and 8;
(g) the pH of the CEX process is between 6 and 8 and the pH of the AEX process is between 8 and 10;
(h) the pH of the CEX process is between 7 and 8 and the pH of the AEX process is between 8 and 9;
(i) the pH of the CEX process is between 7 and 8 and the pH of the AEX process is between 9 and 10;
(j) the pH of the CEX process is between 8 and 9 and the pH of the AEX process is between 9 and 10;
(k) the pH of the CEX process is between 6 and 7 and the pH of the AEX process is between 8 and 9; or
(l) the pH of the CEX process is between 6 and 7 and the pH of the AEX process is between 9 and 10.

In a seventh embodiment of the fourth aspect, the CEX process is in a flow-through mode. In an eighth embodiment of the fourth aspect, the CEX process is repeated at least two times, at least three times, at least four times, at least five times, or at least six times. In a ninth embodiment of the fourth aspect, the AEX process is repeated at least two times, at least three times, at least four times, or at least five times.

In a tenth embodiment of the fourth aspect, the sample comprising EVs has been pretreated prior to the CEX process or the AEX process. In an eleventh embodiment of the fourth aspect, the sample prior to pretreatment is in harvest media at a volume of about 100 L, about 200 L, about 300 L, abut 400 L, about 500 L, about 600 L, about 700 L, about 800 L, about 900 L, about 1000 L, or about 2000 L. In a twelfth embodiment of the fourth aspect, the sample is in harvest media at a volume of about 500 L. In a thirteenth embodiment of the fourth aspect, pretreatment comprises, clarification step, nuclease treatment, ultrafiltration/diafiltration, or any combination thereof. In a fifteenth embodiment of the fourth aspect, clarification comprises depth filtration, centrifugation, acoustic separation, flocculation, or any combination thereof. In a sixteenth embodiment of the fourth aspect, the method further comprises subjecting the sample to a depth filtration prior to the CEX process, the AEX process, or both. In a seventeenth embodiment of the fourth aspect, the process further comprises contacting the sample with a nuclease, thereby obtaining a nuclease-treated sample, prior to the CEX process, the AEX process, or both. In an eighteenth embodiment, the nuclease is a DNase, an RNase, or both. In a nineteenth embodiment, the nuclease is BENZONASE® or DENARASE®. In some aspects, the sample is further contacted with magnesium. In some aspects, the magnesium is at a concentration of 0.01 mM to about 100 mM. In some aspects, the sample is further contacted with EDTA. In some aspects, the EDTA is present at a concentration of from about 0.001M to about 1M. In some aspects, the EDTA is present at a concentration of about 0.01M.

In a twentieth embodiment of the fourth aspect, the method further comprises subjecting the sample to one or more filtrations prior to or during the CEX, after the CEX, or both. In a twenty-first embodiment, the one or more filtrations prior to or during the CEX have a filter smaller than 0.55 microns, 0.5 microns, 0.45 microns, 0.4 microns, 0.35 microns, 0.3 microns, or 0.25 microns. In a twenty-second embodiment, the one or more filtrations after the CEX have a filter smaller than 0.35 microns, 0.3 microns, or 0.25 microns. In a twenty-third embodiment, the one or more filtrations comprise an ultrafiltration and/or diafiltration (UF/DF) prior to the CEX process, the AEX process, or both. In a twenty-fourth embodiment, the UF/DF comprises a first tangential flow filtration (TFF1), In a twenty-fifth embodiment, the TFF1 has a filter having a molecular weight cutoff of at least about 300 kDa, at least about 400 kDa, at least about 500 kDa, at least about 600 kDa, at least about 700 kDa, at least about 800 kDa, at least about 900 kDa, at least about 1000 kDa, at least about 1100 kDa, or at least about 1200 kDa. In a twenty-sixth embodiment, the TFF1 is repeated at least two times, at least three times, at least four times, at least five times, at least six times, at least seven times, at least eight times, at least nine times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, at least 28 times, at least 29 times, at least 30 times, at least 31 times, at least 32 times, at least 33 times, at least 34 times, or at least 35 times. In a twenty-seventh embodiment of the fourth aspect, the method further comprises filtering the TFF1-filtered sample through an adsorptive depth filter.

In a twenty-eighth embodiment, the method further comprises subjecting the MMC processed sample to an ultrafiltration and/or diafiltration (UF/DF). In a twenty-ninth embodiment, the UF/DF is a second tangential flow filtration (TFF2). In a thirtieth embodiment, the TFF2 has a filter having a molecular cut off of having a molecular weight cutoff of at least about 300 kDa, at least about 400 kDa, at least about 500 kDa, at least about 600 kDa, at least about 700 kDa, at least about 800 kDa, at least about 900 kDa, at least about 1000 kDa, at least about 1100 kDa, or at least about 1200 kDa. In a thirty-first embodiment, the TFF2 is not repeated.

In a fifth aspect, the present disclosure provides a method of preparing EVs comprising:
(a) subjecting a sample comprising the EVs to a depth filtration (depth-filtration processed sample);
(b) contacting the depth filtered sample to a nuclease (nuclease processed sample);
(c) contacting the nuclease treated sample to ultrafiltration and/or diafiltration (UF/DF processed sample);
(d) contacting the UF/DF treated sample with a cation exchange chromatography (CEX) resin
(CEX processed sample);
(e) contacting the CEX-processed sample with an anion exchange chromatography (AEX) resin (AEX processed sample);
(f) contacting the AEX-processed sample with a mixed-mode chromatography (MMC) resin (MINI processed sample); and
(g) subjecting the MMC processed sample to a UF/DF.

In some embodiments, one or more incubation and/or storage steps occur between one or more of (a), (b), (c), (d), (e), (f), (g), or any combination thereof. In some embodiments, the one or more incubation and/or storage step occurs for about 4 days, about 5 days, about 7 days. In some embodiments, the one or more incubation and/or storage step occurs at a temperature of from about 2° C. to about 8° C. or from about 15° C. to about 25° C.

In a first embodiment of the fifth aspect, the method results in fewer total protein impurities in the purified EVs compared to reference EVs purified by an AEX process followed by an HIC process, wherein the protein impurities are measured by a BCA assay. In a second embodiment, the method results in at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% fewer total protein impurities in the purified EV composition compared to a reference EV composition purified by an AEX process followed by an HIC process, wherein the protein impurities are measured by a BCA assay. In a third embodiment, the purified EVs have higher potency compared to reference EVs purified by an AEX process followed by an HIC process, wherein the protein impurities are measured by a BCA assay.

In a fourth embodiment of the fifth aspect, the MMC process has a pH lower than the pH of the AEX process. In a fifth embodiment of the fifth aspect, the MMC process has the same pH as the AEX process. In a sixth embodiment, the MMC process is conducted in a flow-through or weak-partitioning mode. In a seventh embodiment, the MMC process further comprises collecting a flow-through from the MMC resin. In an eighth embodiment, the MMC resin comprises at least two ligands, wherein one ligand is a hydrophobic base ligand, and one ligand is a cation exchange ligand.

In a ninth embodiment, the MMC resin comprises at least two ligands, wherein one ligand is a hydrophobic base ligand, and one ligand is an anion exchange ligand.

In a ninth embodiment of the fifth aspect, the sample comprising EVs is obtained from a mammalian cell, a bacterial cell, a eukaryotic cell, a prokaryotic cell, a plant cell, an insect cell, or any combination thereof. In a tenth embodiment, the sample comprising EVs is obtained from a mesenchymal stem cell, a human donor cell, a stem cell, an induced pluripotent stem cell (IPCs), a differentiated cell, or any combination thereof. In an eleventh embodiment, the sample comprising EVs is obtained from a HEK293 cell, a CHO cell, a BHK cell, a PER.C6 cell, a Vero cell, a HeLa cell, a PC12 cell, a sf9 cell, or any combination thereof. In a twelfth embodiment, the sample comprising EVs is obtained from bacteria, *Streptomyces, Drosophila, Xenopus* oocytes, *Escherichia coli, Bacillus subtilis*, yeast, *S. cerevisiae, Picchia pastoris*, filamentous fungi, *Neurospora crassa*, or *Aspergillus nidulans*. In a thirteenth embodiment, the EVs are originated from cells comprising a transgene. In a fourteenth embodiment, the transgene encodes a protein comprising an EV protein. In a fifteenth embodiment, the transgene encodes a heterologous protein that is not naturally-occurring in the EVs. In some aspects, the EV protein is Scaffold X. In a sixteenth embodiment, the EV protein is Prostaglandin F2 Receptor Negative Regulator (PTGFRN), Basigin (BSG), Immunoglobulin superfamily member 3 (IGSF3), Immunoglobulin superfamily member 2 (IGSF2), Integrin beta-1 (ITGB1), Integrin alpha-4 (ITGA4), 4F2 cell-surface antigen heavy chain (SLC3A2), ATP transporter, or a fragment or a modification thereof. In some aspects, the EV protein is Scaffold Y. In a seventeenth embodiment, the EV protein is BASP. In some aspects, Scaffold X or Scaffold Y is linked to a biologically active molecule. In some aspects, the biologically active molecule is an immune modulator. In some aspects, the biologically active molecule is IL-12. In some aspects, the EVs are loaded with a payload. In some aspects, the payload is a small molecule. In some aspects, the payload is a cyclic dinucleotide and/or an antisense oligonucleotide. In some aspects, the cyclic dinucleotide is a STING agonist. In some aspects, the payload is an antisense oligonucleotide. In some aspects, the antisense oligonucleotide targets a transcription factor.

In an eighteenth embodiment, the number of EV proteins expressed by transgene is at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2500, at least about 3000, at least about 3500, at least about 4000, at least about 4500, at least about 5000, at least about 5500, at least about 6000, at least about 6500, at least about 7000, at least about 7500, or at least about 8000.

In a nineteenth embodiment, the CEX resin, the AEX resin, and/or the MMC resin comprises a base matrix, wherein the base matrix is a membrane, a monolith, a hydrogel, a porous device, a nanofiber, a composite resin, a beaded resin optionally comprising inert porous shells, a solid support, a porous support, or any combination thereof. In a twentieth embodiment, the base matrix comprises cellulose, agarose, polystyrene derivatives, polyvinylether, silica, methacrylate derivatives, glass, ceramic hydroxyapatite, or acrylamide. In a twenty-first embodiment, the base matrix is attached to a chromatographic ligand. In a twenty-second embodiment, the CEX resin comprises sulfate ligands, sulfopropyl ligands, sulfobutyl ligands, sulfoisobutyl ligands, sulfoethyl ligands, sulfonate ligands, sulfonic acid ligands, carboxymethyl ligands, carboxylic acid ligands, glutamic acid ligands, aspartic acid ligands, histidine ligands, hydroxyl ligands, or ligands comprised of any amino acid.

In a twenty-third embodiment of the fifth aspect, the AEX resin comprises carboxymethyl ligands, carboxylic acid ligands, glutamic acid ligands, aspartic acid ligands, histidine ligands, hydroxyl ligands, phosphate ligands, tertiary amine ligands, quaternary amine ligands, diethaminoethyl ligands, dimethylaminoethyl ligands, trimethylaminoethyl ligands, or ligands comprised of any amino acid.

In a twenty-fourth embodiment of the fifth aspect, the MMC resin comprises tertiary amine ligands, quaternary amine ligands, diethaminoethyl ligands, ceramic hydroxyapatite ligands, ceramic fluoroapatite ligands, butyl ligands, hexyl ligands, ether ligands, hydroxyl ligands, polypropylene glycol ligands, phenyl ligands, benzyl ligands, sulfate ligands, sulfopropyl ligands, sulfobutyl ligands, sulfoisobutyl ligands, sulfoethyl ligands, sulfonate ligands, sulfonic acid ligands, carboxymethyl ligands, carboxylic acid ligands, glutamic acid ligands, aspartic acid ligands, histidine ligands, hydroxyl ligands, or phosphate ligands.

In a twenty-sixth embodiment of the fifth aspect, the EVs are exosomes. In a twenty-seventh embodiment of the fifth aspect, the sample is obtained from perfusion cell culture. In a twenty-eighth embodiment, the sample is obtained from batch cell culture. In a twenty-ninth embodiment, the sample is obtained from fed batch cell culture.

In a sixth aspect, the present disclosure provides extracellular vesicles (EVs) prepared by a method described herein.

In a seventh aspect, the present disclosure provides a pharmaceutical composition comprising the extracellular purified herein and a pharmaceutically acceptable carrier.

In an eighth aspect, the present disclosure provides a composition comprising EVs and protein impurities, wherein the protein impurities in the composition is lower than a reference composition comprising EVs purified by an AEX process followed by an HIC process, wherein the protein impurities are measured by a BCA assay. In a first embodiment of the eighth aspect, the protein impurities are at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% lower in the purified EV composition compared to a reference EV composition purified by an AEX process followed by an HIC process, wherein the protein impurities are measured by a BCA assay.

In a ninth aspect, the present disclosure provides a composition comprising EVs having higher potency, wherein the potency of the EVs is at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, or at least about 50% higher than that of a reference composition comprising EVs purified by an AEX process followed by an HIC process, wherein the protein impurities are measured by a BCA assay. In a first embodiment of the ninth aspect, the present disclosure provides the method of purifying the composition.

In a tenth aspect, the present disclosure provides a method of administering a composition described herein to a subject in need thereof.

In an eleventh aspect, the present disclosure provides a method of treating a disease or condition in a subject in need thereof comprising administering to the subject a composition described herein.

In a thirteenth aspect, the present disclosure provides a method of purifying EVs, wherein the EVs are produced in a bioreactor. In some aspects, the EVs are produced in a single-use bioreactor. In some aspects, the EVs are produced in a perfusion, ATF perfusion, or TFF perfusion bioreactor. In some aspects, the EVs are produced in a cell culture lasting about 25 days.

The methods of the present disclosure are directed to preparing purified extracellular vesicles (EVs) from a sample comprising EVs comprising clarifying the sample with filtration (filtration (1)); digesting the sample in (a) with benzonase; further clarifying the sample with filtration (filtration (2)); incubating the sample (incubation); contacting the sample with an anion exchange chromatography resin; subjecting the sample to filtration (filtration (3)); contacting the sample with a first mixed mode chromatography resin, optionally in series with a second mixed mode chromatography resin; subjecting the sample with filtration (filtration (4)); subjecting the sample with ultrafiltration and/or diafiltration; and subjecting the sample with filtration (filtration (5)).

In some aspects, the sample in (b) is mixed with $MgCl_2$. In some aspects, the amount of $MgCl_2$ is at least about 1 mM, at least about 1.5 mM, at least about 2 mM, at least about 2.5 mM, at least about 3 mM, at least about 3.5 mM, or at least about 4 mM. In some aspects, the amount of $MgCl_2$ is between 1 mM and 3 mM, between 1.5 mM and 2.5 mM, between 1 mM and 2 mM, or between 2 mM and 3 mM. In some aspects, the amount of $MgCl_2$ is about 1 mM, about 2 mM, about 3 mM, or about 4 mM. In some aspects, the incubating in (d) is at a period of less than about seven days, less than about six days, less than about five days, less than about four days, less than about three days, or less than about two days. In some aspects, the contacting with the anion exchange chromatography resin is in a bind and elute mode. In some aspects, the contacting with the first and/or the second MMC resin is in a flowthrough mode. In some aspects, filtration (1), filtration (2), filtration (3), filtration (4), and/or filtration (5) comprises filtering the sample with an about 0.2 μm filter. In some aspects, the method further comprises a storage step between two adjacent steps. In some aspects, the first MMC resin comprises a cation exchanger and hydrophobic interaction. In some aspects, the method results in a reduced endotoxin level.

BRIEF DESCRIPTION OF THE FIGURES

FIG. 3 shows particle yields across the EV production process including filtration steps between unit operations. The volumes at the top of each column indicate the volume of HEK293 cell culture medium that was purified in the process train. The unit operations listed in the same column were scaled to the harvest volume. The particle counts were measured with nanoparticle tracking analysis (NTA).

FIG. 5 shows exemplary engineered EVs containing heterogeneous structures (e.g., scaffold moiety, e.g., Scaffold X (protein X) or Scaffold Y (protein Y), payload (e.g., Ab fragments, cytokines, TNF ligands, receptors, enzymes, etc), and linker. FIG. 5 shows at least two types of modifications, i.e., luminal modification using Scaffold Y (protein Y) or surface (or exterior) modification using Scaffod X (protein X).

DETAILED DESCRIPTION OF DISCLOSURE

Figure 1:
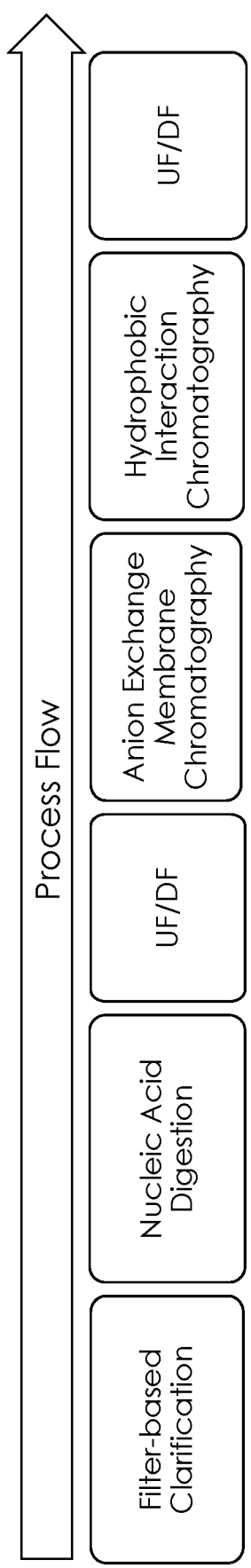
FIG. 1 is a schematic of a large-scale purification process of extracellular vesicles (EVs) comprising an anion exchange chromatography (AEX) process followed by a hydrophobic interaction chromatography (HIC) process.

The present disclosure provides a large-scale purification process of extracellular vesicles (EVs), utilizing multiple steps of chromatography. The EVs processed by the present methods can be highly purified, e.g., less protein (perlecan, agrin, and/or total proteins) impurities, higher potency, higher uniformity, or any combination thereof.

I. Definitions

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the disclosure. Thus, ranges recited herein are understood to be shorthand for all of the values within the range, inclusive of the recited endpoints. For example, a range of 1 to 10 is understood to include any number, combination of numbers, or sub-range from the group consisting of 1, 2, 3, 4, 5, 6, 7, 8, 9, and 10.

Where a value is explicitly recited, it is to be understood that values, which are about the same quantity or amount as the recited value are also within the scope of the disclosure. Where a combination is disclosed, each sub-combination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Nucleotides are referred to by their commonly accepted single-letter codes. Unless otherwise indicated, nucleotide sequences are written left to right in 5' to 3' orientation. Nucleotides are referred to herein by their commonly known one-letter symbols recommended by the IUPAC-IUB Biochemical Nomenclature Commission. Accordingly, A represents adenine, C represents cytosine, G represents guanine, T represents thymine, and U represents uracil.

Amino acid sequences are written left to right in amino to carboxy orientation. Amino acids are referred to herein by either their commonly known three letter symbols or by the one-letter symbols recommended by the IUPAC-IUB Biochemical Nomenclature Commission.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "large scale" refers to a production scale that is larger than an experimental or laboratory use for research purposes only. Large scale purification is the final production step, prior to product formulation, in the manufacture of therapeutic products, e.g., EVs. Large-scale purification requires a scale-up from laboratory scale techniques to satisfy the need for larger amounts of extremely pure test quantities of the product for analysis, characterization, testing of efficacy, clinical or field trials, and, finally, full scale commercialization. The uncompromising standards for product quality, as well as rigorous quality control of manufacturing practices embodied in current good manufacturing practices (cGMP's), provide further challenges to the scale-up of EV purification. Analysis of electrokinetic, chromatographic, adsorptive, and membrane separation techniques suggests that if yield recovery is paramount, documented purity is critical, and both must ultimately be attained within certain cost constraints. The term "large scale" as used herein indicates that the final product is for use in clinical settings and commercial sales of the purified EV products. The term "large scale" purification means a purification process of at least about 500 L, at least about 550 L, at least about 600 L, at least about 650 L, at least about 700 L, at least about 750 L, at least about 800 L, at least about 850 L, at least about 900 L, at least about 950 L, at least about 1000 L, at least about 1500 L, or at least about 2000 L cell culture harvest. In some aspects, the term "large scale" purification means a purification process of at least about 2000 L cell culture harvest. In some aspects, the term "large scale" purification means a purification process of at least about 3000 L, at least about 4000 L, at least about 5000 L, at least about 6000 L, at least about 7000 L, at least about 8000 L, at least about 9000 L, at least about 10,000 L, at least about 11,000 L, at least about 12000 L, at least about 13,000 L, at least about 14,000 L, or at least about 15,000 L cell culture harvest.

As used herein, the term "extracellular vesicle" or "EV" refers to a cell-derived vesicle comprising a membrane that encloses an internal space. Extracellular vesicles comprise all membrane-bound vesicles (e.g., exosomes, microvesicles, microsomes, extracellular bodies, apoptotic bodies, and/or nanovesicles) that have a smaller diameter than the cell from which they are derived. In some aspects, extracellular vesicles comprise a population of exosomes and/or microvesicles. In some embodiments, extracellular vesicles range in diameter from 20 nm to 1000 nm, and can comprise various macromolecular molecules either within the internal space (i.e., lumen), displayed on the external surface and/or the luminal surface of the EV, and/or spanning the membrane. In some embodiments, the molecules in the EVs can comprise nucleic acids, proteins, carbohydrates, lipids, small molecules, and/or combinations thereof. In certain embodiments, an EV comprises a scaffold moiety. By way of example and without limitation, EVs include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). EVs can be derived from a living or dead organism, explanted tissues or organs, prokaryotic or eukaryotic cells, and/or cultured cells. In some embodiments, the EVs are produced by cells that express one or more transgene products. The EVs that can be purified by the present methods include exosomes, microsomes, microvesicles, extracellular bodies, apoptotic bodies, nanovesicles, or any combination thereof.

As used herein, the term "exosome" refers to an extracellular vesicle with a diameter between 20-300 nm (e.g., between 40-200 nm). Exosomes comprise a membrane that encloses an internal space (i.e., lumen), and, in some embodiments, can be generated from a cell (e.g., producer cell) by direct plasma membrane budding or by fusion of the late endosome with the plasma membrane. As described infra, exosome can be derived from a producer cell, and isolated from the producer cell based on its size, density, biochemical parameters, or a combination thereof.

In some embodiments, the exosome of the present disclosure is engineered by covalently linking at least one moiety, e.g., payload, e.g., a biologically active molecule (e.g., a protein such as an antibody or ADC, a RNA or DNA such as an antisense oligonucleotide, a small molecule drug, a toxin, a STING agonist, or PROTAC) to the exosome, directly or indirectly, e.g., via a linker, a scaffold moiety, or any combination thereof.

As used herein, the term "payload" refers to an agent that acts on a target (e.g., a target cell) that is contacted with the EV (e.g., exosome). In some aspects, unless indicated otherwise, the term payload can be used interchangeably with the term "biologically active molecules." Non-limiting examples of payload that can be included on the EV, e.g., exosome, are an antigen, an adjuvant, and/or an immune modulator. Payloads that can be introduced into an EV, e.g., exosome, and/or a producer cell include agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, siRNA, antisense oligonucleotide, a phosphorodiamidate morpholino oligomer (PMO), a peptide-conjugated phosphorodiamidate morpholino oligomer (PPMO), or combinations thereof), amino acids (e.g., amino acids comprising a detectable moiety or a toxin or that disrupt translation), polypeptides (e.g., enzymes), lipids, carbohydrates, and small molecules (e.g., small molecule drugs and toxins). In certain aspects, a payload comprises an antigen.

In some aspects, the payload is a protein, a peptide, a glycolipid, or a glycoprotein.

In certain aspects, the payload is a polynucleotide. In some of these aspects, the polynucleotide includes, but is not limited to, an mRNA, a miRNA, an siRNA, an antisense oligonucleotide (e.g., antisense RNA or antisense DNA), a phosphorodiamidate morpholino oligomer (PMO), a peptide-conjugated phosphorodiamidate morpholino oligomer (PPMO), an shRNA, a lncRNA, a dsDNA, and combinations thereof. In some aspects, the polynucleotide is an RNA (e.g., an mRNA, a miRNA, an siRNA, an antisense oligonucleotide (e.g., antisense RNA), an shRNA, or an lncRNA). In some aspects, the polynucleotide can target a transcription factor. In some of these aspects, when the polynucleotide is an mRNA, it can be translated into a desired polypeptide. In some aspects, the polynucleotide is a microRNA (miRNA) or pre-miRNA molecule. In some of these aspects, the miRNA is delivered to the cytoplasm of the target cell, such that the miRNA molecule can silence a native mRNA in the target cell. In some aspects, the polynucleotide is a small interfering RNA (siRNA) or a short hairpin RNA (shRNA) capable of interfering with the expression of an oncogene or other dysregulating polypeptides. In some of these aspects, the siRNA is delivered to the cytoplasm of the target cell, such that the siRNA molecule can silence a native mRNA in the target cell. In some aspects, the polynucleotide is an antisense oligonucleotide (e.g., antisense RNA) that is complementary to an mRNA. In some aspects, the polynucleotide is a long non-coding RNA (lncRNA) capable of regulating gene expression and modulating diseases. In some aspects, the polynucleotide is a DNA that can be transcribed into an RNA. In some of these aspects, the transcribed RNA can be translated into a desired polypeptide.

As used herein, the term "nanovesicle" refers to an extracellular vesicle with a diameter between 20-250 nm (e.g., between 30-150 nm) and is generated from a cell (e.g., producer cell) by direct or indirect manipulation such that the nanovesicle would not be produced by the cell without the manipulation. Appropriate manipulations of the cell to produce the nanovesicles include but are not limited to serial extrusion, treatment with alkaline solutions, sonication, or combinations thereof. In some embodiments, production of nanovesicles can result in the destruction of the producer cell. In some embodiments, population of nanovesicles described herein are substantially free of vesicles that are derived from cells by way of direct budding from the plasma membrane or fusion of the late endosome with the plasma membrane. Nanovesicles, once derived from a producer cell, can be isolated from the producer cell based on its size, density, biochemical parameters, or a combination thereof. EVs can be derived from a living or dead organism, explanted tissues or organs, prokaryotic or eukaryotic cells, and/or cultured cells.

The term "microvesicle" or "microparticle", as used herein, is a type of EV, between 50 and 1,000 nanometers (nm) in diameter, found in many types of body fluids as well as the interstitial space between cells. Microvesicles are membrane-bound vesicles containing phospholipids, ranging from 100 nm to 1000 nm shed from almost all cell types. Microvesicles play a role in intercellular communication and can transport mRNA, miRNA, and proteins between cells. They originate directly from the plasma membrane of the cell and reflect the antigenic content of the cells from which they originate. They remove misfolded proteins, cytotoxic agents and metabolic waste from the cell.

The term "microsome", as used herein, refers to heterogeneous vesicle-like artifacts (~20-200 nm diameter) re-formed from pieces of the endoplasmic reticulum (ER) when eukaryotic cells are broken-up in the laboratory; microsomes are not present in healthy, living cells. Microsomes can be concentrated and separated from other cellular debris by differential centrifugation. Unbroken cells, nuclei, and mitochondria sediment out at 10,000 g, whereas soluble enzymes and fragmented ER, which contains cytochrome P450 (CYP), remain in solution (g is the Earth's gravitational acceleration). Microsomes have a reddish-brown color, due to the presence of the heme.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired EVs, that have undergone one or more processes of purification, e.g., a selection or an enrichment of the desired EV preparation. In some embodiments, isolating or purifying as used herein is the process of removing, partially removing (e.g., a fraction) the EVs from a sample containing producer cells. In some embodiments, an isolated EV composition has no detectable undesired activity or, alternatively, the level or amount of the undesired activity is at or below an acceptable level or amount. In other embodiments, an isolated EV composition has an amount and/or concentration of desired EVs at or above an acceptable amount and/or concentration. In other embodiments, the isolated EV composition is enriched as compared to the starting material (e.g., producer cell preparations) from which the composition is obtained. This enrichment can be by about 10%, about 20%, about 30%, about 40%, about 50%, about 60%, about 70%, about 80%, about 90%, about 95%, about 96%, about 97%, about 98%, about 99%, about 99.9%, about 99.99%, about 99.999%, about 99.9999%, or greater than about 99.9999% compared to the starting material. In some embodiments, isolated EV preparations according to the present disclosure are substantially free of residual contaminating products, including residual biologic products. In some embodiments, the isolated EV preparations according to the present disclosure are 100% free, about 99% free, about 98% free, about 97% free, about 96% free, about 95% free, about 94% free, about 93% free, about 92% free, about 91% free, or about 90% free of any contaminating biological matter. Residual contaminating products can include abiotic materials (including chemicals) or unwanted nucleic acids, proteins, lipids, or metabolites. Substantially free of residual biological products can also mean that the EV composition contains no detectable producer cells and that only EVs are detectable.

The term "excipient" refers to an inert substance added to assist in the purification of the EVs. Excipients can modulate the structure of the EV, modulate the adsorption rate of the EVs or the impurities, alter the polarity of the solution being purified, and perform other functions to provide an increase in the purity of the EVs.

As used herein, the term "substantially free" means that a purified composition comprising EVs comprise less than about 10% (m/v) of macromolecules by mass/volume percentage concentration. Some fractions may contain less than about 0.001%, less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1%, less than about 2%, less than about 3%, less than about 4%, less than about 5%, less than about 6%, less than about 7%, less than about 8%, less than about 9%, or less than about 10% (m/v) of macromolecules.

As used herein, the term "macromolecule" means a molecule containing a very large number of atoms, such as nucleic acids, proteins, lipids, carbohydrates, metabolites, and/or a combination thereof. In some embodiments, "macromolecules" are part of impurities that can be removed during purification as described herein.

The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art. In some aspects of the present disclosure, the biologically active molecule attached to the EV is a polypeptide, e.g., an antibody or an antigen binding portion thereof, a fusion protein, a cytokine, or an enzyme.

The term "polypeptide", as used herein, refers to proteins and peptides of any size, structure, or function. Polypeptides include gene products, naturally occurring polypeptides, synthetic polypeptides, homologs, orthologs, paralogs, fragments and other equivalents, variants, and analogs of the foregoing. A polypeptide can be a single polypeptide or can be a multi-molecular complex such as a dimer, trimer or tetramer. They can also comprise single chain or multi-chain polypeptides. Most commonly, disulfide linkages are found in multi-chain polypeptides. The term polypeptide can also apply to amino acid polymers in which one or more amino acid residues are an artificial chemical analog of a corresponding naturally occurring amino acid. In some aspects, a "peptide" can be less than or equal to 50 amino acids long, e.g., about 5, 10, 15, 20, 25, 30, 35, 40, 45, or 50 amino acids long.

A "recombinant" polypeptide or protein refers to a polypeptide or protein produced via recombinant DNA technology. Recombinantly produced polypeptides and proteins expressed in engineered host cells are considered isolated for the purpose of the disclosure, as are native or recombinant polypeptides, which have been separated, fractionated, or partially or substantially purified by any suitable technique. The polypeptides disclosed herein can be recombinantly produced using methods known in the art. Alternatively, the proteins and peptides disclosed herein can be chemically synthesized. In some aspects of the present disclosure, the Scaffold X and/or Scaffold Y proteins present in EVs are recombinantly produced by overexpressing the scaffold proteins in the producer cells, so that levels of scaffold proteins in the resulting EVs are significantly increased with respect to the levels of scaffold proteins present in EVs of producer cells not overexpressing such scaffold proteins.

As used herein, the term "scaffold moiety" refers to a molecule, e.g., a protein such as Scaffold X or Scaffold Y, that can be used to anchor a molecule, e.g., a biologically active molecule, to the EV either on the luminal surface or on the exterior surface of the EV. In certain aspects, a scaffold moiety comprises a synthetic molecule. In some aspects, a scaffold moiety comprises a non-polypeptide moiety. In other aspects, a scaffold moiety comprises, e.g., a lipid, carbohydrate, protein, or combination thereof (e.g., a glycoprotein or a proteolipid) that naturally exists in the EV. In some aspects, a scaffold moiety comprises a lipid, carbohydrate, or protein that does not naturally exist in the EV. In some aspects, a scaffold moiety comprises a lipid or carbohydrate, which naturally exists in the EV but has been enriched in the EV with respect to basal/native/wild type levels. In some aspects, a scaffold moiety comprises a protein which naturally exists in the EV but has been engineered to be enriched in the EV, e.g., by recombinant overexpression in the producer cell, with respect to basal/ native/wild type levels. In certain aspects, a scaffold moiety is Scaffold X. In some aspects, a scaffold moiety is Scaffold Y. In further aspects, a scaffold moiety comprises both Scaffold X and Scaffold Y.

As used herein, the term "Scaffold X" or "PrX" refers to EV proteins that have been identified on the surface of EVs. See, e.g., U.S. Pat. No. 10,195,290, which is incorporated herein by reference in its entirety. Non-limiting examples of Scaffold X proteins include: prostaglandin F2 receptor negative regulator ("PTGFRN"); basigin ("BSG"); immunoglobulin superfamily member 2 ("IGSF2"); immunoglobulin superfamily member 3 ("IGSF3"); immunoglobulin superfamily member 8 ("IGSF8"); integrin beta-1 ("ITGB1"); integrin alpha-4 ("ITGA4"); 4F2 cell-surface antigen heavy chain ("SLC3A2"); and a class of ATP transporter proteins ("ATP1A1," "ATP1A2," "ATP1A3," "ATP1A4," "ATP1B3," "ATP2B1," "ATP2B2," "ATP2B3," "ATP2B"). In some aspects, a Scaffold X protein can be a whole protein or a fragment thereof (e.g., functional fragment, e.g., the smallest fragment that is capable of anchoring another moiety on the exterior surface or on the luminal surface of the EV). In some aspects, a Scaffold X can anchor a moiety, e.g., a biologically active molecule to the external surface or the luminal surface of the EV. Non-limiting examples of other Scaffold X proteins include e.g., CD13 (aminopeptidase N), MME (membrane metalloendopeptidase), ENPP1 (ectonucleotide pyrophosphatase/phosphodiesterase family member 1), NRP1 (neuropilin-1), CD9, CD63, CD81, PDGFR, GPI anchor proteins, lactadherin, LAMP2, and LAMP2B.

As used herein, the term "Scaffold Y" refers to EV proteins that have been identified within the lumen of EVs. See, e.g., International Appl. No. PCT/US2018/061679, which is incorporated herein by reference in its entirety. Non-limiting examples of Scaffold Y proteins include: myristoylated alanine rich Protein Kinase C substrate ("MARCKS"); myristoylated alanine rich Protein Kinase C substrate like 1 ("MARCKSL1"); and brain acid soluble protein 1 ("BASP1"). In some aspects, a Scaffold Y protein can be a whole protein or a fragment thereof (e.g., functional fragment, e.g., the smallest fragment that is capable of anchoring a moiety on the luminal surface of the EV). In some aspects, a Scaffold Y can anchor a moiety on the luminal surface of the EV. In some aspects of the present disclosure, a moiety can be covalently attached to a Scaffold Y. In some aspects, the moiety can be attached to Scaffold Y on the luminal surface of the EV.

As used herein the term "surface-engineered EV" (e.g., Scaffold X-engineered EV) refers to an EV with the membrane or the surface of the EV modified in its composition so that the surface of the engineered EV is different from that of the EV prior to the modification or of the naturally occurring EV. The engineering can be on the surface of the EV or in the membrane of the EV so that the exterior surface of the EV is changed. For example, the membrane can be modified in its composition of, e.g., a protein, a lipid, a small molecule, a carbohydrate, or a combination thereof. The composition can be changed by a chemical, a physical, or a biological method or by being produced from a cell previously or concurrently modified by a chemical, a physical, or a biological method. Specifically, the composition can be changed by a genetic engineering or by being produced from a cell previously modified by genetic engineering. In some aspects, a surface-engineered EV comprises an exogenous protein (i.e., a protein that the EV does not naturally express) or a fragment or variant thereof that can be exposed to the surface of the EV or can be an anchoring point (attachment) for a moiety exposed on the exterior surface of the EV. In other aspects, a surface-engineered EV comprises a higher expression (e.g., higher number) of a natural EV protein (e.g., Scaffold X) or a fragment or variant thereof that can be exposed to the surface of the EV or is capable of being an anchoring point (attachment) for a moiety exposed on the surface of the EV.

As used herein the term "lumen-engineered exosome" (e.g., Scaffold Y-engineered exosome) refers to an exosome with the membrane or the lumen of the exosome modified in its composition so that the lumen of the engineered exosome is different from that of the exosome prior to the modification or of the naturally occurring exosome. The engineering can be directly on the luminal surface or in the membrane of the exosome so that the lumen of the exosome is changed. For example, the membrane is modified in its composition of a protein, a lipid, a small molecule, a carbohydrate, etc. so that the lumen of the exosome is modified. The composition can be changed by a chemical, a physical, or a biological method or by being produced from a cell previously modified by a chemical, a physical, or a biological method. Specifically, the composition can be changed by a genetic engineering or by being produced from a cell previously modified by genetic engineering. In some embodiments, a lumen-engineered exosome comprises an exogenous protein (i.e., a protein that the exosome does not naturally express) or a fragment or variant thereof that can be exposed on the luminal surface of the exosome or can be an anchoring point (attachment) for a moiety exposed on the inner layer of the exosome. In other embodiments, a lumen-engineered exosome comprises a higher expression of a natural exosome protein (e.g., Scaffold X or Scaffold Y) or a fragment or variant thereof that can be exposed to the lumen of the exosome or can be an anchoring point (attachment) for a moiety exposed on the luminal surface of the exosome.

As used herein the term "linked to," "fused," or "conjugated to" are used interchangeably and refer to a covalent or non-covalent bond formed between a first moiety and a second moiety, e.g., Scaffold X and an antigen, e.g., a scaffold moiety expressed in or on the extracellular vesicle and an antigen, e.g., Scaffold X (e.g., a PTGFRN protein), respectively, in the luminal surface of or on the external surface of the extracellular vesicle. In some aspects, a payload disclosed herein can be directly linked to the exterior surface and/or the luminal surface of an EV (e.g., exosome). As used herein, the term "directly linked," "directly fused," or "directly conjugated to" refer to the process of linking (fusing or conjugating) a moiety (e.g., a payload and/or targeting moiety) to the surface of an EV (e.g., exosome) without the use of a scaffold moiety disclosed herein.

As used herein, the term "fusion protein" refers to two or more proteins that are linked or conjugated to each other. For instance, in some aspects, a fusion protein that can be expressed in an EV (e.g., exosome) disclosed herein comprises (i) a payload (e.g., antigen, adjuvant, and/or immune modulator) and (ii) a scaffold moiety (e.g., Scaffold X and/or Scaffold Y). In some aspects, a fusion protein that can be expressed in an EV (e.g., exosome) useful for the present disclosure comprises (i) a targeting moiety and (ii) a scaffold moiety (e.g., Scaffold X and/or Scaffold Y). As described herein, in some aspects, EVs (e.g., exosomes) of the present disclosure can express multiple fusion proteins, wherein a first fusion protein comprises (i) a payload (e.g., antigen, adjuvant, and/or immune modulator) and (ii) a scaffold moiety (e.g., Scaffold X and/or Scaffold Y), and wherein a second fusion protein comprises (i) a targeting moiety and (ii) a scaffold moiety (e.g., Scaffold X and/or Scaffold Y).

II. Methods of the Present Disclosure

The present disclosure relates to large-scale isolation, purification and/or sub-fractionation of EVs by multistep chromatographic purification methods for therapeutic and commercial use of the EVs.

While there have been some attempts to purify EVs in a large, commercial scale, those attempts were not successful. A current standard process for purification involves the use of density gradient ultracentrifugation processes, e.g., Iodixanol (OPTIPREP™), which relies on "floating" the lower density exosomes through a gradient of decreasing density. This process is time consuming and is not practical for large commercial scale production of exosomes. The present disclosure thus provides methods of purifying samples comprising EVs in a large scale comprising conducting multiple chromatography processes including a CEX process. The process described herein is also superior to other (non-density gradient) ultracentrifugation processes. The present disclosure thus provides methods of purifying samples comprising EVs in a large scale comprising conducting multiple chromatography processes including a CEX process.

In some embodiments, the present disclosure is directed to a method of preparing purified EVs from a sample comprising EVs, e.g., in a large scale manufacturing process, comprising: (i) contacting the sample which comprises the EVs with a CEX resin ("CEX-processed sample") and (ii) contacting the sample with an AEX resin ("AEX-processed sample"). In some embodiments of the present disclosure, the CEX comes before the AEX. In other embodiments, the order of the CEX and AEX can be reversed. Therefore, the present method comprises (i) CEX-AEX or (ii) AEX-CEX. In other embodiments, the pH of the CEX is lower than the pH of the AEX. In other embodiments, the pH of the CEX is the same as the pH of the AEX. In some aspects, filtration can be added between the AEX and the CEX.

In other embodiments, the pH of the CEX process is lower at least by 0.1, at least by 0.2, at least by 0.3, at least by 0.4, at least by 0.5, at least by 0.6, at least by 0.7, at least by 0.8, at least by 0.9, at least by 1.0, at least by 1.1, at least by 1.2, at least by 1.3, at least by 1.4, at least by 1.5, at least by 1.6, at least by 1.7, at least by 1.8, at least by 1.9, at least by 2.0, at least by 2.1, at least by 2.2, at least by 2.3, at least by 2.4, at least by 2.5, at least by 2.6, at least by 2.7, at least by 2.8, at least by 2.9, at least by 3.0, at least by 3.1, at least by 3.2, at least by 3.3, at least by 3.4, at least by 3.5, at least by 3.6, at least by 3.7, at least by 3.8, at least by 3.9, at least by 4.0, at least by 4.1, at least by 4.2, at least by 4.3, at least by 4.4, at least by 4.5, at least by 4.6, at least by 4.7, at least 4.8, at least by 4.9, or at least by 5.0 than the pH of the AEX process.

In some embodiments, the pH of the CEX process is between 5 and 6 and the pH of the AEX process is between 6 and 7. In some embodiments, the pH of the CEX process is between 5 and 6 and the pH of the AEX process is between 7 and 8. In other embodiments, the pH of the CEX process is between 5 and 6 and the pH of the AEX process is between 8 and 10. In some embodiments, the pH of the CEX process is between 5 and 6 and the pH of the AEX process is between 8 and 9. In some embodiments, the pH of the CEX process is between 5 and 6 and the pH of the AEX process is between 9 and 10. In other embodiments, the pH of the CEX process is between 6 and 7 and the pH of the AEX process is between 7 and 8. In some embodiments, the pH of the CEX process is between 6 and 8 and the pH of the AEX process is between 8 and 10. In some embodiments, the pH of the CEX process is between 7 and 8 and the pH of the AEX process is between 8 and 9. In some embodiments, the pH of the CEX process is between 7 and 8 and the pH of the AEX process is between 9 and 10. In some embodiments, the pH of the CEX process is between 8 and 9 and the pH of the AEX process is between 9 and 10. In some embodiments, the pH of the CEX process is between 6 and 7 and the pH of the AEX process is between 8 and 9. In some embodiments, the pH of the CEX process is between 6 and 7 and the pH of the AEX process is between 9 and 10. In some aspects, the pH of the AEX and CEX process is the same and between about 7 and about 8, about 7.1, about 7.2, about 7.3, about 7.4, about 7.5, about 7.6, about 7.7, about 7.8, about 7.9 or about 8.0.

In other embodiments, the method further comprises one or more additional chromatography steps, e.g., mixed-mode chromatography, hydrophobic charge induction chromatography, and/or a hydrophobic interaction chromatography. In some embodiments, the method further comprises mixed-mode chromatography (MMC).

In some embodiments, the method comprises (i) CEX-AEX-MMC; (ii) CEX-MMC-AEX; (iii) AEX-CEX-MMC; (iv) AEX-MMC-CEX; (v) MMC-CEX-AEX; or (vi) MMC-AEX-CEX. In other embodiments, the method comprises CEX-AEX-MMC. In other aspects, the method comprises AEX-CEX-MMC.

In some embodiments, the present methods include the following:
- (i) contacting a sample comprising EVs with a CEX resin (CEX processed sample);
- (ii) contacting the CEX-processed sample with an AEX resin (AEX processed sample); and
- (iii) contacting the AEX-processed sample with a MMC resin (MMC processed sample).

In some embodiments, the present methods include the following:
- (i) contacting a sample comprising EVs with a CEX resin (CEX processed sample);
- (ii) contacting the CEX-processed sample with a MMC resin (MMC processed sample); and
- (iii) contacting the MMC-processed sample with an AEX resin (AEX processed sample).

In some embodiments, the present methods include the following:
- (i) contacting a sample comprising EVs with an AEX resin (AEX processed sample);
- (ii) contacting the AEX-processed sample with a CEX resin (CEX processed sample); and
- (iii) contacting the CEX-processed sample with a MMC resin (MMC processed sample).

In some embodiments, the present methods include the following:
- (i) contacting a sample comprising EVs with an AEX resin (AEX processed sample);
- (ii) contacting the AEX-processed sample with a MMC resin (MMC processed sample); and
- (iii) contacting the MMC-processed sample with an CEX resin (CEX processed sample).

In some embodiments, the present methods include the following:
- (i) contacting a sample comprising EVs with a MMC resin (MMC processed sample);
- (ii) contacting the MMC-processed sample with a CEX resin (CEX processed sample); and (iii) contacting the CEX-processed sample with an AEX resin (AEX processed sample).

In some embodiments, the present methods include the following:
(i) contacting a sample comprising EVs with a MMC resin (MMC processed sample);
(ii) contacting the MMC-processed sample with an AEX resin (AEX processed sample); and
(iii) contacting the AEX-processed sample with a CEX resin (CEX processed sample).

In some embodiments, the present methods include the following:
(i) contacting a sample comprising EVs with a CEX resin (CEX processed sample);
(ii) contacting the CEX-processed sample with an AEX resin (AEX processed sample); and
(iii) contacting the AEX-processed sample with a MMC resin (MMC processed sample), wherein the pH of a CEX loading buffer is lower than the pH of an AEX loading buffer.

In some embodiments, the present methods include the following:
(i) contacting a sample comprising EVs with a CEX resin (CEX processed sample);
(ii) contacting the CEX-processed sample with a MMC resin (MMC processed sample); and
(iii) contacting the MMC-processed sample with an AEX resin (AEX processed sample), wherein the pH of a CEX loading buffer is lower than the pH of an AEX loading buffer.

In some embodiments, the present methods include the following:
(i) contacting a sample comprising EVs with an AEX resin (AEX processed sample);
(ii) contacting the AEX-processed sample with an CEX resin (CEX processed sample); and
(iii) contacting the CEX-processed sample with a MMC resin (MMC processed sample), wherein the pH of a CEX loading buffer is lower than the pH of an AEX loading buffer.

In some embodiments, the present methods include the following:
(i) contacting a sample comprising EVs with an AEX resin (AEX processed sample);
(ii) contacting the AEX-processed sample with a MMC resin (MMC processed sample); and
(iii) contacting the MMC-processed sample with a CEX resin (CEX processed sample), wherein the pH of a CEX loading buffer is lower than the pH of an AEX loading buffer.

In some embodiments, the present methods include the following:
(i) contacting a sample comprising EVs with a MMC resin (MMC processed sample);
(ii) contacting the MMC-processed sample with a CEX resin (CEX processed sample); and
(iii) contacting the CEX-processed sample with an AEX resin (AEX processed sample), wherein the pH of a CEX loading buffer is lower than the pH of an AEX loading buffer.

In some embodiments, the present methods include the following:
(i) contacting a sample comprising EVs with a MMC resin (MMC processed sample);
(ii) contacting the MM-processed sample with an AEX resin (AEX processed sample); and
(iii) contacting the AEX-processed sample with a CEX resin (CEX processed sample), wherein the pH of a CEX loading buffer is lower than the pH of an AEX loading buffer.

For each chromatography (e.g., CEX, AEX, and MMC), various buffers (loading buffer, elution buffer, wash buffer, etc) and conditions can be used to maximize the yield while removing the impurities as much as possible. In some embodiments, each of the chromatography comprises a loading buffer, an elution buffer, and/or a wash buffer. In some embodiments, the loading buffer and the elution buffer can be the same. In other embodiments, the elution buffer and the wash buffer can be the same. In other embodiments, the loading and wash buffers can be the same. In some embodiments, the loading and wash buffers can be the same, but the elution buffer is different from the loading and wash buffers. In other embodiments, the loading buffer, the elution buffer, and the wash buffer are the same.

In some embodiments, CEX elution conditions can be designed to be the same as the AEX load conditions enabling straight through operation. In some embodiments, CEX elution conditions can be designed to be the same as the AEX load conditions enabling straight through operation while the CEX loading conditions (e.g., a lower pH than the elution buffer) are different from the CEX elution conditions. In some embodiments, AEX elution conditions can be designed to be the same as the MMC load conditions enabling straight through operation. Straight through processing can also be accomplished by integrated dilution or in-line titration of an elution and/or a load. In some embodiments, CEX and AEX columns can be duplexed (placed inline in series) to enable operation of both columns in a single unit operation; the CEX column operated in flow-through or weak partitioning mode with the flow-through directly binding to the downstream AEX column. In some embodiments, the product can be eluted from the AEX with a separate elution. In some embodiments, to prevent fouling and maximize reuse of the downstream column, the two columns can be separated for strips and/or other phases.

In some embodiments, selective loading, capture, elution, and/or wash can be achieved by changing salt, phosphate, or calcium concentrations, changing pH, altering temperature, adding organic modifiers, organic solvents, small molecules, detergents, zwitterions, amino acids, polymers, polyols (sucrose, glucose, trehalose, mannose, sorbitol, mannitol, glycerol, etc.), anti-oxidants (e.g., methionine), EDTA, EGTA, Polysorbate 20, Polysorbate 80, ethylene glycol, propylene glycol, polyethylene glycol, polypropylene glycol, and/or urea, adding excipients that alter the surface tension of the solution, adding excipients that alter the polarity of the solution, altering the residence time to take advantage of differential desorption rates between impurities and EVs, adding excipients that modulate the structure of the EVs, or any combination of the above.

In some aspects, loading, capture, elution, and/or wash can be achieved by using EDTA to inhibit any potential contaminating metalloproteases. In some aspects, the EDTA is present at a concentration of from about 0.0001M to about 1M in a buffer, e.g., an elution buffer for the AEX. In some aspects, the EDTA is present at a concentration of from about 0.001M to about 1M. In some aspects, the EDTA is present at a concentration of from about 0.001M to about 0.1M, from about 0.001M to about 0.09M, from about 0.002M to about 0.08M, from about 0.003M to about 0.07M, from about 0.004M to about 0.06M, from about 0.005M to about 0.05M, from about 0.006M to about 0.04M, from about 0.007M to about 0.03M, from about 0.008M to about 0.02M, or from about 0.009M to about 0.01M. In some aspects, the EDTA is present at a concentration of from about 0.01M to about 0.1M. In some aspects, the EDTA is present at a concentration of about 0.001M. In some aspects, the EDTA is present at a concentration of about 0.001M. In some aspects, the EDTA is present at a concentration of about 0.005M. In some aspects, the EDTA is present at a concentration of about 0.01M. In some aspects, the EDTA is present at a concentration of about 0.02M. In some aspects, the EDTA is present at a concentration of about 0.003M. In some aspects, the EDTA is present at a concentration of about 0.004M. In some aspects, the EDTA is present at a concentration of about 0.05M. In some aspects, the EDTA is present at a concentration of about 0.06M. In some aspects, the EDTA is present at a concentration of about 0.07M. In some aspects, the EDTA is present at a concentration of about 0.08M In some aspects, the EDTA is present at a concentration of about 0.09M In some aspects, the EDTA is present at a concentration of about 0.1M.

In some embodiments, selective loading, elution, and/or wash of EVs can be achieved by increasing the concentration of a monovalent salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, in the elution buffer for a chromatography (e.g., CEX, AEX, and/or MMC), through the use of an increasing gradient (step or linear) of a monovalent salt (e.g., sodium chloride, potassium chloride, sodium bromide, lithium chloride, sodium iodide, potassium bromide, lithium bromide, sodium fluoride, potassium fluoride, lithium fluoride, lithium iodide, sodium acetate, potassium acetate, lithium acetate, and potassium iodide), a divalent or trivalent salt (e.g., calcium chloride, magnesium chloride, calcium sulfate, sodium sulfate, magnesium sulfate, chromium trichloride, chromium sulfate, sodium citrate, iron (III) chloride, yttrium (III) chloride, potassium phosphate, potassium sulfate, sodium phosphate, ferrous chloride, calcium citrate, magnesium phosphate, and ferric chloride), or a combination thereof, at a fixed pH. In some aspects, one or more buffers, e.g., elution buffer or loading buffer, e.g., elution buffer for AEX, loading buffer for AEX, comprises NaCl.

In some embodiments, substantial EV purity can be achieved by flowing through impurities during the column loading phase, eluting impurities during selective excipient washes, and/or by selectively eluting a target during elution while leaving additional impurities bound to the column. Absorbance measurements of column eluates can suggest changes (e.g., a significant reduction) in concentrations of proteins and nucleic acids. In some embodiments, the interaction between the chromatographic resins (e.g., CEX, AEX, and/or MMC) and EVs is sufficient to enable direct capture from cell culture, clarified cell culture, concentrated cell culture, or partially purified in-process pools.

In some embodiments, excipients can be used for the washing step for one or more chromatography processes (e.g., CEX, AEX, and/or MMC). Excipient washes can improve purity or further aid in enriching, depleting, or isolating sub-populations of EVs. In some embodiments, the excipient can be a solution having specific pH ranges, salts, organic solvents, small molecules, detergents, zwitterions, amino acids, polymers, and any combination of the above.

In some embodiments, the excipient can comprise arginine, lysine, glycine, histidine, calcium, sodium, lithium, potassium, iodide, magnesium, iron, zinc, manganese, urea, propylene glycol, aluminum, ammonium, guanidinium polyethylene glycol, EDTA, EGTA, a detergent, chloride, sulfate, carboxylic acids, sialic acids, phosphate, acetate, glycine, borate, formate, perchlorate, bromine, nitrate, dithiothreitol, beta mercaptoethanol, or tri-n-butyl phosphate.

In some embodiments, the excipient can also comprise a detergent. In some embodiments, the detergent is selected from cetyl trimethylammonium chloride, octoxynol-9, TRITON™ X-100 (i.e., polyethylene glycol p-(1,1,3,3-tetramethylbutyl)-phenyl ether) and TRITON™ CG-110 available from Sigma-Aldrich; sodium dodecyl sulfate; sodium lauryl sulfate; deoxycholic acid; Polysorbate 80 (i.e., Polyoxyethylene (20) sorbitan monooleate); Polysorbate 20 (i.e., Polyoxyethylene (20) sorbitan monolaurate); alcohol ethoxylate; alkyl polyethylene glycol ether; decyl glucoside; octoglucosides; SafeCare; ECOSURF™ EH9, ECOSURF™ EH6, ECOSURF™ EH3, ECOSURF™ SA7, and ECOSURF™ SA9 available from DOW Chemical; LUTENSOL™ M5, LUTENSOL™ XL, LUTENSOL™ XP and APG™ 325N available from BASF; TOMADOL™ 900 available from AIR PRODUCTS; NATSURF™ 265 available from CRODA; SAFECARE™ 1000 available from Bestchem, TERGITOL™ L64 available from DOW; caprylic acid; CHEMBETAINE™ LEC available from Lubrizol; Mackol DG, and mixtures thereof.

In some embodiments of the multistep process, any unit operation (i.e., any step in the process) can be run in batch, semi-batch, semi-continuous, or continuous mode. In some embodiments, surge tanks can be employed to enable semi-continuous or continuous processing.

In other embodiments, the sequence of the chromatography process (e.g., CEX-AEX-MMC or AEX-CEX-MMC) can be repeated at least two times, at least three times, at least four times, at least five times, at least six times, at least seven times, at least eight times, at least nine times, at least ten times, at least 11 times, at least 12 times, at least 13 times, at least 14 times, at least 15 times, at least 16 times, at least 17 times, at least 18 times, at least 19 times, or at least 20 times.

In some embodiments, AEX and MMC columns are duplexed (placed inline in series) to enable operation of both columns in a single until operation; the AEX column is operated in bind/elute mode with the elution loaded directly onto the MMC column operation in flow-through or weak partitioning mode. In some embodiments, to prevent fouling and maximize reuse of the downstream column, the two columns can be separated for strips or other phases.

In some embodiments, the large-scale manufacturing process described herein therefore, does not utilize a centrifugation process, e.g., a density gradient ultracentrifugation. In other embodiments, the large scale manufacturing process utilizing a CEX process and an AEX process shows improved purities, e.g., less total protein impurities, less perlecan protein level, less agrin protein level, less host cell protein impurities, or any combination thereof, compared to an AEX process alone or an AEX process and another chromatography (e.g., an HIC). In some embodiments, the present methods exhibit less total protein impurities compared to an AEX process alone, an AEX process followed by an HIC process, or a density gradient ultracentrifugation as measured by a bicinchoninic acid (BCA) protein assay. The bicinchoninic acid assay (BCA assay), also known as the Smith assay, developed by Paul K. Smith at the Pierce Chemical Company, is a biochemical assay for determining the total concentration of protein in a solution (0.5 µg/mL to 1.5 mg/mL), similar to Lowry protein assay, Bradford protein assay or biuret reagent. The total protein concentration is exhibited by a color change of the sample solution from green to purple in proportion to protein concentration, which can then be measured using colorimetric techniques.

In some embodiments, the EVs purified by the present methods have total protein impurities similar to the EVs purified by a density gradient ultracentrifugation process ("Opti", see, for example, worldwideweb.sigmaaldrich.com/technical-documents/articles/biofiles/centrifugation-separations.html). In other embodiments, the present method results in at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, or at least about 30% fewer total protein impurities in the purified EV composition compared to a reference EV composition purified by an AEX process, an AEX process followed by a HIC process, or a density gradient ultracentrifugation process ("Opti") as measured by a bicinchoninic acid (BCA) protein assay. In other embodiments, the present method results in at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% fewer total protein impurities in the purified EV composition compared to a reference EV composition purified by an AEX process followed by an HIC process as measured by a bicinchoninic acid (BCA) protein assay (see, for example, worldwideweb.thermofisher.com/order/catalog/product/23225). In other embodiments, the present method results in at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% fewer perlecan level in the purified EV composition compared to a reference EV composition purified by an AEX process followed by an HIC process, as measured by an AlphaLisa assay. In other embodiments, the present method results in at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% fewer agrin level in the purified EV composition compared to a reference EV composition purified by An AEX process alone or an AEX process followed by an HIC process, as measured by an ELISA assay. In other embodiments, the present method results in at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% fewer agrin level in the purified EV composition compared to a reference EV composition purified by a density gradient ultracentrifugation process ("Opti"), as measured by an ELISA assay.

In other embodiments, the EVs purified by the present methods have higher potency compared to reference EVs purified by an AEX process or an AEX process followed by an HIC process. In other embodiments, the potency of the EVs purified by the present methods is higher than that of the EVs purified by an AEX process or an AEX process followed by an HIC process at least by about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%.

In some embodiments, the EVs purified by the present methods have a reduced endotoxin level and or a reduced beta glucan level compared to the EVs prior to the purification. The reduced level of certain impurities, e.g., virus, endotoxins and/or beta glycan, can be expressed as a calculated ratio of the titer of the impurities in the starting material and in the purified product, i.e., $\log_{10}$ reduction factor, $\log_{10}$ reduction value, or sometimes simple $\log_{10}$ clearance. The log reduction value (LRV) from the endotoxin level in the starting sample comprising EVs (prior to the purification step) to the EVs purified by the present purification method is more than about 3.0, more than about 3.1, more than about 3.2, more than about 3.3, more than about 3.4, more than about 3.5, more than about 3.6, more than about 3.7, more than about 3.8, more than about 3.9, more than about 4.0, more than about 4.1, or more than about 4.2. In some embodiments, the LRV for the endotoxin level in the EVs purified by the present method is more than 3.3 LRV.

In some embodiments, the beta glycan level in the EVs purified by the present purification method is reduced compared to that in the starting material. The LRV of the present methods for the beta glycan is more than about 3.0, more than about 2.5, more than about 2.4, more than about 2.3, more than about 2.2, more than about 2.1, more than about 2.0, more than about 1.9, more than about 1.8, more than about 1.7, more than about 1.6, more than about 1.5, or more than about 1.4. In some embodiments, the LRV for the beta glycan level in the EVs purified by the present method is more than 1.8.

In some embodiments, the present disclosure provides for characterization of EVs prepared by the methods provided herein. In some embodiments, contents of the EVs are extracted for study and characterization. In some embodiments, EVs are isolated and characterized by metrics including, but not limited to, size, shape, morphology, or molecular compositions such as nucleic acids, proteins, metabolites, and lipids. In some embodiments, EVs are tracked by their light scattering signal. Measuring a light scattering signal of EVs is described in detail in International Application PCT/US2019/038592, published as WO 2019/246591 A1 on Dec. 26, 2019, which is incorporated herein by reference in its entirety. In some embodiments, EVs are tracked by measuring their light scattering signal after a chromatography step at an emission wavelength of 556 nm and an excitation wavelength of 573 nm.

In some aspects, the methods of the present disclosure comprises two or more processes (e.g., chromatographies) connected for continuous manufacturing (e.g., purification). In some aspects, the continuous manufacturing (e.g., purification) processes are integrated with the bioreactor that produces the EVs.

Some aspects of the present method is a streamlined, quick EV purification process. In some aspects, the purification process, i.e., from cell culture media to drug substance, takes less than about 10 days, less than about 9 days, less than about 8 days, less than about 7 days, less than about 6 days, less than about 5 days, less than about 4 days, less than about 3 days, less than about 2 days, less than about 1.5 days, or less than about 1 day. In some aspects, the purification process, i.e., from cell culture media to drug substance, takes less than about 1.5 days.

The present methods comprise: (a) clarifying the sample with a filteration (filtration (1)); (b) digesting the sample in (a) with benzonase; (c) further clarifying the sample with filtration (filtration (2)); (d) incubating the sample; (e) contacting the sample with an anion exchange chromatography (AEX) resin; (f) subjecting to filtration (filtration (3)); (g) contacting the sample with a first mixed mode chromatography (MMC) resin or a cation exchange chromatography (CEX) resin, optionally in series with a second MMC resin; (h) subjecting the sample with filtration (filtration (4)); (i) subjecting the sample with ultrafiltration and difiltration; and (j) subjecting the sample with filtration (filtration (5)). In some aspects, the first MMC resin and the second MMC resin are different. In other aspects, the first MMC resin comprises a cation exchanger and hydrophobic interaction.

II.A. CEX Process

The CEX process is a form of ion exchange chromatography that separates samples based on their net surface charge. CEX specifically uses negatively charged ligands having affinity to targets having positive surface charges. Without being bound by a particular theory, EVs may be amphoteric and present positive surface charges that can be exploited for CEX purification under certain purification conditions. The method can rely on positive charges of the surface proteins on the EVs that contain basic amino acids such as lysine and arginine and/or are complexed with bivalent positively charged metals. In addition, the presence of chromatin can offer an array of basic histone proteins for CEX binding.

Various CEX resins can be used in the CEX process. In some embodiments, CEX resins comprise a CEX ligand and a base matrix. In some embodiments, the base matrix can comprise membranes, monoliths, hydrogels, nanofiber, composite resins, beaded resins, beaded resins with inert porous shells, an/or any other absorptive or convective media. In other embodiments the base matrix can comprise materials such as cellulose, agarose, polystyrene derivatives, polyvinyl ether, silica, methacrylate derivatives, glass, ceramic hydroxyapatite, acrylamide, other backbones commonly used in chromatography and known by those of skill in the art, and/or mixtures thereof.

Various CEX ligands can be used in the CEX process. In some embodiments, the CEX ligands comprise sulfate, sulfopropyl, sulfobutyl, sulfoisobutyl, sulfoethyl, sulfonate, sulfonic acid, carboxymethyl, carboxylic acid, glutamic acid, aspartic acid, histidine, hydroxyl, and/or phosphate ligands. In some embodiments, CEX ligands are used together with other conventional chromatography ligands such as sulfate ligands, tertiary amine ligands, quaternary amine ligands, diethaminoethyl ligands, butyl ligands, hexyl ligands, ether ligands, polypropylene glycol ligands, phenyl ligands, ceramic hydroxy apatite ceramic fluoroapatite ligands, amino acid ligands, or any combination thereof. In some embodiments, commercially available chromatography ligands are used, for example, those formulated as SP SEPHAROSE™ FF, SP SEPHAROSE™ HP, SP SEPHAROSE™ BB, SP SEPHAROSE™ XL, CM SEPHAROSE™ FF, CM SEPHAROSE™ HP, SOURCE™ 15S, SOURCE™ 30S, CAPTO™ S, MacroCap SP, CAPTO™ SP ImpRes, or CAPTO™ S ImpAct available from GE Healthcare; FRACTOGEL® EMD SO3-(M), FRACTOGEL® EMD SO3-(S), FRACTOGEL® EMD SE Hicap (M), ESHMUNO® S, or ESHMUNO® CPX available from Merck Millipore; TOYOPEARL® CM-650C, TOYOPEARL® CM-650M, TOYOPEARL® CM-650S, TOYOPEARL® SP-650C, TOYOPEARL® SP-650M, TOYOPEARL® SP-650S, TOYOPEARL® SP-550C, TOYOPEARL® MEGACAP® II SP-550 EC, TOYOPEARL® GIGACAP® S-650M, TOYOPEARL® GIGACAP® CM-650M, or TOYOPEARL® GIGACAP® S-650S available from Tosoh Bioscience; MACRO-PREP® High S, MACRO-PREP® 25 S, MACRO-PREP® CM, UNOSPHERE™ S, NUVIA™ S, or NUVIA™ HR-S available from BioRad Laboratories; S HYPERCEL™, CM Ceramic HYPERD® F, S Ceramic HYPERD® 20, S Ceramic HYPERD® F, CMM HYPERCEL™, or HYPERCEL™ STAR CEX, available from Pall Corporation; POROS® 50 HS, POROS® 20 HS, or POROS® XS, available from Thermo Fisher Scientific/Life Technologies; PL-SCX 1000 Å 30 μm or PL-SCX 1000 Å 10 μm, available from Agilent Technologies; CELLUFINE® MAX S-r, CELLUFINE® MAX S-h, or CELLUFINE® C-500 (m), available from JNC Corporation; BAKERBOND™ POLYABx or BAKERBOND™ POLYABx, available from Avantor Pharmaceutical Materials; YMC—BioPro S30, YMC—BioPro S75, YMC-BioPro SmartSep S10, YMC—BioPro SmartSep S30, or YMC—BioPro SmartSep S30, available from YMC; or PRAESTO™ SP45, PRAESTO™ SP65, or PRAESTO™ SP65, available from Purolite. In some embodiments, the CEX resin used in the purification process can be POROS® XS, available from Thermo Fisher Scientific/Life Technologies. In some embodiments, a CEX ligand for the CEX process is POROS® XS. In some aspects, a CEX ligand for the CEX process is CMM HyperCel™.

Interactions between the ligands and EVs are influenced by several factors, such as cation exchangers, flow rate, particle size of the resin, binding capacity, or any combination thereof. In certain embodiments the present disclosure further provides conditions where EVs can be effectively isolated, purified or sub-fractionated with cation exchange ligands. In some embodiments, the binding of EVs to CEX ligands is strengthened in lower pH. In other embodiments, the pH of the CEX loading buffer is at least about 0.1, at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, or at least about 4.0 lower than the pH of the AEX loading buffer. In other embodiments, the pH of the CEX loading buffer is from about 1 to about 2 lower than the pH of the AEX loading buffer.

In some embodiments, the pH of the CEX loading buffer is from about 5.0 to about 7.0, wherein the pH of the AEX loading buffer is optionally higher than 7. In some embodiments, the pH of the CEX loading buffer is from about 5.1 to about 6.9, wherein the pH of the AEX loading buffer is optionally higher than 6.9. In some embodiments, the pH of the CEX loading buffer is from about 5.2 to about 6.8, wherein the pH of the AEX loading buffer is optionally higher than 6.8. In some embodiments, the pH of the CEX loading buffer is from about 5.3 to about 6.7, wherein the pH of the AEX loading buffer is optionally higher than 6.7. In some embodiments, the pH of the CEX loading buffer is from about 5.4 to about 6.6, wherein the pH of the AEX loading buffer is optionally higher than 6.6. In some embodiments, the pH of the CEX loading buffer is from about 5.5 to about 6.5, wherein the pH of the AEX loading buffer is optionally higher than 6.5. In some embodiments, the pH of the CEX loading buffer is from about 5.6 to about 6.4, wherein the pH of the AEX loading buffer is optionally higher than 6.4. In some embodiments, the pH of the CEX loading buffer is from about 5.7 to about 6.3, wherein the pH of the AEX loading buffer is optionally higher than 6.3. In some embodiments, the pH of the CEX loading buffer is from about 5.8 to about 6.2, herein the pH of the AEX loading buffer is optionally higher than 6.2. In some embodiments, the pH of the CEX loading buffer is from about 5.9 to about 6.2, wherein the pH of the AEX loading buffer is optionally higher than 6.2. In some embodiments, the pH of the CEX loading buffer is from about 6.0 to about 6.2, wherein the pH of the AEX loading buffer is optionally higher than 6.2. In some embodiments, the pH of the CEX loading buffer is about 6.1, wherein the pH of the AEX loading buffer is optionally higher than 6.1. In some embodiments, the pH of the CEX process is from about 7 to about 8, wherein the pH of the AEX loading buffer is optionally higher than 8. In some embodiments, the pH of the CEX loading buffer is from about 7.1 to about 7.9, wherein the pH of the AEX loading buffer is optionally higher than 7.9. In some embodiments, the pH of the CEX loading buffer is from about 7.2 to about 7.8, wherein the pH of the AEX loading buffer is optionally higher than 7.8. In some embodiments, the pH of the CEX loading buffer is from about 7.3 to about 7.7, wherein the pH of the AEX loading buffer is optionally higher than 7.7. In some embodiments, the pH of the CEX loading buffer is from about 7.4 to about 7.6, wherein the pH of the AEX loading buffer is optionally higher than 7.6. In some embodiments the pH of the CEX loading buffer is optionally lower than a neutral pH, e.g., 7.0, wherein the pH of the AEX loading buffer is from about 5.0 to about 10.0, e.g., about 5, about 6, about 7, about 8, about 9, or about 10.

In some embodiments, the binding of EVs to CEX ligands is strengthened in lower salt concentrations. In some embodiments, the CEX loading buffer comprises a salt concentration from about 10 mM to about 300 mM, from about 20 mM to about 300 mM, from about 30 mM to about 250 mM, from about 40 mM to about 200 mM, from about 50 mM to about 150 mM, from about 60 mM to about 150 mM, from about 70 mM to about 150 mM, from about 80 mM to about 150 mM, from about 90 mM to about 150 mM, from about 100 mM to about 150 mM, from about 110 mM to about 150 mM, or from about 120 mM to about 150 mM. In other embodiments, the CEX loading buffer comprises a salt concentration of about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM, about 150 mM, about 155 mM, about 160 mM, about 165 mM, about 170 mM, about 175 mM, about 180 mM, about 185 mM, about 190 mM, or about 200 mM. In some embodiments, the salt concentration of the CEX loading buffer is about 130 mM, about 135 mM, about 137 mM, or about 140 mM.

In some embodiments, the salt concentration of the CEX loading buffer is at least about 100 mM, at least about 150 mM, at least about 200 mM, at least about 250 mM, at least about 300 mM, at least about 350 mM, at least about 400 mM, or at least about 450 mM lower than the salt concentration of the AEX loading buffer and/or the MMC loading buffer. In other embodiments, the salt concentration of the CEX loading buffer is about 100 mM, about 200 mM, or about 300 mM lower than the salt concentration of the AEX loading buffer.

In some embodiments, CEX is performed in a bind-elute mode. In some embodiments, CEX is performed in a flow-through mode. In some embodiments, CEX is performed in a weak-partitioning mode, where the EVs are bound more weakly that impurities which bind more strongly to the CEX resin.

In the weak-partitioning mode, at least some desired EVs and at least some undesired EVs or impurities, both bind to the chromatographic medium. However, undesired EVs or impurities bind more tightly to the medium. Unbound, desired EVs pass through the medium and are recovered from the column effluent. The binding between EVs and the chromatographic medium is intermediate in comparison to bind-elute and flow-through modes.

In some embodiments, a loading phase can be followed by a wash phase to increase recovery of the desired product. Washing can be done with a washing buffer identical to or different from the loading buffer. When different, the wash buffer is different from the loading buffer in terms of composition or pH.

In some embodiments, the pH of the CEX wash buffer is higher than the pH of the CEX loading buffer. In other embodiments, the pH of the CEX wash buffer is the same as the AEX loading buffer. In other embodiments, the pH of the CEX wash buffer is at least about 0.1, at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, or at least about 4.0 lower than the pH of the AEX loading buffer. In other embodiments, the pH of the CEX wash buffer is from about 1 to about 2 lower than the pH of the CEX loading buffer.

In some embodiments, the CEX wash buffer comprises a salt concentration from about 300 mM to about 5M, from about 300 mM to about 4M, from about 300 mM to about 3M, from about 400 mM to about 3M, from about 500 mM to about 3M, from about 600 mM to about 2.5M, from about 700 mM to about 2.5M, from about 800 mM to about 2.5M, from about 900 mM to about 2.5M, from about 1M to about 2.4M, from about 1M to about 2.3M, or from about 1.5M to about 2M. In other embodiments, the CEX wash buffer comprises a salt concentration of about 300 mM, about 400 mM, about 500 mM, about 600 mM, about 700 mM, about 800 mM, about 900 mM, about 1M, about 1.1M, about 1.2M, about 1.3M, about 1.4M, about 1.5M, about 1.6M, about 1.7M, about 1.8M, about 1.9M, about 2.0M, about 2.1M, about 2.2M, about 2.3M, about 2.4M, about 2.5M, about 2.6M, about 2.7M, about 2.8M, about 2.9M, or about 3.0M. In some embodiments, the salt concentration of the CEX wash buffer is about 1M, about 1.5M, about 2.0M, or about 2.5M. In some embodiments, the salt concentration of the CEX wash buffer is about 2M.

In certain embodiments, various weak-partitioning purification methods, well-known in the art, can be combined with the methods disclosed in this application. For example, in some embodiments, methods for identifying ideal conditions for the weak-partitioning mode or purification methods disclosed in the U.S. Publication No. 2007/0060741, which is incorporated by reference in its entirety herein, can be used.

In certain embodiments the CEX process is repeated multiple times. In some embodiments, the CEX process is repeated at least two times, at least three times, at least four times, at least five times, at least six times, at least seven times, at least eight times, at least nine times, at least ten times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, at least 28 times, at least 29 times, at least 30 times, at least 31 times, at least 32 times, at least 33 times, at least 34 times, at least 35 times, at least 36 times, at least 37 times, at least 38 times, at least 39 times, at least 40 times, at least 41 times, at least 42 times, at least 43 times, at least 44 times, at least 45 times, at least 46 times, at least 47 times, at least 48 times, at least 49 times, at least 50 times. In some embodiments, the CEX process is repeated at least three times. In some embodiments, the CEX process is repeated at least four times. In some embodiments, the CEX process is repeated at least five times. In some embodiments, the CEX process is repeated at least six times.

ILB. Anion Exchange Chromatography (AEX) Process

The methods of the present disclosure also include an AEX. AEX is another form of ion exchange chromatography that separates samples based on their surface charge. AEX uses positively charged ligands having affinity to targets having negative surface charges. In some embodiments, the AEX can be performed on the sample comprising EVs after the sample has been subjected to CEX. In other embodiments, the AEX can be performed on the sample comprising EVs before the sample has been subjected to CEX. In some embodiments, the AEX can be performed on the sample comprising EVs before the sample has been subjected to MMC. In some embodiments, the AEX can be performed on the sample comprising EVs after the sample has been subjected to MMC.

In some embodiments, AEX is performed in a weak-partitioning mode. In some embodiments, AEX is performed in flow-through mode. In some embodiments, AEX is performed in a bind-elute mode. In some embodiments, the present methods include a CEX process in a flow-through mode and an AEX process in a bind-elute mode.

In bind-elute mode, desired EVs bind to chromatographic medium and are eluted from the medium by elution buffers. These methods generally comprise the steps of applying or loading a sample comprising EVs, optionally washing away unbound sample components using appropriate buffers that maintain the binding interaction between EVs and affinity ligands and eluting (dissociating and recovering) EVs from the immobilized ligands by altering buffer conditions so that the binding interaction no longer occurs.

In some embodiments, exchange resin can be eluted with a particular elution buffer and selected fractions of the eluate can be concentrated (e.g., by dialysis) to provide an enriched EV preparation. In certain embodiments, the AEX resin used in the scalable method is of a sufficient size to accommodate large scale volumes of conditioned culture media. In other embodiments, a second elution of the collected fractions from a first passage over an anion exchange column can be performed. In some embodiments, the AEX is repeated at least two times, at least three times, at least four times, at least five times, at least six times, at least seven times, at least eight times, at least nine times, at least ten times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, at least 28 times, at least 29 times, at least 30 times, at least 31 times, at least 32 times, at least 33 times, at least 34 times, at least 35 times, at least 36 times, at least 37 times, at least 38 times, at least 39 times, at least 40 times, at least 41 times, at least 42 times, at least 43 times, at least 44 times, at least 45 times, at least 46 times, at least 47 times, at least 48 times, at least 49 times, at least 50 times. In some embodiments, the AEX is repeated at least three times. In some embodiments, the AEX is repeated at least four times. In some embodiments, the AEX is repeated at least five times. In some embodiments, the AEX is repeated at least six times.

AEX resin refers to a solid phase which is positively charged, e.g. having one or more positively charged ligands. In some embodiments, the ligands are selected from diethylaminopropyl, diethylaminoethyl, quaternary aminoethyl, quaternary ammonium, carboxymethyl, carboxylic acid, glutamic acid, aspartic acid, histidine, hydroxyl, phosphate, tertiary amines, quaternary amines, diethaminoethyl, dimethylaminoethyl, trimethylaminoethyl, an amino acid ligand, or combinations thereof. Commercially available anion exchange resins include DEAE cellulose, QAE SEPHADEX and FAST Q SEPHAROSE (Pharmacia). In certain embodiments the chromatography ligands can be bound to a base matrix. In some embodiments, the base matrix can comprise monoliths, hydrogels, porous devices, nanofibers, composite resins, beaded resins, beaded resin with inert porous shells, and/or any other solid or porous support. In some embodiments, the base matrix can comprise cellulose, agarose, polystyrene derivatives, polyvinyl ether, silica, methacrylate derivatives, glass, ceramic hydroxyapatite, acrylamide, and/or other backbones commonly used in chromatography.

Examples of anion exchange resins include, but are not limited to: Q SEPHAROSE™ FF, Q SEPHAROSE™ HP, Q SEPHAROSE™ BB, Q SEPHAROSE™ XL, DEAE SEPHAROSE™ FF, ANX SEPHAROSE™ 4FF low sub, ANX SEPHAROSE™ 4FF high sub, SOURCE™ 15Q, SOURCE™ 30Q, CAPTO™ Q, CAPTO™ DEAE, or CAPTO™ Q ImpRes, available from GE Healthcare; FRACTOGEL® EMD DEAE (M), FRACTOGEL® EMD TMAE (M), FRACTOGEL® EMD TMAE (S), FRACTOGEL® EMD TMAE Hicap (M), FRACTOGEL® EMD TMAE Medcap (M), ESHMUNO® Q or ESHMUNO® Q, available from Merck Millipore; TOYOPEARL® DEAE-650C, TOYOPEARL® DEAE-650M, TOYOPEARL® DEAE-650S, TOYOPEARL® SuperQ-650C, TOYOPEARL® SuperQ-650M, TOYOPEARL® SuperQ-650S, TOYOPEARL® QAE-550C, TOYOPEARL® GIGACAP® Q-650M, TOYOPEARL® Q-600C AR, TOYOPEARL® GIGACAP® DEAE-650M, TOYOPEARL® GIGACAP®

Q-650S, TOYOPEARL® NH2-750F, TSKGEL® SuperQ-5PW (20 μm), or TSKGEL® SuperQ-5PW (30 μm), available from Tosoh Bioscience; MACRO-PREP® DEAE, MACRO-PREP® High Q, MACRO-PREP® 25 Q, UNO-SPHERE™ Q or NUVIA™ Q, available from BioRad Laboratories; Q HYPERCEL™, DEAE Ceramic HYPERD® F, Q Ceramic HYPERD® 20, Q Ceramic HYPERD® F, or HYPERCEL™ STAR AX, available from Pall Corporation; POROS® 50 HQ, POROS® 50 PI, POROS® 50 D, POROS® 20 HQ, or POROS® XQ, available from Thermo Fisher Scientific/Life Technologies; DEAE PuraBead HF, available from Prometic Bioseparations; PL-SAX 1000 Å 30 μm, or PL-SAX 1000 Å 10 μm, available from Agilent Technologies; CELLUFINE® MAX Q-h, or CELLUFINE® Q-500 (m), available from JNC Corporation; BAKERBOND™ POLYQUAT, BAKERBOND™ POLYPEI, or BAKERBOND™ POLYPEI, available from Avantor Pharmaceutical Materials; YMC—BioPro Q30, YMC—BioPro Q75, YMC—BioPro SmartSep Q10, or YMC—BioPro SmartSep Q30, available from YMC; Sartobind Q, available from 8 mm; or PRAESTO™ Q65 or PRAESTO™ Q90, available from Purolite. In some embodiments the AEX resin can be Sartobind Q, available from 8 mm. In some embodiments, an AEX resin for the AEX process is SARTOBIND® Q (8 mm).

In some embodiments, binding of EVs to AEX ligands is strengthened in higher pH compared to the CEX process as described herein. In other embodiments, binding of EVs to AEX ligands is strengthened in lower salt conditions compared to one or more chromatography processes, (e.g., CEX and/or MMC). Accordingly, the methods can further comprise the step of changing (raising or lowering) the salt concentration or pH of the sample before loading the sample to the AEX resin. In some embodiments, the pH and the salt concentration for the AEX process are selected for inducing precipitation of contaminant proteins. In some embodiments, the AEX chromatography is conducted at a pH from about 7 to about 10. In some embodiments, the pH of the AEX loading buffer is from about 7 to about 9, wherein the pH of the CEX loading buffer is optionally lower than 9. In some embodiments, the pH of the AEX loading buffer is from about 7 to about 8, wherein the pH of the CEX loading buffer is optionally lower than 8. In some embodiments, the pH of the AEX loading buffer is from about 7 to about 7.9, wherein the pH of the CEX loading buffer is optionally lower than 7.9. In some embodiments, the pH of the AEX loading buffer is from about 7.1 to about 7.8, wherein the pH of the CEX loading buffer is optionally lower than 7.8. In some the pH of the AEX loading buffer is from about 7.2 to about 7.7, wherein the pH of the CEX loading buffer is optionally lower than 7.7. In some embodiments, the pH of the AEX loading buffer is from about 7.3 and about 7.6, wherein the pH of the CEX loading buffer is optionally lower than 7.6. In some embodiments, the pH of the AEX loading buffer is from about 7.3 to about 7.5, wherein the pH of the CEX loading buffer is optionally lower than 7.5. In some embodiments, the pH of the AEX loading buffer is about 7.4, wherein the pH of the CEX loading buffer is optionally lower than 7.4. In some embodiments, the pH of the AEX loading buffer is from about 5.0 to about 10.0, wherein the pH of the CEX loading buffer is optionally lower than 7.0. In some embodiments, the pH of the AEX process is about the same as the pH of the CEX process.

In some embodiments, the pH of the AEX loading buffer is higher than the CEX loading buffer. In some embodiments, the pH of the AEX loading buffer is at least about 0.1, at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, or at least about 4.0 higher than the pH of the CEX loading buffer. In some embodiments, the pH of the AEX loading buffer is about 7.4.

In some embodiments, the AEX loading buffer comprises a salt concentration from about 10 mM to about 1000 mM, from about 50 mM to about 900 mM, from about 60 mM to about 800 mM, from about 70 mM to about 700 mM, from about 80 mM to about 700 mM, from about 80 mM to about 800 mM, from about 90 mM to about 700 mM, from about 100 mM to about 700 mM, from about 150 mM to about 700 mM, from about 200 mM to about 700 mM, from about 300 mM to about 600 mM, from about 400 mM to about 600 mM, from about 500 mM to about 600 mM, from about 500 mM to about 700 mM, or from about 500 mM to about 800 mM. In some embodiments, the AEX loading buffer comprises a salt concentration of about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 800 mM, about 900 mM, or about 1M.

In some embodiments the AEX elution buffer comprises a salt concentration from about 600 mM to about 1500 mM, from about 700 mM to about 1400 mM, from about 800 mM to about 1300 mM, from about 900 mM to about 1200 mM, from about 800 mM to about 1500 mM, from about 700 mM to about 1500 mM, from about 800 mM to about 1400 mM, from about 600 mM to about 1300 mM, from about 600 mM to about 1400 mM, from about 600 mM to about 1200 mM, from about 600 mM to about 1100 mM, or from about 1000 mM to about 1500 mM.

In other embodiments, the AEX wash buffer comprises a salt concentration from about 1M to about 3M, from about 1M to about 2.9M, from about 1.1M to about 2.9M, from about 1.5M to about 2.5M, from about 1.6M to about 2.4M, from about 1.7M to about 2.3M, from about 1.8M to about 2.2M, or from about 1.9M to about 2.1M. In other embodiments, the AEX wash buffer comprises a salt concentration about 1M, about 1.1M, about 1.2M, about 1.3M, about 1.4M, about 1.5M, about 1.6M, about 1.7M, about 1.8M, about 1.9M, about 2.0M, about 2.1M, about 2.2M, about 2.3M, about 2.4M, about 2.5M, about 2.6M, about 2.7M, about 2.8M, about 2.9M, or 3.0M. In some embodiments, the AEX wash buffer comprises a salt concentration about 2M.

II.C. Multi-Modal Chromatography (MMC)

In some embodiments, samples comprising EVs are purified by mixed mode chromatography ("MMC", "the MMC process"). In some embodiments, samples comprising EVs are purified by MMC after being purified by AEX. In some embodiments, samples comprising EVs are purified by MMC before being purified by AEX. In some embodiments, samples comprising EVs are purified by MMC after being purified by CEX. In some embodiments, samples comprising EVs are purified by MMC before being purified by CEX. In some embodiments, samples purified by AEX or CEX are processed by depth filtration before further being processed by MMC. In some embodiments, adsorptive depth filter is used. In some embodiments, an AEX-processed sample further processed by depth filtration is applied to MMC for purification.

Mixed mode chromatography employs chromatographic resins containing ligands possessing more than one type of functional groups. This unique property of mixed mode resin enables binding through multiple chromatographic modes in a single resin. Most resins in this class comprise a ligand containing a hydrophobic group (e.g. phenyl, benzyl, propyl, butyl, etc.) and a charged group (e.g. cation: sulfate, carboxylic acid, methyl carboxylic acid; or an anion: quaternary amine, diethylaminoethyl, diethylaminopropyl, or quaternary ammonium). However, some resins may also contain a hydrophilic group in place of the hydrophobic group, (e.g. silica, urea, polyethyleneimine, amino or amide groups, cyanopropyl, diol, or aminopropyl).

In some embodiments, MMC resins can comprise conventional chromatography ligands. In some embodiments, the ligands are selected from tertiary amines, quaternary amines, diethaminoethyl, ceramic hydroxyapatite, ceramic fluoroapatite, butyl, hexyl, ether, hydroxyl, polypropylene glycol, phenyl, benzyl, sulfate, sulfopropyl, sulfobutyl, sulfoisobutyl, sulfoethyl, sulfonate, sulfonic acid, carboxymethyl, carboxylic acid, glutamic acid, aspartic acid, histidine, hydroxyl, phosphate ligands, and mixtures thereof. In some embodiments, the chromatography ligands are formulated as CAPTO™ MMC, CAPTO™ adhere, CAPTO™ MMC ImpRes, CAPTO™ adhere ImpRes, CAPTO™ Core 700, or CAPTO™ Core 700, available from GE Healthcare; ESHMUNO® HCX, available from Merck Millapore; TOYOPEARL® MX-Trp-650M, available from Tosoh Bioscience; NUVIA™ CPRIME™, available from BioRad Laboratories; or CMM HYPERCEL™, HEA HYPERCEL™ or PPA HyperCel™, available from Pall Corporation; In some embodiments, the MMC resin can be a resin used in other types of chromatography (i.e., AEX, CEX, HIC, HCIC, etc.). In some embodiments, the MMC resin can be CMM HYPERCEL™, available from Pall Corporation.

In some embodiments, the resins used in MMC comprise anion-exchange/reversed-phase (AEX/RP), cation-exchange/reversed phase (CEX/RP), anion-exchange/cation-exchange/reversed phase (AEX/CEX/RP), AEX/hydrophilic (AEX/HILIC), CEX-hydrophilic (CEX/HILIC), or AEX/CEX hydrophilic (AEX/CEX/HILIC). An example of AEX/RP ligand is a hydrophobic, anionic ligand with hydrogen bonding that contains a quaternary amine, a phenyl group, and allows hydrogen bonding. An example of a CEX/RP ligand is a cationic ligand with hydrophobic binding that contain a secondary amine and is cationic over a wide pH range. Some mixed mode ligands are pH controllable, such as those containing 4-mercaptoethylpyridine ligands. The uncharged nitrogen in the pyridine ring becomes charged as pH decreases, resulting in a pH controllable mixed-mode ligand.

In some embodiments, mixed mode ligands can be immobilized on the base matrix. In some embodiments, the base matrix comprises membranes, monoliths, beaded resins, nanofibers, and/or other absorptive or convective media. In some embodiments, the base matrix comprises cellulose, agarose, polystyrene derivatives, silica, methacrylate derivatives, glass, ceramic hydroxyapatite, PVDF, PTFE, polyethersulfone, polypropylene, polyethylene, acrylamide, and/or any mixtures or derivatives thereof.

Mixed mode media comprising a single or plurality of ligands and a base matrix can be classified into four categories based on the arrangement of the ligand substrates on the base matrix. Type I media are mixtures of separation media, each with a single chemistry, packed to form a column. Type II media comprise substrates modified with a mixture of ligands having different functionalities, such as ion exchange, reverse phase, or hydrophilic phase properties. In Type III media, the functional ligands can be "embedded" in a hydrophobic chain, or in Type IV media, the hydrophobic chain can be "tipped" with the functional group. The mixed mode resins comprising a base matrix and one or more functional groups may be comprised of any of the types of media as described herein.

In some embodiments, a MMC chromatography column is generated with the resin disclosed herein. The resin can be formed in a suspension, in slurry, or can be packed into a chromatography column.

In some embodiments, the MMC chromatography column can further comprise conventional chromatography ligands selected from sulfate, tertiary amines, quaternary amines, carboxy methyl, carboxylic acids, diethaminoethyl, ceramic hydroxy apatite and ceramic fluoroapatite, or any combination thereof. In some embodiments, conventional chromatography ligands can be formulated as CAPTO MMC™ or CAPTO ADHERE™ available from GE Healthcare Life Sciences; TOYOPEARL MX-TRP™ available from Tosoh Bioscience; HYPERCEL™ STAR AX available from Pall Corporation; NUVIA™ CPRIME™ available from BioRad; or ESHMUNO™ HCX available from EMD Millepore.

In some embodiments, hydrophobic, hydrophilic, and/or ionic mixed mode ligands and the conventional chromatography ligands are displayed on the same resin. For example, the hydrophobic, hydrophilic, and/or ionic mixed mode ligands and the conventional chromatography ligands are immobilized on the base matrix (e.g., membranes, monoliths, beaded resins, nanofibers, and other absorptive or convective media). In some embodiments, hydrophobic, hydrophilic, and/or ionic mixed mode ligands and chromatographic ligands are intermixed. In some embodiments, hydrophobic, hydrophilic, and/or ionic mixed mode ligands and chromatographic ligands are displayed on separate layers.

In some embodiments, mixed mode media comprises hydrophobic ligands. Hydrophobic ligands can be used to purify EVs based on their interaction with a nonpolar surface on EVs, an amphiphilic phospholipid bilayer membrane with embedded transmembrane proteins or an outer bilayer surface that is associated with a variety of proteins, nucleic acids, lipids, and carbohydrates. Hydrophobic groups of the biomolecules that are sufficiently exposed to the surface allow interaction with hydrophobic ligands. In some embodiments, the hydrophobic ligands can be hydrophobic alkyl or aryl groups. In some embodiments, the hydrophobic alkyl or aryl groups are selected from phenyl, ethyl, methyl, pentyl, heptyl, benzyl, octyl, butyl, hexyl, ether, hydroxyl, polypropylene glycol, and the like.

In some embodiments, mixed mode media comprises hydrophilic ligands. Hydrophilic ligands can be used to purify EVs via flow through mode, or to purify desired subgroups of EVs. The amphiphilic surface of the EVs may not bind to the hydrophilic ligands of the column, while polar impurities or proteins in the sample interact with the hydrophilic ligands. In some embodiments, the hydrophilic ligands comprise, silica, urea, amino groups, amide groups, polyethyleneimine, cyanopropyl, diol, aminopropyl, and/or zwitterions such as sulnfoalkylbetaine.

In some embodiments, mixed mode media comprises CEX ligands.

In some embodiments, mixed mode media comprises AEX ligands.

In some embodiments, MMC chromatography is performed in a bind-elute mode. In some embodiments, MMC chromatography is performed in a weak-partitioning mode.

According to the present disclosure, additional chromatography process can be used in addition to the chromatography processes disclosed herein (e.g., CEX-AEX or CEX-AEX-MMC). In some embodiments, the additional chromatography can be used instead of the MMC process. In other embodiments, the additional chromatography can be used in addition to the CEX, AEX, and MMC. In some aspects, a CEX, such as a CMM HYPERCEL™ chromatography column, is operated in series with a MMC, such as a CaptoCore700™ column, operated in flowthrough mode. In some aspects, a CEX-MMC is operated in series in flow-through mode. In some embodiments, a MMC-CEX is operated in series in flow-through mode.

In some embodiments, the present method further comprises hydrophobic interaction chromatography ("HIC"). In some embodiments, the present method further comprises hydrophobic charge induction chromatography ("HCIC")

The HIC or HCIC uses hydrophobic ligands attached to a base matrix. In some embodiments the base matrix comprises membranes, monoliths, beaded resins, nanofibers, and/or other absorptive or convective media. In some embodiments, the base matrix comprises cellulose, agarose, polystyrene derivatives, silica, methacrylate derivatives, glass, ceramic hydroxyapatite, PVDF, PTFE, polyethersulfone, polypropylene, polyethylene, acrylamide, and/or any mixtures or derivatives thereof.

Purification of EVs by hydrophobic ligands is based on the interaction between the ligands and a nonpolar surface on EVs, an amphiphilic phospholipid bilayer membrane with embedded transmembrane proteins or an outer bilayer surface that is associated with a variety of proteins, nucleic acids, lipids, and carbohydrates. Hydrophobic groups of the biomolecules that are sufficiently exposed to the surface can interact with hydrophobic ligands.

In some embodiments, hydrophobic ligands that can be used for the present invention include ligands comprising hydrophobic alkyl and/or aryl groups. In some embodiments the hydrophobic alkyl or aryl group are selected from phenyl, ethyl, methyl, pentyl, heptyl, benzyl, octyl, butyl, hexyl, ether, hydroxyl, polypropylene glycol, and mixtures thereof.

In some embodiments, the salt concentration of the MMC loading buffer, elution buffer, and/or wash buffer is at least about 100 mM, at least about 200 mM, at least about 300 mM, at least about 400 mM, at least about 500 mM, at least about 600 mM, at least about 700 mM, at least about 800 mM, at least about 900 mM, at least about 1M, at least about 1.1M, at least about 1.2M, at least about 1.3M, at least about 1.4M, at least about 1.5M, at least about 1.6M, at least about 1.7M, at least about 1.8M, at least about 1.9M, at least about 2.0M, at least about 2.1M, at least about 2.2M, at least about 2.3M, at least about 2.4M, or at least about 2.5M. In other embodiments, the sale concentration of the MMC loading buffer is between about 10 mM and about 5M, between about 100 mM and about 5M, between about 100 mM and about 4M, between about 100 mM and about 3M, between about 200 mM and about 5M, between about 300 mM and about 4M, between about 400 mM and about 3M, between about 500 mM and about 2M, between about 1M and about 3M, between about 1 mM and about 2M, between about 800 mM and about 2M, between about 900 mM and about 2.5M, or between about 1.5M and about 2.5M. In some embodiments, the salt concentration of the MMC loading buffer and wash buffer is about 1M.

In some embodiments, the pH of the MMC loading buffer and/or wash buffer is the same as that of the AEX loading buffer and/or wash buffer. In some embodiments, the pH of the MMC loading buffer is lower than the AEX loading buffer. In some embodiments, the pH of the MMC loading buffer is at least about 0.1, at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, or at least about 4.0 lower than the pH of the AEX loading buffer.

In some embodiments, the pH of the MMC loading buffer is different from the pH of the AEX loading buffer, e.g., higher than the AEX loading buffer. In some embodiments, the pH of the MMC loading buffer is at least about 0.1, at least about 0.2, at least about 0.3, at least about 0.4, at least about 0.5, at least about 0.6, at least about 0.7, at least about 0.8, at least about 0.9, at least about 1.0, at least about 1.1, at least about 1.2, at least about 1.3, at least about 1.4, at least about 1.5, at least about 1.6, at least about 1.7, at least about 1.8, at least about 1.9, at least about 2.0, at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, or at least about 4.0 higher than the pH of the AEX loading buffer. In some embodiments, the pH of the MMC loading buffer and/or wash buffer is about 7.5.

II.D. Filtration Between Chromatography

In some embodiments, one or more filtration steps are added between the chromatographic purification steps. For example, adsorptive depth filtrations step can be added before, between, or after chromatographic steps: (i) Filtration-CEX-AEX-MMC; (ii) CEX-Filtration-AEX-MMC; (iii) CEX-AEX-Filtration-MMC; (iv) CEX-AEX-MMC-filtration; (v) Filtration-CEX-MMC-AEX; (vi) CEX-Filtration-MMC-AEX; (vii) CEX-MMC-Filtration-AEX; (viii) CEX-MMC-AEX-Filtration; (ix) Filtration-AEX-CEX-MMC; (x) AEX-Filtration-CEX-MMC; (xi) AEX-CEX-Filtration-MMC; (xii) AEX-CEX-MMC-Filtration; (xiii) Filtration-AEX-MMC-CEX; (xiv) AEX-Filtration-MMC-CEX; (xv) AEX-MMC-Filtration-CEX; (xvi) AEX-MMC-CEX-Filtration; (xvii) Filtration-MMC-CEX-AEX; (xvii) MMC-Filtration-CEX-AEX; (xvii) MMC-CEX-Filtration-AEX; (xvii) MMC-CEX-AEX-Filtration; (xviii) Filtration-MMC-AEX-CEX; (xix) MMC-Filtration-AEX-CEX; (xx) MMC-AEX-Filtration-CEX; or (xxi) MMC-AEX-CEX-Filtration. Any one of filtration described herein can be used for the filtration. In some embodiments, the present method comprises: (1) Filtration(1)-CEX-Filtration(2)-AEX-MMC; (2) Filtration(1)-CEX-AEX-Filtration(2)-MMC; (3) Filtration(1)-CEX-AEX-MMC-Filtration(2); (4) CEX-Filtration(1)-AEX-Filtration(2)-MMC; (5) CEX-Filtration(1)-AEX-MMC-Filtration(2); (6) CEX-AEX-Filtration(1)-MMC-Filtration(2); (7) Filtration(1)-CEX-Filtration(2)-MMC-AEX; (8) Filtration(1)-CEX-MMC-Filtration(2)-AEX; (9)

Filtration(1)-CEX-MMC-AEX-Filtration(2); (10) CEX-Filtration(1)-MMC-Filtration(2)-AEX; (11) CEX-Filtration(1)-MMC-AEX-Filtration(2); (12) CEX-MMC-Filtration(1)-AEX-Filtration(2); (13) Filtration(1)-AEX-Filtration(2)-CEX-MMC; (14) Filtration(1)-AEX-CEX-Filtration(2)-MMC; (15) Filtration(1)-AEX-CEX-MMC-Filtration(2); (16) AEX-Filtration(1)-CEX-Filtration(2)-MMC; (17) AEX-Filtration(1)-CEX-MMC-Filtration(2); (18) AEX-CEX-Filtration(1)-MMC-Filtration(2); (19) Filtration(1)-AEX-Filtration(2)-MMC-CEX; (20) Filtration(1)-AEX-MMC-Filtration(2)-CEX; (21) Filtration(1)-AEX-MMC-CEX-Filtration(2); (22) AEX-Filtration(1)-MMC-Filtration(2)-CEX; (23) AEX-Filtration(1)-MMC-CEX-Filtration(2); (24) AEX-MMC-Filtration(1)-CEX-Filtration(1); (25) Filtration(1)-MMC-Filtration(2)-CEX-AEX; (26) Filtration(1)-MMC-CEX-Filtration(2)-AEX; (27) Filtration(1)-MMC-CEX-AEX-Filtration(2); (28) MMC-Filtration(1)-CEX-Filtration(2)-AEX; (29) MMC-Filtration(1)-CEX-AEX-Filtration(2); (30) MMC-CEX-Filtration(1)-AEX-Filtration(2); (31) Filtration(1)-MMC-Filtration(2)-AEX-CEX; (32) Filtration(1)-MMC-AEX-Filtration(2)-CEX; (33) Filtration(1)-MMC-AEX-CEX-Filtration(2); (34) MMC-Filtration(1)-AEX-CEX-Filtration(2)-CEX; (35) MMC-Filtration(1)-AEX-CEX-Filtration(2); or (36) MMC-AEX-Filtration(1)-CEX-Filtration(2). In some embodiments, Filtration (1) is the same as Filtration (2). In other embodiments, Filtration (1) is different from Filtration (2). In other embodiments, any filtration prior to the CEX process has a bigger filter size compared to a filter size of filtration after the CEX process. In some embodiments, the filter size of the filtrations is reduced in or after the CEX process. In some embodiments, the filter size prior to the CEX process is bigger than about 0.14 micron, about 0.16 micron, about 0.18 micron, about 0.2 micron, about 0.25 micron, about 0.3 micron, about 0.35 micron, about 0.4 micron, about 0.45 micron, about 0.5 micron, about 0.55 micron, about 0.6 micron, about 0.65 micron, or about 0.7 micron. In other embodiments, the filter size of the filtrations in or after the CEX process is smaller than about 0.25 micron, about 0.22 micron, about 0.2 micron, about 0.18 micron, about 0.16 micron, or about 0.14 micron. In some aspects, the method of the disclosure comprises AEX-Filtration-CEX-MMC.

In some embodiments, the present method comprises: (1) Filtration(1)-CEX-Filtration(2)-AEX-Filtration(3)-MMC; (2) Filtration(1)-CEX-Filtration(2)-AEX-MMC-Filtration(3); (3) Filtration(1)-CEX-AEX-Filtration(2)-MMC-Filtration(3); (4) CEX-Filtration(1)-AEX-Filtration(2)-MMC-Filtration(3); (5) Filtration(1)-CEX-Filtration(2)-MMC-Filtration(3)-AEX; (6) Filtration(1)-CEX-Filtration(2)-MMC-AEX-Filtration(3); (7) Filtration(1)-CEX-MMC-Filtration(2)-AEX-Filtration(3); (8) CEX-Filtration(1)-MMC-Filtration(2)-AEX-Filtration(3); (9) Filtration(1)-AEX-Filtration(2)-CEX-Filtration(3)-MMC; (10) Filtration(1)-AEX-Filtration(2)-CEX-MMC-Filtration(3); (11) Filtration(1)-AEX-CEX-Filtration(2)-MMC-Filtration(3); (12) AEX-Filtration(1)-CEX-Filtration(2)-MMC-Filtration(3); (13) Filtration(1)-AEX-Filtration(2)-MMC-Filtration(3)-CEX; (14) Filtration(1)-AEX-Filtration(2)-MMC-CEX-Filtration(3); (15) Filtration(1)-AEX-MMC-Filtration(2)-CEX-Filtration(3); (16) AEX-Filtration(1)-MMC-Filtration(2)-CEX-Filtration(3); (17) Filtration(1)-MMC-Filtration(2)-CEX-Filtration(3)-AEX; (18) Filtration(1)-MMC-Filtration(2)-CEX-AEX-Filtration(3); (19) Filtration(1)-MMC-CEX-Filtration(2)-AEX-Filtration(3); (20) MMC-Filtration(1)-CEX-Filtration(2)-AEX-Filtration(3); (21) Filtration(1)-MMC-Filtration(2)-AEX-Filtration(3)-CEX; (22) Filtration(1)-MMC-Filtration(2)-AEX-CEX-Filtration(3); (23) Filtration(1)-MMC-AEX-Filtration(2)-CEX-Filtration(3); (24) MMC-Filtration(1)-AEX-Filtration(2)-CEX-Filtration(3). In some aspects, the method comprises Filtration (1)-AEX-Filtration (2)-CEX-MMC-Filtration (3). In other embodiments, any filtration prior to the CEX process has a bigger filter size compared to a filter size of filtration after the CEX process. In some embodiments, the filter size of the filtrations is reduced in or after the CEX process. In some embodiments, the filter size prior to the CEX process is bigger than about 0.25 micron, about 0.3 micron, about 0.35 micron, about 0.4 micron, about 0.45 micron, about 0.5 micron, about 0.55 micron, about 0.6 micron, about 0.65 micron, or about 0.7 micron. In other embodiments, the filter size of the filtrations in or after the CEX process is smaller than about 0.25 micron, about 0.22 micron, about 0.2 micron, about 0.18 micron, about 0.16 micron, or about 0.14 micron.

In some embodiments, the present method comprises: (1) Filtration(1)-CEX-Filtration(2)-AEX-Filtration(3)-MMC-Filtration(4); (2) Filtration(1)-CEX-Filtration(2)-MMC-Filtration(3)-AEX-Filtration(4); (3) Filtration(1)-AEX-Filtration(2)-CEX-Filtration(3)-MMC-Filtration(4); (4) Filtration (1)-AEX-Filtration(2)-MMC-Filtration(3)-CEX-Filtration (4); (5) Filtration(1)-MMC-Filtration(2)-CEX-Filtration(3)-AEX-Filtration(4); or (6) Filtration(1)-MMC-Filtration(2)-AEX-Filtration(3)-CEX-Filtration(4). In other embodiments, any filtration prior to the CEX process has a bigger filter size compared to a filter size of filtration in or after the CEX process. In some embodiments, the filter size of the various filtrations is reduced in or after the CEX process. In some embodiments, the filter size prior to the CEX process is bigger than about 0.25 micron, about 0.3 micron, about 0.35 micron, about 0.4 micron, about 0.45 micron, about 0.5 micron, about 0.55 micron, about 0.6 micron, about 0.65 micron, or about 0.7 micron. In other embodiments, the filter size of the filtrations in or after the CEX process is smaller than about 0.25 micron, about 0.22 micron, about 0.2 micron, about 0.18 micron, about 0.16 micron, or about 0.14 micron. In some aspects, the present filtration useful in the process is a sterile filtration. One or more sterile filtrations can be performed within the present methods. In some aspects, at least one, at least two, at least three, at least four, at least five, at least six, at least seven, at least eight, at least nine, at least ten, at least 11, at least 12, at least 13, at least 14, or at least 15 filtrations can be introduced in the present methods. In some aspects, a sterile filtration can be introduced between two chromatographies. In some aspects, filtration can be used right after the harvest, In other aspects, filtration can be used right before formulation.

III. Samples Comprising EVs

Samples comprising EVs useful for the present methods can be obtained from a various in vitro cell culture or a harvest or a supernatant of the cell culture. In some embodiments, the sample comprising EVs can be obtained from a mammalian cell, a bacterial cell, a eukaryotic cell, a prokaryotic cell, a plant cell, an insect cell, or any combination thereof. In some embodiments, the sample comprising EVs can be obtained from a mammalian cell. In some embodiments, the sample comprising EVs can be obtained from a HEK cell culture. In some embodiments, the sample comprising EVs can be a cell culture comprising cells producing EVs.

The present disclosure provides a method for preparing EVs, which can be implemented to purify EVs in a large scale. In some embodiments, the method can be applied to purify EVs from a sample with a volume larger than about 1 L, about 5 L, about 10 L, about 15 L about 20 L, about 25 L, about 50 L, about 100 L, about 200 L, about 250 L, about 300 L, about 400 L, about 500 L, about 600 L, about 700 L, about 800 L, about 900 L, about 1000 L, or about 2000 L. In some embodiments, the method can be applied to purify EVs from a sample with a volume of about 400 L. In some embodiments, the method can be applied to purify EVs from a sample with a volume of about 500 L. In some embodiments, the method can be applied to purify EVs from a sample with a volume of about 600 L. In some embodiments, the method can be applied to purify EVs from a sample with a volume larger than about 100 L. In some embodiments, the method can be applied to purify EVs from a sample with a volume larger than about 200 L. In some embodiments, the method can be applied to purify EVs from a sample with a volume larger than about 300 L. In some embodiments, the method can be applied to purify EVs from a sample with a volume larger than about 700 L. In some aspects, the method can be applied to purify EVs from a sample with a volume larger than about 1000 L. In some aspects, the method can be applied to purify EVs from a sample with a volume larger than about 1500 L. In some aspects, the method can be applied to purify EVs from a sample with a volume larger than about 2000 L.

In some aspects, the cell culture media useful for the present methods comprises 3D suspension culture comprising high-depth chemically defined media. In some aspects, the method of the present disclosure includes continuous manufacturing processes. In some aspects, the methods comprise continuous manufacturing processes at high cell density (e.g., at least about $50\times10^6$ cells/ml, at least about $60\times10^6$ cells/ml, at least about $70\times10^6$ cells/ml, at least about $80\times10^6$ cells/ml, at least about $90\times10^6$ cells/ml, at least about $100\times10^6$ cells/ml, at least about $110\times10^6$ cells/ml, at least about $120\times10^6$ cells/ml, at least about $130\times10^6$ cells/ml, at least about $140\times10^6$ cells/ml, at least about $150\times10^6$ cells/ml, at least about $200\times10^6$ cells/ml, at least about $250\times10^6$ cells/ml, at least about $300\times10^6$ cells/ml, at least about $350\times10^6$ cells/ml, or at least about $400\times10^6$ cells/ml, e.g., $40\times10^6$ to $200\times10^6$ cell/ml, e.g., $50\times10^6$ to $170\times10^6$ cell/ml, e.g., $50\times10^6$ to $150\times10^6$ cell/ml).

In some embodiments, each sample has a volume of about 500 L and the 500 L volume sample goes through the purification step (e.g., CEX and AEX, CEX, AEX, and MMC, or any other combinations) as described herein. In other embodiments, the total amount of sample that goes through the purification step for each batch is at least about 5,000 L, at least about 6,000 L, at least about 7,000 L, at least about 8,000 L, at least about 9,000 L, at least about 10,000 L, at least about 11,000 L, at least about 12,000 L, at least about 13,000 L, at least about 14,000 L, or at least about 15,000 L. In other embodiments, the total amount of sample that goes through the purification step for each batch is at least about 10,000 L. In other embodiments, the total amount of sample that goes through the purification step for each batch is at least about 15,000 L. In other embodiments, the total amount of sample that goes through the purification step for each batch is at least about 20,000 L.

In some embodiments, the EVs that can be purified by the present methods comprise naturally-occurring EVs, e.g., exosomes. In some embodiments, the EVs that can be purified by the present methods comprise engineered EVs, e.g., exosomes. In some embodiments, the EVs that can be purified by the present methods comprise surface-engineered EVs, e.g., exosomes. In some embodiments, the EVs that can be purified by the present methods comprise engineered EVs, e.g., exosomes that contain one or more (heterologous) moieties in the lumen of the EVs, e.g., exosomes (e.g., encapsulated in the EVs). In some embodiments, the EVs that can be purified by the present methods comprise engineered EVs that contain one or more (heterologous) moieties linked to a moiety on the exterior surface of the EVs. In some embodiments, the EVs that can be purified by the present methods comprise engineered EVs that contain one or more (heterologous) moieties linked to a moiety on the luminal surface of the EVs.

In other embodiments, the EVs from the producer cell can have a longest dimension of from about 20 to about 1000 nm. In some embodiments, the EVs from the producer cell can have a longest dimension of from about 20 to about 900 nm, from about 20 to about 800 nm, from about 20 to about 700 nm, from about 20 to about 600 nm, from about 20 to about 500 nm, from about 20 to about 400 nm, from about 20 to about 350 nm, from about 20 to about 300 nm, from about 20 to about 290 nm, from about 20 to about 280 nm, from about 20 to about 270 nm, from about 20 to about 260 nm, from about 20 to about 250 nm, from about 20 to about 240 nm, from about 20 to about 230 nm, from about 20 to about 220 nm, from about 20 to about 210 nm, from about 20 to about 200 nm, from about 20 to about 190 nm, from about 20 to about 180 nm, from about 20 to about 170 nm, about 20 to about 160 nm, from about 20 to about 150 nm, from about 20 to about 140 nm, about 20 to about 130 nm, from about 20 to about 120 nm, In some embodiments, the EVs from the producer cell can have a longest dimension of from about 20 to about 110 nm, from about 20 to about 100 nm, from about 20 to about 90 nm, In some embodiments, the EVs from the producer cell can have a longest dimension of from about 20 to about 80 nm, from about 20 to about 70 nm, from about 20 to about 60 nm, from about 20 to about 50 nm, from about 20 to about 40 nm, from about 20 to about 30 nm, from about 30 to about 300 nm, from about 30 to about 290 nm, from about 30 to about 280 nm, from about 30 to about 270 nm, from about 30 to about 260 nm, from about 30 to about 250 nm, from about 30 to about 240 nm, from about 30 to about 230 nm, from about 30 to about 220 nm, about 30 to about 210 nm, from about 30 to about 200 nm, from about 30 to about 190 nm, from about 30 to about 180 nm, from about 30 to about 170 nm, from about 30 to about 160 nm, from about 30 to about 150 nm, from about 30 to about 140 nm, from about 30 to about 130 nm, from about 30 to about 120 nm, from about 30 to about 110 nm, from about 30 to about 100 nm, from about 30 to about 90 nm, from about 30 to about 80 nm, from about 30 to about 70 nm, or from about 30 to about 60 nm.

In some embodiments, EV membranes comprise lipids and/or fatty acids. In some embodiments, EV membranes comprise phospholipids, glycolipids, fatty acids, sphingolipids, phosphoglycerides, sterols, cholesterols, and/or phosphatidylserines. In some of these embodiments, EV membranes further comprise one or more polypeptides and/or one or more polysaccharides, such as glycan.

In some embodiments, EV membranes comprise one or more molecules derived from the producer cell. In some embodiments, EVs can be generated in a cell culture system and isolated from the producer cell. In some embodiments, EVs can be generated from a perfusion cell culture. In some embodiments, EVs can be generated from a batch cell culture. In some embodiments, EVs can be generated from a fed batch cell culture. In some embodiments, EVs can be generated from suspension or adherent cells. In some embodiments, EVs can be generated from a HEK293 cell, a CHO cell, a BHK cell, a PERC6 cell, a Vero cell, a HeLa cell, a sf9 cell, a PC12 cell, a mesenchymal stem cell, a human donor cell, a stem cell, a dendritic cell, an antigen presenting cell, an induced pluripotent stem cell (IPC), a differentiated cell, bacteria, *Streptomyces*, *Drosophila*, *Xenopus* oocytes, *Escherichia coli*, *Bacillus subtilis*, yeast, *S. cerevisiae*, *Picchia pastoris*, filamentous fungi, *Neurospora crassa*, and/or *Aspergillus nidulans*. In some embodiments, the producer cell is a HEK293 cell. The process of EV generation would be generally applicable to bioreactor formats including AMBR, shake flasks, SUBS, Waves, Applikons, stirred tanks, CSTRs, adherent cell culture, hollow fibers, iCELLis, microcarriers, and other methods known to those of skill in the art.

The present disclosure also includes extracellular vesicles (EVs) produced by a cell line. The production of extracellular vesicles and maintenance of cell culture conditions are important to maintain viable cell density of a cell culture process and consistently produce high-quality extracellular vesicles over the full length of a cell culture process. In some embodiments, the EVs purified by the present methods are produced in a bioreactor. In some embodiments, the EVs purified by the present methods are produced in a single-use bioreactor. In some embodiments, the EVs purified by the present methods are produced in a perfusion bioreactor. In some embodiments, the EVs purified by the present methods are produced in an alternating tangential flow filtration (ATF) perfusion bioreactor. In some embodiments, the EVs purified by the present methods are produced in a tangential flow filtration (TFF) perfusion bioreactor. In some embodiments, the EVs purified by the present methods are produced in a bioreactor at a viable cell density (VCD) of about $1\times10^6$ cells/mL, about $5\times10^6$ cells/mL, about $10\times10^6$ cells/mL, about $20\times10^6$ cells/mL, about $30\times10^6$ cells/mL, about $40\times10^6$ cells/mL, about $50\times10^6$ cells/mL, or about $60\times10^6$ cells/mL. In some embodiments, the EVs purified by the present methods are produced in a bioreactor at a viable cell density (VCD) of about $60\times10^6$ cells/mL. In some embodiments, the EVs purified by the present methods are produced in a bioreactor at a viable cell density (VCD) of about $50\times10^6$ cells/mL. In some embodiments, the EVs purified by the present methods are produced in a bioreactor at a viable cell density (VCD) of from about 0 to about $60\times10^6$ cells/mL, from about $1\times10^6$ cells/mL to about $60\times10^6$ cells/mL, from about $40\times10^6$ cells/mL to about $60\times10^6$ cells/mL, or from about $50\times10^6$ cells/mL to about $60\times10^6$ cells/mL.

In some embodiments, the EVs purified by the present methods are produced in a bioreactor for about 5 days, about 10 days, about 15 days, about 20 days, about 25 days, or about 30 days. In some embodiments, the EVs purified by the present methods are produced in a bioreactor for about 1-30 days, about 1-45 days, about 1-60 days, about 1-10 days, about 5-10 days, or about 1-25 days. In some embodiments, the EVs purified by the present methods are produced in a bioreactor for about 1-30 days.

In some other embodiments, EVs are modified by altering components of the membrane of the EV. In some of these embodiments, EVs are modified by altering the protein, lipid and/or glycan content of the membrane. In other embodiments, EVs are engineered to express a scaffold moiety, e.g., Scaffold X, Scaffold Y, or any other moieties. In some embodiments, EVs are engineered to express a higher number of one or more proteins naturally expressed on the surface of producer cells or EVs.

In some embodiments, the producer cells naturally contain one or more polypeptides, and EVs derived from the producer cell also contain the one or more polypeptides. In some embodiments, the producer cells are modified to contain one or more polypeptides. In some embodiments, the modification comprises modulating expression of the one or more polypeptides through use of agents that alter endogenous gene expression. In some embodiments, the modification comprises modulating expression of the one or more polypeptides through introduction of expression constructs or mRNAs that encode the one or more polypeptides. In some embodiments, EVs produced by these cells include the one or more polypeptides as a payload.

In some aspects, the payload comprises an adjuvant. Non-limiting examples of adjuvants that can be used with the present disclosure include: Stimulator of Interferon Genes (STING) agonist, a toll-like receptor (TLR) agonist, an inflammatory mediator, RIG-I agonists, alpha-gal-cer (NKT agonist), heat shock proteins (e.g., HSP65 and HSP70), C-type lectin agonists (e.g., beta glucan (Dectin 1), chitin, and curdlan), and combinations thereof.

In some aspects, the payload comprises a cytokine or a binding partner of a cytokine. In some aspects, the cytokine is selected from (i) common gamma chain family of cytokines; (ii) IL-1 family of cytokines; (iii) hematopoietic cytokines; (iv) interferons (e.g., type I, type II, or type III); (v) TNF family of cytokines; (vi) IL-17 family of cytokines; (vii) damage-associated molecular patterns (DAMPs); (viii) tolerogenic cytokines; or (ix) combinations thereof. In certain aspects, the cytokine comprises IL-2, IL-4, IL-7, IL-10, IL-12, IL-15, IL-21, IFN-γ, IL-1α, IL-1β, IL-1ra, IL-18, IL-33, IL-36α, IL-36β, IL-36γ, IL-36ra, IL-37, IL-38, IL-3, IL-5, IL-6, IL-11, IL-13, IL-23, granulocyte-macrophage colony stimulating factor (GM-CSF), granulocyte-colony stimulating factor (G-CSF), leukemia inhibitory factor (LIF), stem cell factor (SCF), thrombopoietin (TPO), macrophage-colony stimulating factor (M-CSF), erythropoietin (EPO), Flt-3, IFN-α, IFN-β, IFN-γ, IL-19, IL-20, IL-22, IL-24, TNF-α, TNF-β, BAFF, APRIL, lymphotoxin beta (TNF-γ), IL-17A, IL-17B, IL-17C, IL-17D, IL-17E, IL-17F, IL-25, TSLP, IL-35, IL-27, TGF-β, or combinations thereof.

In some aspects, the payload comprises a chemokine. In certain aspects, chemokine comprises a (i) CC chemokine (e.g., CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28); (ii) CXC chemokine (e.g., CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17); (iii) C chemokine (e.g., XCL1, XCL2); (iv) CX3C chemokine (e.g., CX3CL1); (v) or combinations thereof. In some aspects, the payload is IL-12.

In some aspects, a payload is a TLR agonist. Non-limiting examples of TLR agonists include: TLR2 agonist (e.g., lipoteichoic acid, atypical LPS, MALP-2 and MALP-404, OspA, porin, LcrV, lipomannan, GPI anchor, lysophosphatidylserine, lipophosphoglycan (LPG), glycophosphatidylinositol (GPI), zymosan, hsp60, gH/gL glycoprotein, hemagglutinin), a TLR3 agonist (e.g., double-stranded RNA, e.g., poly(I:C)), a TLR4 agonist (e.g., lipopolysaccharides (LPS), lipoteichoic acid, β-defensin 2, fibronectin EDA, HMGB1, snapin, tenascin C), a TLR5 agonist (e.g., flagellin), a TLR6 agonist, a TLR7/8 agonist (e.g., single-stranded RNA, CpG-A, Poly G10, Poly G3, Resiquimod), a TLR9 agonist (e.g., unmethylated CpG DNA), and combinations thereof. Non-limiting examples of TLR agonists can be found at WO2008115319A2, US20130202707A1, US20120219615A1, US20100029585A1, WO2009030996A1, WO2009088401A2, and WO2011044246A1, each of which are incorporated by reference in its entirety.

In some aspects, the payload is a proteolysis-targeting chimera (PROTAC). PROTACs are heterobifunctional molecules consisting of a ligand to a target protein, a ligand to the E3 ubiquitinating ligase, and a linker connecting the two ligands. Once the target:PROTAC:E3 ternary complex is formed, E2 ubiquitin-conjugating enzymes transfer ubiquitin to lysine residues on the surface of the target protein. In some aspects, the PROTAC target is, e.g., ERα, BCR-ABL, BRD4, PDE4, ERRα, RIPK2, c-ABL, BRD2, BRD3, BRD4, FKBP12, TBK1, BRD9, EGFR, c-Met, Sirt2, CDK9, FLT3, BTK, ALK, AR, TRIM24, SMAD3, RAR, PI3K, PCAF, METAP2, HER2, HDAC6, GCNS, ERK1/2, DHODH, CRABP-II, FLT4, or CK2. In some aspects, the PROTAC target ligand is, e.g., 4-OHT, dasatinib, JQ1, a PDE4 inhibitor, JQ1, a chloroalkane, a thiazolidinedione-based ligand, a RIPK2 inhibitor, bosutinib, a JQ1 derivative, OTX015, steel factor, a TBK1 inhibitor, BI-7273, lapatinib, gefitinib, afatinib, foretinib, Sirt2 inhibitor 3b, HJB97, SNS-032, an aminopyrazole analog, AC220, RN-486, ceritinib, an AR antagonist, IACS-7e, or an ibrutinib derivative. In some aspects, the PROTAC E3 ligand is, e.g., an LCL161 derivative, VHL1, a hydroxyproline derivative, pomalidomide, thalidomide, a HIF-1α-derived (R)-hydroxyproline, VHL ligand 2, a VH032 derivative, lenalidomide, a thalidomide derivative, or VL-269. In some aspects, the E3 ligase is, e.g., IAP, VHL, or CRBN. See, for example, An & Fu (2018) EBioMedicine 36:553-562, which is herein incorporated by reference in its entirety.

PROTACS and related technologies that can be used according to the methods disclosed herein as disclosed for example in WO2018106870, US2018155322, WO2018098288, WO2018098280, WO2018098275, WO2018089736, WO2018085247, US20180125821, US20180099940, WO2018064589, WO2018053354, WO2017223452, WO2017201449, WO2017197056, WO2017197051, WO2017197046, WO2017185036, WO2017185034, WO2017185031, WO2017185023, WO2017182418, US20170305901, WO2017176708, US20170281784, WO2017117474, WO2017117473, WO2017079723, U.S. Pat. No. 9,938,264, US20170065719, WO2017024319, WO2017024318, WO2017024317, US20170037004, US20170008904, US20180147202, WO2018051107, WO2018033556, US20160272639, US20170327469, WO2017212329, WO2017211924, US20180085465, US20160045607, US20160022642, WO2017046036, US20160058872, US20180134688, US20180118733, US20180050021, U.S. Pat. No. 9,855,273, US20140255361, U.S. Pat. No. 9,115,184, US20180093990, US20150119435, US20140356322, US20140112922, U.S. Pat. No. 9,765,019, US20180100001, U.S. Pat. No. 7,390,656, or U.S. Pat. No. 7,208,157, all of which are herein incorporated by reference in their entireties.

In some aspects, when several PROTACs are present on an EV (e.g., exosome), such PROTACs can be the same or they can be different. In some aspects, when several non-cyclic dinucleotide STING agonist are present on an EV (e.g., exosome) disclosed herein, such PROTACs can be the same or they can be different. In some aspects, an EV (e.g., exosome) composition of the present disclosure can comprise two or more populations of EVs, e.g., exosomes, wherein each population of EVs, e.g., exosomes, comprises a different PROTAC or combination thereof.

In some aspects, the EV protein is Scaffold X. In some embodiments, EVs comprise one or more polypeptides on their surface. In some embodiments, the one or more polypeptides can be CD47, CD55, CD49, CD40, CD133, CD59, glypican-1, CD9, CD63, CD81, integrins, selectins, lectins, cadherins and/or other similar polypeptides known to those of skill in the art. In some embodiments, the one or more polypeptides can be a scaffold protein, such as PTGFRN, BSG, IGSF3, IGSF2, ITGB1, ITGA4, SLC3A2, ATP transporter or a fragment thereof. In some aspects, the payload (e.g., IL-12) is fused to Scaffold X, e.g. PTGFRN.

In some aspects, the EV protein is Scaffold Y. In some embodiments, the EV protein is polypeptide is BASP1. In some embodiments, the one or more polypeptides is a fusion protein comprising the scaffold protein fused to a different protein. In some embodiments, the surface protein can be expressed from an exogenous polynucleotide introduced to the producer cells. In some embodiments, the surface polypeptide can confer different functionalities to the EV, for example, specific targeting capabilities, delivery functions, enzymatic functions, increased or decreased half-life in vivo, and other desired functionalities known to those of skill in the art.

As previously described, producer cells can be genetically modified to comprise one or more exogenous sequences to produce EVs described herein. The genetically-modified producer cell can contain the exogenous sequence by transient or stable transfection and/or transformation. The exogenous sequence can be transformed as a plasmid. The exogenous sequences can be stably integrated into a genomic sequence of the producer cell, at a targeted site or in a random site. In some embodiments, a stable cell line is generated for production of lumen-engineered EVs.

The exogenous sequences can be inserted into a genomic sequence of the producer cell, located within, upstream (5'-end) or downstream (3'-end) of an endogenous sequence encoding an EV protein. Various methods known in the art can be used for the introduction of the exogenous sequences into the producer cell. For example, cells modified using various gene editing methods (e.g., methods using a homologous recombination, transposon-mediated system, loxP-Cre system, CRISPR/Cas9 or TALEN) are within the scope of the present disclosure.

The exogenous sequences can comprise a sequence encoding a scaffold moiety disclosed herein or a fragment or variant thereof. Extra copies of the sequence encoding a scaffold moiety can be introduced to produce an engineered EV described herein (e.g., having a higher density of a scaffold moiety on the exterior surface or on the luminal surface of the EV). An exogenous sequence encoding a modification or a fragment of a scaffold moiety can be introduced to produce a lumen-engineered and/or surface-engineered EV containing the modification or the fragment of the scaffold moiety.

In some embodiments, a producer cell disclosed herein is further modified to comprise an additional exogenous sequence. For example, an additional exogenous sequence can be introduced to modulate endogenous gene expression, or produce an EV including a certain polypeptide. In some embodiments, the producer cell is modified to comprise two exogenous sequences, one encoding a scaffold moiety (e.g., Scaffold X and/or Scaffold Y), or a variant or a fragment thereof, and the other encoding a molecule linked to the scaffold moiety. In certain embodiments, the producer cell can be further modified to comprise an additional exogenous sequence conferring additional functionalities to the EVs. In some embodiments, the producer cell is modified to comprise two exogenous sequences, one encoding a scaffold moiety disclosed herein, or a variant or a fragment thereof, and the other encoding a protein conferring the additional functionalities to the EVs. In some embodiments, the producer cell is further modified to comprise one, two, three, four, five, six, seven, eight, nine, or ten or more additional exogenous sequences.

In some embodiments, EVs of the present disclosure (e.g., surface-engineered and/or lumen-engineered EVs) can be produced from a cell transformed with a sequence encoding a full-length, mature scaffold moiety disclosed herein. Any of the scaffold moieties described herein can be expressed from a plasmid, an exogenous sequence inserted into the genome or other exogenous nucleic acid, such as a synthetic messenger RNA (mRNA).

In certain aspects, the one or more moieties are introduced into the EVs by transfection. In some aspects, the one or more moieties can be introduced into the EVs using synthetic macromolecules such as cationic lipids and polymers (Papapetrou et al., Gene Therapy 12: S118-S130 (2005)). In certain aspects, chemicals such as calcium phosphate, cyclodextrin, or polybrene, can be used to introduce the one or more moieties to the EVs.

In other embodiments, one or more scaffold moieties are expressed in the membrane of the EVs by recombinantly expressing the scaffold moieties in the producer cells. The EVs obtained from the producer cells can be further modified to be conjugated to a chemical compound, a nucleic acid, a peptide, a protein, or a linker. In other embodiments, the scaffold moiety, e.g., Scaffold X and/or Scaffold Y, is deglycosylated. In some embodiments, the scaffold moiety, Scaffold X and/or Scaffold Y, is highly glycosylated, e.g., higher than naturally-occurring Scaffold X and/or Scaffold Y under the same condition.

In certain embodiments, one or more moieties can be introduced into the EVs directly after exosome production e.g., loaded into the EVs: for example, passive diffusion, electroporation, chemical or polymeric transfection, viral transduction, mechanical membrane disruption or mechanical shear, or any combination thereof. In some embodiments, the one or more moieties and the EV, e.g., exosome, of the present disclosure can be incubated in an appropriate buffer during loading or encapsulation. The term "encapsulated", or grammatically different forms of the term (e.g., encapsulation, or encapsulating), refers to a status or process of having a first moiety (e.g., STING agonist) inside a second moiety (e.g., an EV, e.g., exosome) without chemically or physically linking the two moieties. In some embodiments, the term "encapsulated" can be used interchangeably with "in the lumen of" or "loaded". Non-limiting examples of encapsulating a first moiety (e.g., STING agonist) into a second moiety (e.g., EVs, e.g., exosomes) are disclosed elsewhere herein. In some embodiments, the moiety that can be encapsulated or loaded in the EVs includes a STING agonist. STING agonists refer to an agent that activates a STING pathway. Activation of the STING pathway in DCs results in Type I IFN and pro inflammatory cytokine production via TBK1, IRF3, and NF-κB signaling. Binding of IFN to their receptors on cells results in activation of IFN-stimulated response elements and the transcription of IFN-sensitive genes that result in the immune and inflammatory response. IFN signaling also cross-primes DCs to promote antigen persistence, alters the antigen repertoire available for MHCI presentation, enhances MHCI presentation of antigens, and increases the overall surface expression of MHCI, MHCII, and co-stimulatory molecules CD40, CD80, and CD86. These actions result in increased priming of tumor specific CD8+ T cells and initiation of the adaptive immune response.

In some embodiments, a STING agonist useful for the EVs of the present disclosure comprises a cyclic dinucleotide (CDN) and/or a non-cyclic nucleotide. STING agonists used in this disclosure can be cyclic purine dinucleotides such as, but not limited to, cGMP, cyclic di-GMP (c-di-GMP), cAMP, cyclic di-AMP (c-di-AMP), cyclic-GMP-AMP (cGAMP), cyclic di-IMP (c-di-IMP), cyclic AMP-IMP (cAIMP), and any analogue thereof, which are known to stimulate or enhance an immune or inflammation response in a patient. The CDNs may have 2'2', 2'3', 2'5', 3'3', or 3'5' bonds linking the cyclic dinucleotides, or any combination thereof. Further non-limiting examples of STING agonists that can be used with the present disclosure include: DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, and combinations thereof. Non-limiting examples of the STING agonists can also be found at U.S. Pat. No. 9,695, 212, WO 2014/189805 A1, WO 2014/179335 A1, WO 2018/100558 A1, U.S. Pat. No. 10,011,630 B2, WO 2017/027646 A1, WO 2017/161349 A1, and WO 2016/096174 A1, each of which is incorporated by reference in its entirety.

Cyclic purine dinucleotides can be modified via standard organic chemistry techniques to produce analogues of purine dinucleotides. Suitable purine dinucleotides include, but are not limited to, adenine, guanine, inosine, hypoxanthine, xanthine, isoguanine, or any other appropriate purine dinucleotide known in the art. The cyclic dinucleotides may be modified analogues. Any suitable modification known in the art may be used, including, but not limited to, phosphorothioate, biphosphorothioate, fluorinate, and difluorinate modifications.

Non cyclic dinucleotide agonists may also be used, such as 5,6-Dimethylxanthenone-4-acetic acid (DMXAA), or any other non-cyclic dinucleotide agonist known in the art.

It is contemplated that any STING agonist can be used. Among the STING agonists are DMXAA, STING agonist-1, ML RR-S2 CDA, ML RR-S2c-di-GMP, ML-RR-S2 cGAMP, 2'3'-c-di-AM(PS)2, 2'3'-cGAMP, 2'3'-cGAMPdFHS, 3'3'-cGAMP, 3'3'-cGAMPdFSH, cAIMP, cAIM(PS)2, 3'3'-cAIMP, 3'3'-cAIMPdFSH, 2'2'-cGAMP, 2'3'-cGAM(PS)2, 3'3'-cGAMP, c-di-AMP, 2'3'-c-di-AMP, 2'3'-c-di-AM(PS)2, c-di-GMP, 2'3'-c-di-GMP, c-di-IMP, c-di-UMP or any combination thereof. In some embodiments, the STING agonist is 3'3'-cAIMPdFSH, alternatively named 3-3 cAIMPdFSH. Additional STING agonists known in the art can also be used.

III.A. Scaffold X

Various modifications or fragments of the scaffold moiety can be used for the embodiments of the present disclosure. For example, scaffold moieties modified to have enhanced affinity to a binding agent can be used for generating surface-engineered EVs that can be purified using the binding agent. Scaffold moieties modified to be more effectively targeted to EVs and/or membranes can be used. Scaffold moieties modified to comprise a minimal fragment required for specific and effective targeting to EV membranes can be also used. In some embodiments, scaffold moieties can be linked to a linker or a biologically active molecule.

Scaffold moieties can be engineered synthetically or recombinantly, e.g., to be expressed as a fusion protein, e.g., fusion protein of Scaffold X to another moiety. For example, the fusion protein can comprise a scaffold moiety disclosed herein (e.g., Scaffold X, e.g., PTGFRN, BSG, IGSF2, IGSF3, IGSF8, ITGB1, ITGA4, SLC3A2, ATP transporter, or a fragment or a variant thereof) linked to another moiety. In case of the fusion protein, the second moiety can be a natural peptide, a recombinant peptide, a synthetic peptide, or any combination thereof.

In some embodiments, the surface (e.g., Scaffold X)-engineered EVs described herein demonstrate superior characteristics compared to EVs known in the art. For example, surface (e.g., Scaffold X)-engineered contain modified proteins more highly enriched on their surface or lumen of the EVs than naturally occurring EVs or the EVs produced using conventional EV proteins. Moreover, the surface (e.g., Scaffold X)-engineered EVs of the present disclosure can have greater, more specific, or more controlled biological activity compared to naturally occurring EVs or the EVs produced using conventional EV proteins.

In some embodiments, the Scaffold X comprises Prostaglandin F2 receptor negative regulator (the PTGFRN polypeptide). The PTGFRN polypeptide can be also referred to as CD9 partner 1 (CD9P-1), Glu-Trp-Ile EWI motif-containing protein F (EWI-F), Prostaglandin F2-alpha receptor regulatory protein, Prostaglandin F2-alpha receptor-associated protein, or CD315. The full-length amino acid sequence of the human PTGFRN polypeptide (Uniprot Accession No. Q9P2B2) is shown at Table 1 as SEQ ID NO: 1. The PTGFRN polypeptide contains a signal peptide (amino acids 1 to 25 of SEQ ID NO: 1), the extracellular domain (amino acids 26 to 832 of SEQ ID NO: 1), a transmembrane domain (amino acids 833 to 853 of SEQ ID NO: 1), and a cytoplasmic domain (amino acids 854 to 879 of SEQ ID NO: 1). The mature PTGFRN polypeptide consists of SEQ ID NO: 1 without the signal peptide, i.e., amino acids 26 to 879 of SEQ ID NO: 1. In some embodiments, a PTGFRN polypeptide fragment useful for the present disclosure comprises a transmembrane domain of the PTGFRN polypeptide. In other embodiments, a PTGFRN polypeptide fragment useful for the present disclosure comprises the transmembrane domain of the PTGFRN polypeptide and (i) at least five, at least 10, at least 15, at least 20, at least 25, at least 30, at least 40, at least 50, at least 70, at least 80, at least 90, at least 100, at least 110, at least 120, at least 130, at least 140, at least 150 amino acids at the N terminus of the transmembrane domain, (ii) at least five, at least 10, at least 15, at least 20, or at least 25 amino acids at the C terminus of the transmembrane domain, or both (i) and (ii).

In some embodiments, the fragments of PTGFRN polypeptide lack one or more functional or structural domains, such as IgV.

In other embodiments, the Scaffold X comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 26 to 879 of SEQ ID NO: 1. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 2. In other embodiments, the Scaffold X comprises the amino acid sequence of SEQ ID NO: 2, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of SEQ ID NO: 2 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 2.

In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to amino acids 26 to 879 of SEQ ID NO: 1, amino acids 833 to 853 of SEQ ID NO: 1, SEQ ID NO: 2, or SEQ ID NO: 1. In other embodiments, the Scaffold X comprises the amino acid sequence of amino acids 26 to 879 of SEQ ID NO: 1, amino acids 833 to 853 of SEQ ID NO: 1, SEQ ID NO: 2, or SEQ ID NO: 1, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, the Scaffold X comprises the amino acid sequence of amino acids 26 to 879 of SEQ ID NO: 1, amino acids 833 to 853 of SEQ ID NO: 1, SEQ ID NO: 2, or SEQ ID NO: 1 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of amino acids 26 to 879 of SEQ ID NO: 1, amino acids 833 to 853 of SEQ ID NO: 1, SEQ ID NO: 2, or SEQ ID NO: 1.

TABLE 1

| Protein | Sequence |
| --- | --- |
| PTGFRN polypeptide (SEQ ID NO: 1) | MGRLASRPLLLALLSLALCRGRVVRVPTATLVRVVGT ELVIPCNVSDYDGPSEQNFDWSFSSLGSSFVELASTW EVGFPAQLYQERLQRGEILLRRTANDAVELHIKNVQP SDQGHYKCSTPSTDATVQGNYEDTVQVKVLADSLHVG PSARPPPSLSLREGEPFELRCTAASASPLHTHLALLW EVHRGPARRSVLALTHEGRFHPGLGYEQRYHSGDVRL DTVGSDAYRLSVSRALSADQGSYRCIVSEWIAEQGNW QEIQEKAVEVATVVIQPSVLRAAVPKNVSVAEGKELD LTCNITTDRADDVRPEVTWSFSRMPDSTLPGSRVLAR LDRDSLVHSSPHVALSHVDARSYHLLVRDVSKENSGY YYCHVSLWAPGHNRSWHKVAEAVSSPAGVGVTWLEPD YQVYLNASKVPGFADDPTELACRVVDTKSGEANVRFT VSWYYRMNRRSDNVVTSELLAVMDGDWTLKYGERSKQ RAQDGDFIFSKEHTDTFNFRIQRTTEEDRGNYYCVVS AWTKQRNNSWVKSKDVFSKPVNIFWALEDSVLVVKAR QPKPFFAAGNTFEMTCKVSSKNIKSPRYSVLIMAEKP VGDLSSPNETKYIISLDQDSVVKLENWTDASRVDGVV LEKVQEDEFRYRMYQTQVSDAGLYRCMVTAWSPVRGS LWREAATSLSNPIEIDFQTSGPIFNASVHSDTPSVIR GDLIKLFCIITVEGAALDPDDMAFDVSWFAVHSFGLD KAPVLLSSLDRKGIVTTSRRDWKSDLSLERVSVLEFL LQVHGSEDQDFGNYYCSVTPWVKSPTGSWQKEAEIHS KPVFITVKMDVLNAFKYPLLIGVGLSTVIGLLSCLIG YCSSHWCCKKEVQETRRERRRLMSMEMD |
| PTGFRN polypeptide Fragment | GPIFNASVHSDTPSVIRGDLIKLFCIITVEGAALDPD DMAFDVSWFAVHSFGLDKAPVLLSSLDRKGIVTTSRR DWKSDLSLERVSVLEFLLQVHGSEDQDFGNYYCSVTP |

TABLE 1-continued

| Protein | Sequence |
| --- | --- |
| (SEQ ID NO: 2) | WVKSPTGSWQKEAEIHSKPVFITVKMDVLNAFKYPLL IGVGLSTVIGLLSCLIGYCSSHWCCKKEVQETRRERR RLMSMEM 687-878 of SEQ ID NO: 1 |

In other embodiments, the Scaffold X comprises the BSG protein, the IGSF8 protein, the IGSF3 protein, the ITGB1 protein, the SLC3A2 protein, the ITGA4 protein, the ATP protein, the ATP protein, the ATP protein, the ATP protein, the ATP1A5 protein, the ATP2B1 protein, the ATP2B2 protein, the ATP2B3 protein, the ATP2B4 protein, or the IGSF2 protein, which comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the corresponding mature BSG protein, IGSF8 protein, IGSF3 protein, ITGB1 protein, SLC3A2 protein, ITGA4 protein, ATP protein, ATP protein, ATP protein, ATP protein, ATP1A5 protein, ATP2B1 protein, ATP2B2 protein, ATP2B3 protein, ATP2B4 protein, or IGSF2 protein (without the signal peptide). In some embodiments, the BSG protein, the IGSF8 protein, the IGSF3 protein, the ITGB1 protein, the SLC3A2 protein, the ITGA4 protein, the ATP1A1 protein, the ATP1A2 protein, the ATP1A3 protein, the ATP1A4 protein, the ATP1A5 protein, the ATP2B1 protein, the ATP2B2 protein, the ATP2B3 protein, the ATP2B4 protein, or the IGSF2 protein lacks one or more functional or structural domains, such as IgV.

Non-limiting examples of other Scaffold X proteins can be found at U.S. Pat. No. 10,195,290B1, issued Feb. 5, 2019, which is incorporated by reference in its entirety, the ATP transporter proteins: ATP1A1, ATP1A2, ATP1A3, ATP1A4, ATP1B3, ATP2B1, ATP2B2, and ATP2B4), CD13 (aminopeptidase N), MME (membrane metalloendopeptidase), ENPP1 (ectonucleotide pyrophosphatase/phosphodiesterase family member 1), NRP1 (neuropilin-1), CD9, CD63, CD81, PDGFR, GPI anchor proteins, lactadherin, LAMP2, and LAMP2B.

In some embodiments, the sequence encodes a fragment of the scaffold moiety lacking at least 5, 10, 50, 100, 200, 300, 400, 500, 600, 700, or 800 amino acids from the N-terminus of the native protein. In some embodiments, the sequence encodes a fragment of the scaffold moiety lacking at least 5, 10, 50, 100, 200, 300, 400, 500, 600, 700, or 800 amino acids from the C-terminus of the native protein. In some embodiments, the sequence encodes a fragment of the scaffold moiety lacking at least 5, 10, 50, 100, 200, 300, 400, 500, 600, 700, or 800 amino acids from both the N-terminus and C-terminus of the native protein. In some embodiments, the sequence encodes a fragment of the scaffold moiety lacking one or more functional or structural domains of the native protein.

In some embodiments, the scaffold moieties, e.g., Scaffold X, e.g., a PTGFRN protein, are linked to one or more heterologous proteins. The one or more heterologous proteins can be linked to the N-terminus of the scaffold moieties. The one or more heterologous proteins can be linked to the C-terminus of the scaffold moieties. In some embodiments, the one or more heterologous proteins are linked to both the N-terminus and the C-terminus of the scaffold moieties. In some embodiments, the heterologous protein is a mammalian protein. In some embodiments, the heterologous protein is a human protein.

In some embodiments, Scaffold X can be used to link any moiety on the luminal surface and on the exterior surface of the EV at the same time. For example, the PTGFRN polypeptide can be used to link one or more biologically active molecules indirectly or directly to the surface of the EVs. Therefore, in certain embodiments, Scaffold X can be used for dual purposes.

In other embodiments, the EVs of the present disclosure comprises a higher number of Scaffold X proteins compared to the naturally-occurring EVs. In some embodiments, the EVs of the disclosure comprise at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 110 fold, at least about 120 fold, at least about 130 fold, at least about 140 fold, at least about 150 fold, at least about 160 fold, at least about 170 fold, at least about 180 fold, at least about 190 fold, at least about 200 fold, at least about 210 fold, at least about 220 fold, at least about 230 fold, at least about 240 fold, at least about 250 fold, at least about 260 fold, at least about 270 fold higher number of Scaffold X (e.g., a PTGFRN polypeptide) compared to the naturally-occurring EV. The number of Scaffold X, e.g., PTGFRN polypeptide, on the EV of the present disclosure is at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 4000, at least about 5000, at least about 6000, at least about 7000, at least about 8000, at least about 9000, or at least about 10000. In some embodiments, the number of Scaffold X, e.g., a PTGFRN polypeptide, on the EV of the present disclosure is from about 100 to about 100,000, from about 200 to about 9000, from about 300 to about 9000, from about 400 to about 9000, from about 500 to about 9000, from about 600 to about 8000, from about 800 to about 8000, from about 900 to about 8000, from about 1000 to about 8000, from about 1100 to about 8000, from about 1200 to about 8000, from about 1300 to about 8000, from about 1400 to about 8000, from about 1500 to about 8000, from about 1600 to about 8000, from about 1700 to about 8000, from about 1800 to about 8000, from about 1900 to about 8000, from about 2000 to about 8000, from about 2100 to about 8000, from about 2200 to about 8000, from about 2300 to about 8000, from about 2400 to about 8000, from about 2500 to about 8000, from about 2600 to about 2700 to about 8000, from about 2800 to about 8000, from about 2900 to about 8000, from about 3000 to about 8000, from about 4000 to about 8000, from about 5000 to about 8000, from about 6000 to about 8000, from about 7000 to about 8000, from about 8000, from 7000 to about 9000, or from about 6000 to about 10000. In some embodiments, the number of Scaffold X, e.g., PTGFRN polypeptide, on the EV of the present disclosure is from about 5000 to about 8000, e.g., about 5000, about 6000, about 7000, or about 8000. In some embodiments, the number of Scaffold X, e.g., PTGFRN polypeptide, on the EV of the present disclosure is from about 6000 to about 8000, e.g., about 6000, about 7000, or about 8000. In some embodiments, the number of Scaffold X, e.g., PTGFRN polypeptide, on the EV of the present disclosure is from about 4000 to about 9000, e.g., about 4000, about 5000, about 6000, about 7000, about 8000, about 9000.

III.B. Scaffold Y

In some embodiments, EVs of the present disclosure comprise an internal space (i.e., lumen) that is different from that of the naturally occurring EVs. For example, the EV can be changed such that the composition in the luminal side of the EV has the protein, lipid, or glycan content different from that of the naturally-occurring EVs.

In some embodiments, engineered EVs can be produced from a cell transformed with an exogenous sequence encoding a scaffold moiety (e.g., EV proteins, e.g., Scaffold Y) or a modification or a fragment of the scaffold moiety that changes the composition or content of the luminal side of the EV. Various modifications or fragments of the EV protein that can be expressed in the luminal side of the EV can be used for the embodiments of the present disclosure.

In some embodiments, the EV proteins that can change the luminal side of the EVs include, but are not limited to the MARCKS protein, MARCKSL1 protein, BASP1 protein, or any combination thereof. In some embodiments, the Scaffold Y comprises Brain Acid Soluble Protein 1 (the BASP1 protein). The BASP1 protein is also known as 22 kDa neuronal tissue-enriched acidic protein or neuronal axonal membrane protein NAP-22. The full-length human BASP1 protein sequence (isomer 1) is shown in Table 2. An isomer produced by an alternative splicing is missing amino acids 88 to 141 from SEQ ID NO: 3 (isomer 1).

TABLE 2

| Protein | Sequence |
|---|---|
| The BASP1 protein (SEQ ID NO: 3) | MGGKLSKKKK GYNVNDEKAK EKDKKAEGAA TEEEGTPKES EPQAAAEPAE AKEGKEKPDQ DAEGKAEEKE GEKDAAAAKE EAPKAEPEKT EGAAEAKAEP PKAPEQEQAA PGPAAGGEAP KAAEAAAAPA ESAAPAAGEE PSKEEGEPKK TEAPAAPAAQ ETKSDGAPAS DSKPGSSEAA PSSKETPAAT EAPSSTPKAQ GPAASAEEPK PVEAPAANSD QTVTVKE |

The mature BASP1 protein sequence is missing the first Met from SEQ ID NO: 3 and thus contains amino acids 2 to 227 of SEQ ID NO: 3.

In other embodiments, Scaffold Y useful for the present disclosure comprises an amino acid sequence at least about 70%, at least about 75%, at least about 80%, at least about 85%, at least about 90%, at least about 95%, at least about 96%, at least about 97%, at least about 98%, at least about 99%, or about 100% identical to amino acids 2 to 227 of SEQ ID NO: 3. In other embodiments, the Scaffold X comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to SEQ ID NO: 3. In other embodiments, a Scaffold Y useful for the present disclosure comprises the amino acid sequence of SEQ ID NO: 3, except one amino acid mutation, two amino acid mutations, three amino acid mutations, four amino acid mutations, five amino acid mutations, six amino acid mutations, or seven amino acid mutations. The mutations can be a substitution, an insertion, a deletion, or any combination thereof. In some embodiments, a Scaffold Y useful for the present disclosure comprises the amino acid sequence of SEQ ID NO: 3 and 1 amino acid, two amino acids, three amino acids, four amino acids, five amino acids, six amino acids, seven amino acids, eight amino acids, nine amino acids, ten amino acids, 11 amino acids, 12 amino acids, 13 amino acids, 14 amino acids, 15 amino acids, 16 amino acids, 17 amino acids, 18 amino acids, 19 amino acids, or 20 amino acids or longer at the N terminus and/or C terminus of SEQ ID NO: 3.

In some embodiments, a scaffold moiety is Scaffold Y. In some embodiments, such an exogenous sequence encodes BASP1 protein of SEQ ID NO: 3. In certain embodiments, the protein sequence of any of SEQ ID NOs: 1-109 disclosed in PCT/US2018/061679 is sufficient to be a Scaffold Y for the present disclosure (e.g., scaffold moiety linked to a linker).

In certain embodiments, a Scaffold Y useful for the present disclosure comprises a peptide with the MGXKL-SKKK, where X is alanine or any other amino acid (SEQ ID NO: 4). In some embodiments, an EV comprises a peptide with sequence of (M)(G)(π)(ξ)(Φ/π)(S/A/G/N)(+)(+), wherein each parenthetical position represents an amino acid, and wherein 7C is any amino acid selected from the group consisting of (Pro, Gly, Ala, Ser), is any amino acid selected from the group consisting of (Asn, Gln, Ser, Thr, Asp, Glu, Lys, His, Arg), 1 is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu). In further embodiments, an EV described herein (e.g., engineered EVs) comprises a peptide with sequence of (M)(G)(π)(X)(Φ/π)(n)(+)(+), wherein each parenthetical position represents an amino acid, and wherein π is any amino acid selected from the group consisting of (Pro, Gly, Ala, Ser), X is any amino acid, Φ is any amino acid selected from the group consisting of (Val, Ile, Leu, Phe, Trp, Tyr, Met), and (+) is any amino acid selected from the group consisting of (Lys, Arg, His); and wherein position five is not (+) and position six is neither (+) nor (Asp or Glu).

In other embodiments, the Scaffold Y comprises an amino acid sequence at least about at least about 70%, at least about 75%, at least about 80%, at least about 85%, at least about 90%, at least about 95%, at least about 96%, at least about 97%, at least about 98%, at least about 99%, or about 100% identical to any one of the sequences disclosed in U.S. Pat. No. 10,195,290B1, issued Feb. 5, 2019.

Scaffold Y-engineered EVs described herein can be produced from a cell transformed with any sequence set forth in PCT/US2018/061679 (SEQ ID NO: 4-109).

In other embodiments, the EVs of the present disclosure comprises a higher number of Scaffold Y proteins compared to the naturally-occurring EVs. In some embodiments, the EVs of the disclosure comprise at least about 5 fold, at least about 10 fold, at least about 20 fold, at least about 30 fold, at least about 40 fold, at least about 50 fold, at least about 60 fold, at least about 70 fold, at least about 80 fold, at least about 90 fold, at least about 100 fold, at least about 110 fold, at least about 120 fold, at least about 130 fold, at least about 140 fold, at least about 150 fold, at least about 160 fold, at least about 170 fold, at least about 180 fold, at least about 190 fold, at least about 200 fold, at least about 210 fold, at least about 220 fold, at least about 230 fold, at least about 240 fold, at least about 250 fold, at least about 260 fold, at least about 270 fold higher number of Scaffold Y (e.g., a BASP-1 polypeptide) compared to the naturally-occurring EV. The number of Scaffold Y, e.g., BASP-1 polypeptide, on the EV of the present disclosure is at least about 100, at least about 200, at least about 300, at least about 400, at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 4000, at least about 5000, at least about 6000, at least about 7000, at least about 8000, at least about 9000, or at least about 10000. In some embodiments, the number of Scaffold Y, e.g., a BASP-1 polypeptide, on the EV of the present disclosure is from about 100 to about 100,000, from about 200 to about 9000, from about 300 to about 9000, from about 400 to about 9000, from about 500 to about 9000, from about 600 to about 8000, from about 800 to about 8000, from about 900 to about 8000, from about 1000 to about 8000, from about 1100 to about 8000, from about 1200 to about 8000, from about 1300 to about 8000, from about 1400 to about 8000, from about 1500 to about 8000, from about 1600 to about 8000, from about 1700 to about 8000, from about 1800 to about 8000, from about 1900 to about 8000, from about 2000 to about 8000, from about 2100 to about 8000, from about 2200 to about 8000, from about 2300 to about 8000, from about 2400 to about 8000, from about 2500 to about 8000, from about 2600, from about 2700 to about 8000, from about 2800 to about 8000, from about 2900 to about 8000, from about 3000 to about 8000, from about 4000 to about 8000, from about 5000 to about 8000, from about 6000 to about 8000, from about 7000 to about 8000, from about 8000, from 7000 to about 9000, or from about 6000 to about 10000. In some embodiments, the number of Scaffold Y, e.g., a BASP-1 polypeptide, on the EV of the present disclosure is from about 5000 to about 8000, e.g., about 5000, about 6000, about 7000, or about 8000. In some embodiments, the number of Scaffold Y, e.g., a BASP-1 polypeptide, on the EV of the present disclosure is from about 6000 to about 8000, e.g., about 6000, about 7000, or about 8000. In some embodiments, the number of Scaffold Y, e.g., a BASP-1 polypeptide, on the EV of the present disclosure is from about 4000 to about 9000, e.g., about 4000, about 5000, about 6000, about 7000, about 8000, or about 9000.

In some aspects, the Scaffold Y useful for the present disclosure comprises an "N-terminus domain" (ND) and an "effector domain" (ED), wherein the ND and/or the ED are associated with the luminal surface of the EV, e.g., an exosome. In some aspects, the Scaffold Y useful for the present disclosure comprises an intracellular domain, a transmembrane domain, and an extracellular domain; wherein the intracellular domain comprises an "N-terminus domain" (ND) and an "effector domain" (ED), wherein the ND and/or the ED are associated with the luminal surface of the EV, e.g., an exosome. As used herein the term "associated with" refers to the interaction between a scaffold protein with the luminal surface of the EV, e.g., and exosome, that does not involve covalent linking to a membrane component. For example, the scaffolds useful for the present disclosure can be associated with the luminal surface of the EV, e.g., via a lipid anchor (e.g., myristic acid), and/or a polybasic domain that interacts electrostatically with the negatively charged head of membrane phospholipids. In other aspects, the Scaffold Y comprises an N-terminus domain (ND) and an effector domain (ED), wherein the ND is associated with the luminal surface of the EV and the ED are associated with the luminal surface of the EV by an ionic interaction, wherein the ED comprises at least two, at least three, at least four, at least five, at least six, or at least seven contiguous lysines (Lys) in sequence.

In other embodiments, the Scaffold Y comprises an N-terminus domain (ND) and an effector domain (ED), wherein the ND is associated with the luminal surface of the EV, and the ED is associated with the luminal surface of the EV by an ionic interaction, wherein the ED comprises at least two, at least three, at least four, at least five, at least six, or at least seven contiguous basic amino acids, e.g., lysines (Lys), in sequence.

In some aspects, the ND is associated with the luminal surface of the EV, e.g., an exosome, via lipidation, e.g., via myristoylation. In some aspects, the ND has Gly at the N terminus. In some aspects, the N-terminal Gly is myristoylated.

In some aspects, the ED is associated with the luminal surface of the EV, e.g., an exosome, by an ionic interaction. In some aspects, the ED is associated with the luminal surface of the EV, e.g., an exosome, by an electrostatic interaction, in particular, an attractive electrostatic interaction.

In some aspects, the ED comprises (i) a basic amino acid (e.g., lysine), or (ii) two or more basic amino acids (e.g., lysine) next to each other in a polypeptide sequence. In some aspects, the basic amino acid is lysine (Lys; K), arginine (Arg, R), or Histidine (His, H). In some aspects, the basic amino acid is (Lys)n, wherein n is an integer between 1 and 10.

In other aspects, the ED comprises at least a lysine and the ND comprises a lysine at the C terminus if the N terminus of the ED is directly linked to lysine at the C terminus of the ND, i.e., the lysine is in the N terminus of the ED and is fused to the lysine in the C terminus of the ND. In other embodiments, the ED comprises at least two lysines, at least three lysines, at least four lysines, at least five lysines, at least six lysines, or at least seven lysines when the N terminus of the ED is linked to the C terminus of the ND by a linker, e.g., one or more amino acids.

In some aspects, the ED comprises K, KK, KKK, KKKK (SEQ ID NO: 5), KKKKK (SEQ ID NO: 6), R, RR, RRR, RRRR (SEQ ID NO: 7); RRRRR (SEQ ID NO: 8), KR, RK, KKR, KRK, RKK, RKK, KRR, RRK, (K/R)(K/R)(K/R)(K/R) (SEQ ID NO: 9), (K/R)(K/R)(K/R)(K/R)(K/R) (SEQ ID NO: 10), or any combination thereof. In some aspects, the ED comprises KK, KKK, KKKK (SEQ ID NO: 5), KKKKK (SEQ ID NO: 6), or any combination thereof. In some aspects, the ND comprises the amino acid sequence as set forth in G:X2:X3:X4:X5:X6, wherein G represents Gly; wherein ":" represents a peptide bond; wherein each of the X2 to the X6 independently represents an amino acid; and wherein the X6 represents a basic amino acid. In some aspects, the X6 amino acid is selected is selected from the group consisting of Lys, Arg, and His. In some aspects, the X5 amino acid is selected from the group consisting of Pro, Gly, Ala, and Ser. In some aspects, the X2 amino acid is selected from the group consisting of Pro, Gly, Ala, and Ser. In some aspects, the X4 is selected from the group consisting of Pro, Gly, Ala, Ser, Val, Ile, Leu, Phe, Trp, Tyr, Gln, and Met.

In some aspects, the Scaffold Y comprises an N-terminus domain (ND) and an effector domain (ED), wherein the ND comprises the amino acid sequence as set forth in G:X2:X3:X4:X5:X6, wherein G represents Gly; wherein ":" represents a peptide bond; wherein each of the X2 to the X6 is independently an amino acid; wherein the X6 comprises a basic amino acid, and wherein the ED is linked to X6 by a peptide bond and comprises at least one lysine at the N terminus of the ED.

In some aspects, the ND of the Scaffold Y comprises the amino acid sequence of G:X2:X3:X4:X5:X6, wherein G represents Gly; ":" represents a peptide bond; the X2 represents an amino acid selected from the group consisting of Pro, Gly, Ala, and Ser; the X3 represents any amino acid; the X4 represents an amino acid selected from the group consisting of Pro, Gly, Ala, Ser, Val, Ile, Leu, Phe, Trp, Tyr, Gln, and Met; the X5 represents an amino acid selected from the group consisting of Pro, Gly, Ala, and Ser; and the X6 represents an amino acid selected from the group consisting of Lys, Arg, and His.

In some aspects, the X3 amino acid is selected from the group consisting of Asn, Gln, Ser, Thr, Asp, Glu, Lys, His, and Arg.

In some aspects, the ND and ED are joined by a linker. In some aspects, the linker comprises one or more amino acids. In some aspects, the term "linker" refers to a peptide or polypeptide sequence (e.g., a synthetic peptide or polypeptide sequence) or to a non-polypeptide, e.g., an alkyl chain. In some aspects, two or more linkers can be linked in tandem. Generally, linkers provide flexibility or prevent/ameliorate steric hindrances. Linkers are not typically cleaved; however in certain aspects, such cleavage can be desirable. Accordingly, in some aspects a linker can comprise one or more protease-cleavable sites, which can be located within the sequence of the linker or flanking the linker at either end of the linker sequence. When the ND and ED are joined by a linker, the ED comprise at least two lysines, at least three lysines, at least four lysines, at least five lysines, at least six lysines, or at least seven lysines.

In some aspects, the linker is a peptide linker. In some aspects, the peptide linker can comprise at least about two, at least about three, at least about four, at least about five, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 amino acids.

In some aspects, the linker is a glycine/serine linker. In some aspects, the peptide linker is glycine/serine linker according to the formula [(Gly)n-Ser]m where n is any integer from 1 to 100 and m is any integer from 1 to 100. In other aspects, the glycine/serine linker is according to the formula [(Gly)x-Sery]z wherein x in an integer from 1 to 4, y is 0 or 1, and z is an integers from 1 to 50. In some aspects, the peptide linker comprises the sequence Gn, where n can be an integer from 1 to 100. In some aspects, the peptide linker can comprise the sequence (GlyAla)n, wherein n is an integer between 1 and 100. In other aspects, the peptide linker can comprise the sequence (GlyGlySer)n, wherein n is an integer between 1 and 100.

In some aspects, the peptide linker is synthetic, i.e., non-naturally occurring. In one aspect, a peptide linker includes peptides (or polypeptides) (e.g., natural or non-naturally occurring peptides) which comprise an amino acid sequence that links or genetically fuses a first linear sequence of amino acids to a second linear sequence of amino acids to which it is not naturally linked or genetically fused in nature. For example, in one aspect the peptide linker can comprise non-naturally occurring polypeptides which are modified forms of naturally occurring polypeptides (e.g., comprising a mutation such as an addition, substitution or deletion).

In other aspects, the peptide linker can comprise non-naturally occurring amino acids. In yet other aspects, the peptide linker can comprise naturally occurring amino acids occurring in a linear sequence that does not occur in nature. In still other aspects, the peptide linker can comprise a naturally occurring polypeptide sequence.

In some aspects, the Scaffold Y comprises ND-ED, wherein: ND comprises G:X2:X3:X4:X5:X6; wherein: G represents Gly; ":" represents a peptide bond; X2 represents an amino acid selected from the group consisting of Pro, Gly, Ala, and Ser; X3 represents any amino acid; X4 represents an amino acid selected from the group consisting of Pro, Gly, Ala, Ser, Val, Ile, Leu, Phe, Trp, Tyr, Glu, and Met; X5 represents an amino acid selected from the group consisting of Pro, Gly, Ala, and Ser; X6 represents an amino acid selected from the group consisting of Lys, Arg, and His; "—" represents an optional linker; and ED is an effector domain comprising (i) at least two contiguous lysines (Lys), which is linked to the X6 by a peptide bond or one or more amino acids or (ii) at least one lysine, which is directly linked to the X6 by a peptide bond.

In some aspects, the X2 amino acid is selected from the group consisting of Gly and Ala. In some aspects, the X3 amino acid is Lys. In some aspects, the X4 amino acid is Leu or Glu. In some aspects, the X5 amino acid is selected from the group consisting of Ser and Ala. In some aspects, the X6 amino acid is Lys. In some aspects, the X2 amino acid is Gly, Ala, or Ser; the X3 amino acid is Lys or Glu; the X4 amino acid is Leu, Phe, Ser, or Glu; the X5 amino acid is Ser or Ala; and X6 amino acid is Lys. In some aspects, the "—" linker comprises a peptide bond or one or more amino acids.

In some aspects, the ED in the scaffold protein comprises Lys (K), KK, KKK, KKKK (SEQ ID NO: 5), KKKKK (SEQ ID NO: 6), Arg (R), RR, RRR, RRRR (SEQ ID NO: 7); RRRRR (SEQ ID NO: 8), KR, RK, KKR, KRK, RKK, KRR, RRK, (K/R)(K/R)(K/R)(K/R) (SEQ ID NO: 9), (K/R)(K/R)(K/R)(K/R)(K/R) (SEQ ID NO: 10), or any combination thereof.

In some aspects, the Scaffold Y comprises an amino acid sequence selected from the group consisting of (i) GGKLSKK (SEQ ID NO: 11), (ii) GAKLSKK (SEQ ID NO: 12), (iii) GGKQSKK (SEQ ID NO: 13), (iv) GGKLAKK (SEQ ID NO: 14), or (v) any combination thereof.

In some aspects, the ND in the Scaffold Y comprises an amino acid sequence selected from the group consisting of (i) GGKLSK (SEQ ID NO: 15), (ii) GAKLSK (SEQ ID NO: 16), (iii) GGKQSK (SEQ ID NO: 17), (iv) GGKLAK (SEQ ID NO: 18), or (v) any combination thereof and the ED in the scaffold protein comprises (i) K, KK, KKK, KKKG (SEQ ID NO: 19), KKKGY (SEQ ID NO: 20), KKKGYN (SEQ ID NO: 21), KKKGYNV (SEQ ID NO: 22), KKKGYNVN (SEQ ID NO: 23), KKKGYS (SEQ ID NO: 24), KKKGYG (SEQ ID NO: 25), KKKGYGG (SEQ ID NO: 26), KKKGS (SEQ ID NO: 27), KKKGSG (SEQ ID NO: 28), KKKGSGS (SEQ ID NO: 29), KKKS (SEQ ID NO: 230), KKKSG (SEQ ID NO: 31), KKKSGG (SEQ ID NO: 32), KKKSGGS (SEQ ID NO: 33), KKKSGGSG (SEQ ID NO: 34), KKSGGSGG (SEQ ID NO: 35), KKKSGGSGGS (SEQ ID NO: 36), KRFSFKKS (SEQ ID NO: 37).

In some aspects, the polypeptide sequence of a Scaffold Y useful for the present disclosure consists of an amino acid sequence selected from the group consisting of (i) GGKLSKK (SEQ ID NO: 11), (ii) GAKLSKK (SEQ ID NO: 12), (iii) GGKQSKK (SEQ ID NO: 13), (iv) GGKLAKK (SEQ ID NO: 14), or (v) any combination thereof.

In some aspects, the Scaffold Y comprises an amino acid sequence selected from the group consisting of (i) GGKL- SKKK (SEQ ID NO: 38), (ii) GGKLSKKS (SEQ ID NO: 39), (iii) GAKLSKKK (SEQ ID NO: 40), (iv) GAKLSKKS (SEQ ID NO: 41), (v) GGKQSKKK (SEQ ID NO: 42), (vi) GGKQSKKS (SEQ ID NO: 43), (vii) GGKLAKKK (SEQ ID NO: 44), (viii) GGKLAKKS (SEQ ID NO: 45), and (ix) any combination thereof.

In some aspects, the polypeptide sequence of a Scaffold Y useful for the present disclosure consists of an amino acid sequence selected from the group consisting of (i) GGKLSKKK (SEQ ID NO: 38), (ii) GGKLSKKS (SEQ ID NO: 39), (iii) GAKLSKKK (SEQ ID NO: 40), (iv) GAKLSKKS (SEQ ID NO: 41), (v) GGKQSKKK (SEQ ID NO: 42), (vi) GGKQSKKS (SEQ ID NO: 43), (vii) GGKLAKKK (SEQ ID NO: 44), (viii) GGKLAKKS (SEQ ID NO: 45), and (ix) any combination thereof.

In some aspects, the Scaffold Y is at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 39, at least about 40, at least about 41, at least about 42, at least about 43, at least about 44, at least about 50, at least about 46, at least about 47, at least about 48, at least about 49, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 305, at least about 310, at least about 315, at least about 320, at least about 325, at least about 330, at least about 335, at least about 340, at least about 345, or at least about 350 amino acids in length.

In some aspects, the Scaffold Y is between about 5 and about 10, between about 10 and about 20, between about 20 and about 30, between about 30 and about 40, between about 40 and about 50, between about 50 and about 60, between about 60 and about 70, between about 70 and about 80, between about 80 and about 90, between about 90 and about 100, between about 100 and about 110, between about 110 and about 120, between about 120 and about 130, between about 130 and about 140, between about 140 and about 150, between about 150 and about 160, between about 160 and about 170, between about 170 and about 180, between about 180 and about 190, between about 190 and about 200, between about 200 and about 210, between about 210 and about 220, between about 220 and about 230, between about 230 and about 240, between about 240 and about 250, between about 250 and about 260, between about 260 and about 270, between about 270 and about 280, between about 280 and about 290, between about 290 and about 300, between about 300 and about 310, between about 310 and about 320, between about 320 and about 330, between about 330 and about 340, or between about 340 and about 250 amino acids in length.

In some aspects, the Scaffold Y comprises (i) GGKLSKKKKGYNVN (SEQ ID NO: 46), (ii) GAKLSKKKKGYNVN (SEQ ID NO: 47), (iii) GGKQSKKKKGYNVN (SEQ ID NO: 48), (iv) GGKLAKKKKGYNVN (SEQ ID NO: 49), (v) GGKLSKKKKGYSGG (SEQ ID NO: 50), (vi) GGKLSKKKKGSGGS (SEQ ID NO: 51), (vii) GGKLSKKKSGGSG (SEQ ID NO: 52), (viii) GGKLSKKKSGGSGG (SEQ ID NO: 53), (ix) GGKLSKKSGGSGGS (SEQ ID NO: 54), (x) GGKLSKSGGSGGSV (SEQ ID NO: 55), or (xi) GAKKSKKRFSFKKS (SEQ ID NO: 56).

In some aspects, the polypeptide sequence of a Scaffold Y useful for the present disclosure consists of (i) GGKLSKKKKGYNVN (SEQ ID NO: 46), (ii) GAKLSKKKKGYNVN (SEQ ID NO: 47), (iii) GGKQSKKKKGYNVN (SEQ ID NO: 48), (iv) GGKLAKKKKGYNVN (SEQ ID NO: 49), (v) GGKLSKKKKGYSGG (SEQ ID NO: 50), (vi) GGKLSKKKKGSGGS (SEQ ID NO: 51), (vii) GGKLSKKKSGGSG (SEQ ID NO: 52), (viii) GGKLSKKKSGGSGG (SEQ ID NO: 53), (ix) GGKLSKKSGGSGGS (SEQ ID NO: 54), (x) GGKLSKSGGSGGSV (SEQ ID NO: 255), or (xi) GAKKSKKRFSFKKS (SEQ ID NO: 56).

Non-limiting examples of the Scaffold Y useful for the present disclosure are listed below. In some embodiments, the Scaffold Y comprises an amino acid sequence set forth in Table 3. In some embodiments, the Scaffold Y consists of an amino acid sequence set forth in Table 3.

TABLE 3

| SEQ ID NO: | Scaffold Protein: GX2X3X4X5X6-ED |
|---|---|
| 57 | GGKLSKKKKGYNVNDEKAKEKDKKAEGAA |
| 58 | GGKLSKKKKGYNVNDEKAKEKDKKAEGA |
| 59 | GGKLSKKKKGYNVNDEKAKEKDKKAEG |
| 60 | GGKLSKKKKGYNVNDEKAKEKDKKAE |
| 61 | GGKLSKKKKGYNVNDEKAKEKDKKA |
| 62 | GGKLSKKKKGYNVNDEKAKEKDKK |
| 63 | GGKLSKKKKGYNVNDEKAKEKDK |
| 64 | GGKLSKKKKGYNVNDEKAKEKD |
| 65 | GGKLSKKKKGYNVNDEKAKEK |
| 66 | GGKLSKKKKGYNVNDEKAKE |
| 67 | GGKLSKKKKGYNVNDEKAK |
| 68 | GGKLSKKKKGYNVNDEKA |
| 69 | GGKLSKKKKGYNVNDEK |
| 70 | GGKLSKKKKGYNVNDE |
| 71 | GGKLSKKKKGYNVND |
| 46 | GGKLSKKKKGYNVN |
| 72 | GGKLSKKKKGYNV |
| 73 | GGKLSKKKKGYN |
| 74 | GGKLSKKKKGY |

TABLE 3-continued

| SEQ ID NO: | Scaffold Protein: GX2X3X4X5X6-ED |
|---|---|
| 75 | GGKLSKKKKG |
| 76 | GGKLSKKKK |
| 38 | GGKLSKKK |
| 11 | GGKLSKK |
| 99 | GAKKSKKRFSFKKSFKLSGFSFKKNKKEA |
| 77 | GAKKSKKRFSFKKSFKLSGFSFKKNKKE |
| 78 | GAKKSKKRFSFKKSFKLSGFSFKKNKK |
| 79 | GAKKSKKRFSFKKSFKLSGFSFKKNK |
| 80 | GAKKSKKRFSFKKSFKLSGFSFKKN |
| 81 | GAKKSKKRFSFKKSFKLSGFSFKK |
| 82 | GAKKSKKRFSFKKSFKLSGFSFK |
| 83 | GAKKSKKRFSFKKSFKLSGFSF |
| 84 | GAKKSKKRFSFKKSFKLSGFS |
| 85 | GAKKSKKRFSFKKSFKLSGF |
| 86 | GAKKSKKRFSFKKSFKLSG |
| 87 | GAKKSKKRFSFKKSFKLS |
| 88 | GAKKSKKRFSFKKSFKL |
| 89 | GAKKSKKRFSFKKSFK |
| 90 | GAKKSKKRFSFKKSF |
| 91 | GAKKSKKRFSFKKS |
| 92 | GAKKSKKRFSFKK |
| 93 | GAKKSKKRFSFK |
| 94 | GAKKSKKRFSF |
| 95 | GAKKSKKRFS |
| 96 | GAKKSKKRF |
| 97 | GAKKSKKR |
| 98 | GAKKSKK |
| 100 | GAKKAKKRFSFKKSFKLSGFSFKKNKKEA |
| 147 | GAKKAKKRFSFKKSFKLSGFSFKKNKKE |
| 148 | GAKKAKKRFSFKKSFKLSGFSFKKNKK |
| 149 | GAKKAKKRFSFKKSFKLSGFSFKKNK |
| 150 | GAKKAKKRFSFKKSFKLSGFSFKKN |
| 151 | GAKKAKKRFSFKKSFKLSGFSFKK |
| 152 | GAKKAKKRFSFKKSFKLSGFSFK |
| 153 | GAKKAKKRFSFKKSFKLSGFSF |
| 154 | GAKKAKKRFSFKKSFKLSGFS |
| 155 | GAKKAKKRFSFKKSFKLSGF |
| 156 | GAKKAKKRFSFKKSFKLSG |
| 157 | GAKKAKKRFSFKKSFKLS |
| 158 | GAKKAKKRFSFKKSFKL |
| 159 | GAKKAKKRFSFKKSFK |
| 160 | GAKKAKKRFSFKKSF |
| 161 | GAKKAKKRFSFKKS |
| 162 | GAKKAKKRFSFKK |
| 163 | GAKKAKKRFSFK |
| 164 | GAKKAKKRFSF |
| 165 | GAKKAKKRFS |
| 166 | GAKKAKKRF |
| 167 | GAKKAKKR |
| 168 | GAKKAKK |
| 101 | GAQESKKKKKKRFSFKKSFKLSGFSFKK |
| 102 | GAQESKKKKKKRFSFKKSFKLSGFSFK |
| 103 | GAQESKKKKKKRFSFKKSFKLSGFSF |
| 104 | GAQESKKKKKKRFSFKKSFKLSGFS |
| 105 | GAQESKKKKKKRFSFKKSFKLSGF |
| 106 | GAQESKKKKKKRFSFKKSFKLSG |
| 107 | GAQESKKKKKKRFSFKKSFKLS |
| 108 | GAQESKKKKKKRFSFKKSFKL |
| 109 | GAQESKKKKKKRFSFKKSFK |
| 110 | GAQESKKKKKKRFSFKKSF |
| 111 | GAQESKKKKKKRFSFKKS |
| 112 | GAQESKKKKKKRFSFKK |
| 113 | GAQESKKKKKKRFSFK |
| 114 | GAQESKKKKKKRFSF |
| 115 | GAQESKKKKKKRFS |
| 116 | GAQESKKKKKKRF |
| 117 | GAQESKKKKKKR |
| 118 | GAQESKKKKKK |
| 119 | GAQESKKKKK |
| 120 | GAQESKKKK |
| 121 | GAQESKKK |
| 122 | GAQESKK |
| 123 | GSQSSKKKKKKFSFKKPFKLSGLSFKRNRK |
| 124 | GSQSSKKKKKKFSFKKPFKLSGLSFKRNR |
| 125 | GSQSSKKKKKKFSFKKPFKLSGLSFKRN |
| 126 | GSQSSKKKKKKFSFKKPFKLSGLSFKR |
| 127 | GSQSSKKKKKKFSFKKPFKLSGLSFK |
| 128 | GSQSSKKKKKKFSFKKPFKLSGLSF |

TABLE 3-continued

| SEQ ID NO: | Scaffold Protein: GX2X3X4X5X6-ED |
|---|---|
| 129 | GSQSSKKKKKKFSFKKPFKLSGLS |
| 130 | GSQSSKKKKKKFSFKKPFKLSGL |
| 131 | GSQSSKKKKKKFSFKKPFKLSG |
| 132 | GSQSSKKKKKKFSFKKPFKLS |
| 133 | GSQSSKKKKKKFSFKKPFKL |
| 134 | GSQSSKKKKKKFSFKKPFK |
| 135 | GSQSSKKKKKKFSFKKPF |
| 136 | GSQSSKKKKKKFSFKKP |
| 137 | GSQSSKKKKKKFSFKK |
| 138 | GSQSSKKKKKKFSFK |
| 139 | GSQSSKKKKKKFSF |
| 140 | GSQSSKKKKKKFS |
| 141 | GSQSSKKKKKKF |
| 142 | GSQSSKKKKKK |
| 143 | GSQSSKKKKK |
| 144 | GSQSSKKKK |
| 145 | GSQSSKKK |
| 146 | GSQSSKK |

In some aspects, the Scaffold Y useful for the present disclosure does not contain an N-terminal Met. In some aspects, the Scaffold Y comprises a lipidated amino acid, e.g., a myristoylated amino acid, at the N-terminus of the scaffold protein, which functions as a lipid anchor. In some aspects, the amino acid residue at the N-terminus of the scaffold protein is Gly. The presence of an N-terminal Gly is an absolute requirement for N-myristoylation. In some aspects, the amino acid residue at the N-terminus of the scaffold protein is synthetic. In some aspects, the amino acid residue at the N-terminus of the scaffold protein is a glycine analog, e.g., allylglycine, butylglycine, or propargylglycine.

In other aspects, the lipid anchor can be any lipid anchor known in the art, e.g., palmitic acid or glycosylphosphatidylinositols. Under unusual circumstances, e.g., by using a culture medium where myristic acid is limiting, some other fatty acids including shorter-chain and unsaturated, can be attached to the N-terminal glycine. For example, in BK channels, myristate has been reported to be attached post-translationally to internal serine/threonine or tyrosine residues via a hydroxyester linkage. Membrane anchors known in the art are presented in the following table:

| Modification | Modifying Group |
|---|---|
| S-Palmitoylation | |
| N-Palmitoylation | |
| N-Myristoylation | |
| O-Acylation | |
| Farnesylation | |
| Geranylgeranylation | |

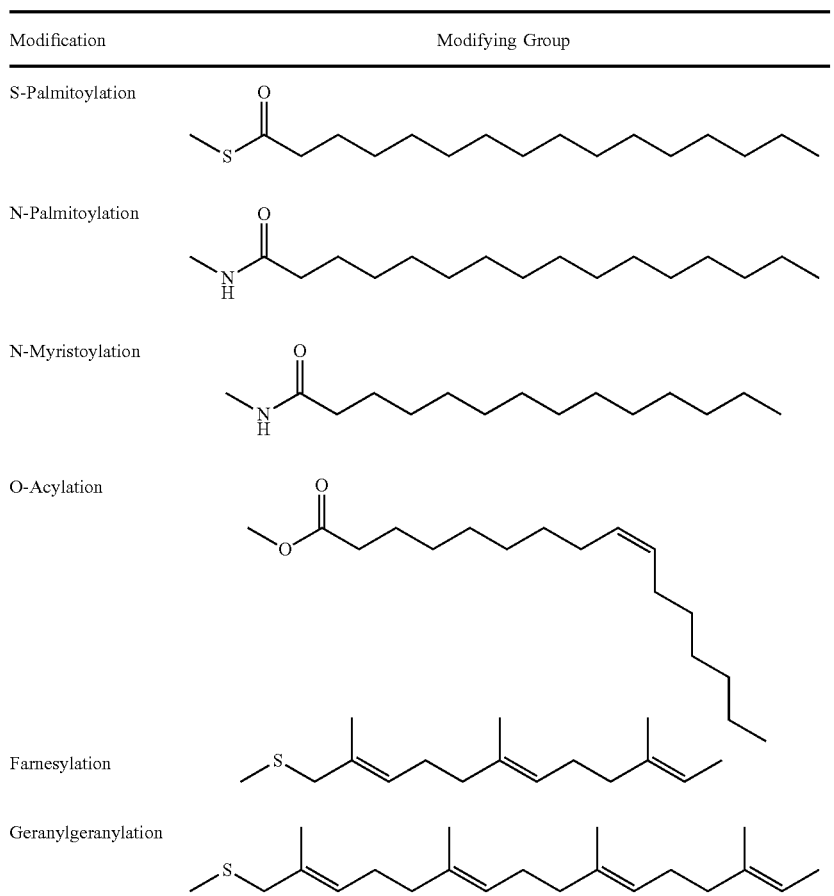

| Modification | Modifying Group |
|---|---|
| Cholesterol | 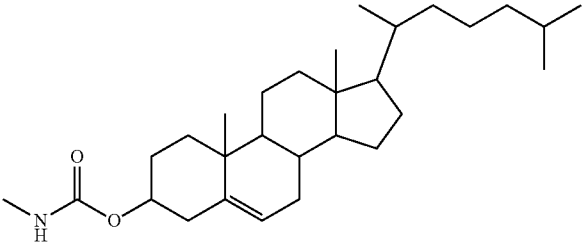 [SMILES: CNC(=O)OC1CCC2(C)C(=CCC3C2CCC2(C)C(C(C)CCCC(C)C)CCC32)C1] |

In some aspects, the biologically active molecule can be linked to a scaffold moiety either chemically or non-chemically. In some aspects, a biologically active molecule is linked to a scaffold moiety or an EV via a chemical linker, e.g., a maleimide moiety, a sulfhydryl linker, etc. As used herein the term "maleimide moiety" or "MM" refers to a bifunctional chemical moiety linking an EV, e.g., exosome, to a linker or a biologically active molecule and comprises the maleimide group:

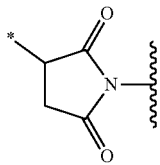 [SMILES: *C1CC(=O)N(*)C1=O]

wherein * indicates the attachment point to any thiol group on the EV, e.g., exosome, (e.g., a free thiol present in a Scaffold X), and the wavy line indicates the attachment site to the rest of the maleimide moiety. In some aspects, * indicates at attachment point to any thiol group on a payload and/or targeting moiety, and the wavy line indicates the attachment site to the rest of the maleimide moiety to the EV, e.g., exosome (e.g., a Scaffold X). In some aspects, the maleimide moiety attaches to a sulfur atom attached to the EV (e.g., exosome), e.g., a naturally occurring sulfur atom in a thiol group or a sulfur atom introduced via chemical modification or via mutation.

In some aspects, the maleimide moiety has the formula (I):

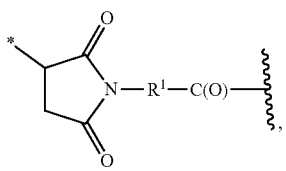

wherein
(i) $R^1$ is selected from the group consisting of $-C_{1-10}$ alkylene-, $-C_{3-8}$ carbocyclo-, $-O-(C_{1-8}$ alkylene)-, -arylene-, alkylene-arylene-, alkylene-, alkylene-($C_{3-8}$ carbocyclo)-, $-(C_{3-8}$ carbocyclo)-$C_{1-10}$ alkylene-, $-C_{3-8}$ heterocyclo-, $-C_{1-10}$ alkylene-($C_{3-8}$ heterocyclo)-, $-(C_{3-8}$ heterocyclo)-$C_{1-10}$ alkylene-, $-(CH_2CH_2O)_r-$, and $-(CH_2CH_2O)_r-CH_2-$;

(ii) r is an integer, e.g., from 1 to 10;
(iii) * indicates the attachment point to any available reactive sulfur atom, e.g., a sulfur in a thiol group, present on the EV (e.g., exosome); and,
(iv) the wavy line indicates the attachment site of the maleimide moiety to the biologically active molecule (i.e., payload).

In some aspects, $R^1$ is $-C_{1-8}$ alkylene-, $-C_{3-6}$ carbocyclo-, $-O-(C_{1-6}$ alkylene)-, -arylene-, $-C_{1-8}$ alkylene-arylene-, -arylene-$C_{1-8}$ alkylene-, $-C_{1-8}$ alkylene-($C_{3-6}$ carbocyclo)-, $-(C_{3-6}$ carbocyclo)-$C_{1-8}$ alkylene-, $-C_{3-6}$ heterocyclo-, $-C_{1-8}$ alkylene-($C_{3-6}$ heterocyclo)-, $-(C_{3-6}$ heterocyclo)-$C_{1-8}$ alkylene-, $-(CH_2CH_2O)_r-$, and $-(CH_2CH_2O)_r-CH_2-$; where r is an integer, e.g., from 1 to 10.

In some aspects, $R^1$ is $-(CH_2)_s-$, cyclopentyl, cyclohexyl, $-O-(CH_2)_s-$, -phenyl-, $-CH_2$-phenyl-, -phenyl-$CH_2-$, $-CH_2$-cyclopentyl-, -cyclopentyl-$CH_2-$, $-CH_2-$cyclohexyl-, -cyclohexyl-$CH_2-$, $-(CH_2CH_2O)_r-$, and $-(CH_2CH_2O)_r-CH_2-$; where r is an integer, e.g., from 1 to 6.

In some aspects, $R^1$ is $-(CH_2)_s-$, wherein s is, e.g., 4, 5, or 6.

In some aspects, the maleimide moiety has the formula (II), wherein $R^1$ is $-(CH_2)_5-$

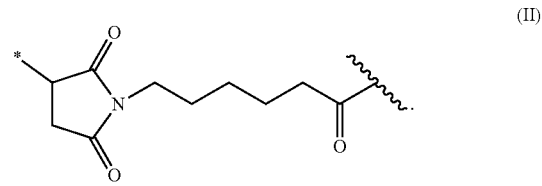 [SMILES: *C(=O)CCCCCN1C(=O)CC(*)C1=O]

In some aspects, the maleimide moiety has the formula (III), wherein $R^1$ is $-(CH_2CH_2O)_r-CH_2-$, and wherein r is 2:

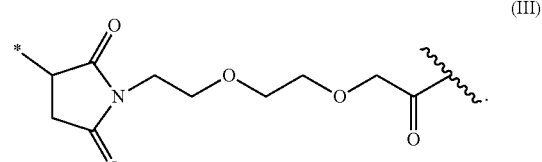

In some aspects, the maleimide moiety is covalently linked to a functional group present on the EV (e.g., exosome), wherein the functional group is a sulfhydryl (thiol) group. In one aspect, the sulfhydryl group is on a protein on the surface of the EV (e.g., exosome), e.g., Scaffold X, or a variant thereof. For example, in some aspects, the sulfhydryl group can be present on a thiol lipid, e.g., cholesterol-SH, DSPE-SH, or derivatives thereof, e.g., cholesterol-PEG-SH or DSPE-PEG-SH.

In some aspects, a payload is linked to a scaffold moiety on the exterior surface of the EV. In some aspects, the payload is linked to the scaffold moiety on the luminal surface of the EV. In some aspects, the scaffold moiety comprises sterol, GM1, a lipid, a vitamin, a small molecule, a peptide, or a combination thereof. In some aspects, the scaffold moiety comprises cholesterol. In some aspects, the scaffold moiety comprises a phospholipid, a lysophospholipid, a fatty acid, a vitamin (e.g., vitamin D and/or vitamin E), or any combination thereof. In some aspects, the payload is linked to the scaffold moiety by a linker.

In some aspects, linkers disclosed herein can be introduced into maleimide moieties using techniques known in the art (e.g., chemical conjugation, recombinant techniques, or peptide synthesis). In some aspects, the linkers can be introduced using recombinant techniques. In other aspects, the linkers can be introduced using solid phase peptide synthesis. In certain aspects, a maleimide moiety disclosed herein can contain simultaneously one or more linkers that have been introduced using recombinant techniques and one or more linkers that have been introduced using solid phase peptide synthesis or methods of chemical conjugation known in the art. In some aspects, a linker can comprise a cholesterol moiety. See, e.g., US 2008/0085869 A1, which is herein incorporated by reference in its entirety.

In some aspects, one or more linkers comprise smaller units (e.g., HEG, TEG, glycerol, C2 to C12 alkyl, and the like) linked together. In some aspects, the linkage is an ester linkage (e.g., phosphodiester or phosphorothioate ester) or other linkage. Examples of non-cleavable linkers that can be used with the present disclosure are known in the art, see, e.g., U.S. Pat. No. 7,569,657 B2; U.S. Pat. No. 8,465,730 B1; U.S. Pat. No. 7,087,229 B2; and U.S. Publ. No. 2014/0193849 A1, each of which is herein incorporated by reference in its entirety. In some aspects, the linker can be, e.g., maleimido caproyl (MC), maleimido propanoyl (MP), methoxyl polyethyleneglycol (MPEG), succinimidyl 4-(N-maleimidomethyl)-cyclohexane-1-carboxylate (SMCC), m-maleimidobenzoyl-N-hydroxysuccinimide ester (MB 5), succinimidyl 4-(p-maleimidophenyl)butyrate (SMPB), N-succinimidyl(4-iodoacetyl)aminobenzonate (SIAB), succinimidyl 6-[3-(2-pyridyldithio)-propionamide]hexanoate (LC-SPDP), 4-succinimidyloxycarbonyl-alpha-methyl-alpha-(2-pyridyldithio)toluene (SMPT), etc. (see, e.g., U.S. Pat. No. 7,375,078, which is herein incorporated by reference in its entirety).

In some aspects, the linker comprises acrylic phosphoramidite (e.g., ACRYDITE™), adenylation, azide (NHS Ester), digoxigenin (NHS Ester), cholesterol-TEG, I-LINKER™, an amino modifier (e.g., amino modifier C6, amino modifier C12, amino modifier C6 dT, or Uni-Link™ amino modifier), alkyne, 5' Hexynyl, 5-Octadiynyl dU, biotinylation (e.g., biotin, biotin (Azide), biotin dT, biotin-TEG, dual biotin, PC biotin, or desthiobiotin), thiol modification (thiol modifier C3 S-S, dithiol or thiol modifier C6 S-S), or any combination thereof. In some aspects, the linker is a cleavable linker. In some aspects, the linker comprises valine-alanine-p-aminobenzylcarbamate or valine-citrulline-p-aminobenzylcarbamate. In some aspects, the linker comprises (i) a maleimide moiety and (ii) valine-alanine-p-aminobenzylcarbamate or valine-citrulline-p-aminobenzylcarbamate.

IV. Targeting Moieties

In some aspects, the EV, e.g., exosome, comprises a targeting moiety, i.e., a biologically active molecule directing an EV, e.g., exosome, of the present disclosure to a specific cell type or tissue comprising, a target (e.g., a target protein such as receptor), wherein another payload (e.g., another biologically active molecule) can have a therapeutic, prophylactic, or diagnostic effect.

In some aspects, the targeting moiety is an exogenous targeting moiety is, e.g., an antibody or an antigen binding portion thereof, a protein or peptide that specifically binds to a protein (e.g., a receptor) present on the surface of a target cell or tissue.

In some aspects, a targeting moiety of the present disclosure specifically binds to a marker for a dendritic cell. In certain aspects, the marker is expressed only on dendritic cells. In some aspects, dendritic cells comprise a progenitor (Pre) dendritic cells, inflammatory mono dendritic cells, plasmacytoid dendritic cell (pDC), a myeloid/conventional dendritic cell 1 (cDC1), a myeloid/conventional dendritic cell 2 (cDC2), inflammatory monocyte derived dendritic cells, Langerhans cells, dermal dendritic cells, lysozyme-expressing dendritic cells (LysoDCs), Kupffer cells, non-classical monocytes, or any combination thereof. Markers that are expressed on these dendritic cells are known in the art. See, e.g., Collin et al., Immunology 154(1):3-20 (2018). In some aspects, the targeting moiety is a protein, wherein the protein is an antibody or a fragment thereof that can specifically bind to a marker selected from DEC205, CLEC9A, CLEC6, DCIR, DC-SIGN, LOX-1, MARCO, Clec12a, Clec10a, DC-asialoglycoprotein receptor (DC-ASGPR), DC immunoreceptor 2 (DCIR2), Dectin-1, macrophage mannose receptor (MMR), BDCA-2 (CD303, Clec4c), Dectin-2, Bst-2 (CD317), Langerin, CD206, CD11b, CD11c, CD123, CD304, XCR1, AXL, Siglec 6, CD209, SIRPA, CX3CR1, GPR182, CD14, CD16, CD32, CD34, CD38, CD10, or any combination thereof. In some aspects, a marker useful for the present disclosure comprises a C-type lectin like domain. In certain aspects, a marker is Clec9a and the dendritic cell is cDC1.

In some aspects, a targeting moiety disclosed herein can allow for greater uptake of an EV (e.g., exosome) by a cell expressing a marker specific for the targeting moiety (e.g., CD3: CD4+ T cell and/or CD8+ T cell; Clec9a: dendritic cells).

As described supra, a targeting moiety disclosed herein can comprise a peptide, an antibody or an antigen-binding fragment thereof, a chemical compound, or any combination thereof. In some aspects, the targeting moiety is a peptide that can specifically bind to Clec9a. See, e.g., Yan et al., Oncotarget 7(26): 40437-40450 (2016). For example, in certain aspects, the peptide comprises a soluble fragment of Clec9a. A non-limiting example of such a peptide is described in U.S. Pat. No. 9,988,431 B2, which is herein incorporated by reference in its entirety. In certain aspects, the peptide comprises a ligand (natural or synthetic) of Clec9a, such as those described in Ahrens et al., Immunity 36(4): 635-45 (2012); and Zhang et al., Immunity 36(4): 646-57 (2012). A non-limiting example of a peptide comprising a Clec9a ligand is described in International Publ. No. WO 2013/053008 A2, which is herein incorporated by reference in its entirety.

In some aspects, a targeting moiety of the present disclosure specifically binds to a marker for a T cell. In certain aspects, the T cell is a CD4+ T cell. In some aspects, the T cell is a CD8+ T cell. In some aspects, a targeting moiety disclosed herein binds to human CD3 protein or a fragment thereof. Sequences for human CD3 protein are known in the art. In some aspects, a targeting moiety disclosed herein can bind to both human and mouse CD3, including any variants thereof.

In some aspects, the targeting moiety is a peptide that can specifically bind to CD3. For example, in certain aspects, the peptide comprises a soluble fragment of CD3. In certain aspects, the peptide comprises a ligand (natural or synthetic) of CD3. In some aspects, the targeting moiety is an antibody or an antigen binding fragment thereof. In certain aspects, a targeting moiety is a single-chain Fv antibody fragment. In certain aspects, a targeting moiety is a single-chain F(ab) antibody fragment. In certain aspects, a targeting moiety is a nanobody. In certain aspects, a targeting moiety is a monobody.

In some aspects, an EV (e.g., exosome) disclosed herein comprises one or more (e.g., 2, 3, 4, 5, or more) targeting moieties. In certain aspects, the one or more targeting moieties are expressed in combination with other exogenous biologically active molecules disclosed herein (e.g., therapeutic molecule, adjuvant, or immune modulator). In some aspects, the one or more targeting moieties can be expressed on the exterior surface of the EV, e.g., exosome. Accordingly, in certain aspects, the one or more targeting moieties are linked to a scaffold moiety (e.g., Scaffold X) on the exterior surface of the EV, e.g., exosome. When the one or more targeting moieties are expressed in combination with other exogenous biologically active molecules (e.g., therapeutic molecule, adjuvant, or immune modulator), the other exogenous biologically active molecules can be expressed on the surface (e.g., exterior surface or luminal surface) or in the lumen of the EV, e.g., exosome.

V. Pretreatment Prior to Chromatography

In some embodiments, samples comprising EVs can be pretreated to make them suitable for chromatographic purification. Without being bound by a particular theory, pretreatment can make samples comprising EVs suitable for binding to ligands and/or purification by chromatography. Pretreatment can also provide certain physiological characteristics that make the samples suitable for certain ligand interactions. For example, in some embodiments, pretreatment can provide a pH, temperature, salt concentration, salt type, polarity, or any combination therein, that is desirable for ligand binding and/or chromatographic purification.

In some embodiments, pretreatment can comprise clarification, nuclease treatment, ultrafiltration/diafiltration, or any combination thereof. In some embodiments, pretreatment occurs prior to any chromatography. In some embodiments, pretreatment occurs prior to the CEX process described herein. In some embodiments, pretreatment occurs prior to the AEX process described herein. In some embodiments, pretreatment occurs prior to the MMC process described herein.

In certain embodiments, pretreatment of the samples comprising EVs comprises clarification. In some embodiments, clarification comprises depth filtration, nuclease treatment, centrifugation, acoustic separation, flocculation, or any combination thereof. In some embodiments, pretreatment of the samples comprising EVs comprises clarification wherein the clarification comprises depth filtration. Depth filtration is a purification method which uses a porous filtration medium (i.e., "depth filter medium") that retains contaminants throughout the medium rather than just on the medium's surface and thus can retain a larger number of contaminants before becoming clogged. Depth filtration relies on adsorption and/or mechanical entrapment throughout the depth filter medium. In some embodiments, the samples comprising EVs are pretreated by clarification, wherein the clarification is depth filtration, prior to the CEX process. In some embodiments, the samples comprising EVs are pretreated by clarification, wherein the clarification is depth filtration, prior to the AEX process. In some embodiments, the samples comprising EVs are pretreated by clarification, wherein the clarification is depth filtration, prior to the MMC process.

There are various designs for depth filters. In some embodiments, the depth filtration is performed with a pad or a panel. In some embodiments, the depth filtration is performed with a deep bed sand filter. In some embodiments, the depth filtration is performed with a lenticular design comprising stacked design. In some embodiments, depth filtration is performed with a thick filter wound around a perforated cylinder of depth filter medium that surrounds a central core. One of ordinary skill in the art will recognize that the type and condition of depth filtration (for example, the type of filter and the number of filters) can be selected and adjusted depending on the source, volume, purity, and EV concentration of the sample.

In some embodiments, samples are pretreated with depth filtration using uncharged materials as filter mediums. Without being bound by a particular theory, filters that contain diatomaceous earth and filters that contain positively charged materials tend to provide lower yields of EVs as the negatively charged EVs tend to bind to the filters. In some embodiments, the depth filtration comprises uncharged filter materials such as cellulose, cellulose acetate, cellulose esters, other cellulose derivatives, polypropylene, polyethylene, polyethersulfone, nylon, polyvinylidene fluoride, glass fiber, polytetrafluorethylene, methacrylate, and/or other uncharged polymers. The particular uncharged material can be selected based on load, shape, size, and distribution of EVs to be filtered. In addition, materials can be selected based on the physiological properties of the EVs, the production cell line, additional pretreatment steps, particular contaminants, or a number of other factors. In some embodiments, a large-scale depth filtration system comprising multiple housings and cartridges can be used for large scale purification of EVs.

In some embodiments, the porosity and particle-retention of the depth filter medium are controlled by the length and density of the filter bed. The more dense and compacted the filter bed, the lower the permeability, which provides higher retention of small particles. In some embodiments, the porous depth filter can have an average pore size from about 0.1 to about 100 µm. In some embodiments, the porous depth filter can have an average pore size from about 0.2 to about 90 µm. In some embodiments, the porous depth filter can have an average pore size from about 0.3 to about 80 µm. In some embodiments, the porous depth filter can have an average pore size from about 0.4 to about 70 µm. In some embodiments, the porous depth filter can have an average pore size from about 0.5 to about 60 µm. In some embodiments, the porous depth filter can have an average pore size from about 0.6 to about 50 µm. In some embodiments, the porous depth filter can have an average pore size from about 0.7 to about 60 µm. In some embodiments, the porous depth filter can have an average pore size from about 0.8 to about 50 µm. In some embodiments, the porous depth filter can have an average pore size from about 0.9 to about 40 µm. In some embodiments, the depth filter can have an average pore size from about 0.5 and about 30 µm. In some embodiments, the porous depth filter can have an average pore size from about 1 to about 30 µm. In some embodiments, the porous depth filter can have an average pore size from about 1.1 to about 20 µm. In some embodiments, the porous depth filter can have an average pore size from about 1.2 to about 10 µm. In some embodiments, the porous depth filter can have an average pore size or from about 1.3 to about 5 µm. In further embodiments, the porous depth media can have a pore size less than about 1 µm.

In some embodiments, depth filtration is performed with a depth filter selected from Emphaze (3M), Zeta Plus S (3M), PDH4 (Pall), Polysep II (MilliporeSigma), XOSP (MilliporeSigma), COSP (MilliporeSigma), CR40 (MilliporeSigma), ZetaPlus activated carbon (3M), zero charge (MilliporeSigma), DOSP (MilliporeSigma), V100 (Pall), Bio20 (Pall), Bio10 (Pall), glass fiber (Pall), XOHC (MilliporeSigma), A1HC (MilliporeSigma), GF+ (Sartorius), and P-series filters (Pall). In some embodiments, two or more depth filters can be used in the depth filtration. In some embodiments, the two or more depth filters have different pore structures. In some embodiments, the two or more depth filters are arranged in series. For example, a filter with a larger structure used to remove cells and cell debris can be followed by a filter with smaller pore structure used to remove smaller contaminants such as colloidal matter. In some embodiments, two or more depth filters can be used sequentially. In some embodiments, the two or more depth filters are arranged in parallel. In some embodiments, the depth filtration uses three depth filters. In some embodiments, the depth filtration uses four depth filters. In some embodiments, the depth filtration uses five depth filters. In some embodiments, the depth filtration uses six depth filters. In some embodiments, the depth filtration uses seven depth filters. In some embodiments, the depth filtration uses eight depth filters. In some embodiments, the depth filtration uses nine depth filters. In some embodiments, the depth filtration uses ten depth filters. In some embodiments, the depth filtration uses more than ten depth filters.

In some embodiments, the depth filter comprises a single layer. In some embodiments, the depth filter comprises combinations of media layers that are selected based on origin and quality of the sample. Examples include, but are not limited to, dual-layer graded depth filters, which are formed by layering two sheets of filter media of differing pore sizes into lenticular style cartridges. In some embodiments, a filter with a larger pore structure can be placed upstream to capture large cells and debris, while a filter with a smaller pore structure can be placed downstream to remove finer particles such as colloids. Dual-layer depth filters extend depth filtration capacity and improve protection of downstream membranes from lodging with impurities.

In some embodiments, the depth filtration methods provided herein can be used to purify EVs from products produced in a bioreactor or bioreactor-like device, prior to one or more chromatography processes described herein. In certain embodiments, after production the contents of the bioreactor can be passed over a series of uncharged cellulose depths filters with decreasing pore sizes to remove cells and cell debris while allowing EVs to pass through the filter.

In some embodiments, the contents of the bioreactor can be pretreated before undergoing depth filtration. In certain embodiments, the pretreatment can change the size of the EVs prior to depth filtration. In some embodiments, pretreatment comprises treating with an agent selected from acetic acid, citric acid, salts such as ammonium sulfate, potassium sulfate, or potassium bisulfate, cationic polymers such as chitosan, pDADMAC or PEI, and other artificial polymers such as polyethylene glycol.

In some embodiments, after subjecting the samples comprising EVs to clarification, the sample can be further processed by additional purification methods to remove process- and product-related impurities. In some embodiments, the impurities can include host cell proteins, DNA, aggregates, fragments, viruses and other small-molecule EV impurities. In some embodiments, the additional purification steps can isolate a specific subset of EVs having desired physiological properties. In some embodiments, the desired physiological properties can be related to biodistribution, cellular uptake, half-life, pharmacodynamics, potency, dosing, immune response, loading efficiency, stability, size, charge density, or reactivity to other compounds.

In certain embodiments, depth filtration can be conducted before or after one or more of the chromatographic steps described herein to further purify the samples comprising EVs. In some embodiments, the samples comprising EVs are subjected to depth filtration after chromatography. In some embodiments, the depth filtration conditions used during clarification are different from those used in the depth filtration conducted after chromatography.

In some embodiments, the pretreatment step comprises contacting the sample comprising EVs with nuclease to digest nucleic acid associated with EVs. In some embodiments, the samples comprising EVs can be pretreated by contacting with nuclease prior to the CEX process. In some embodiments, the samples comprising EVs can be pretreated by contacting with nuclease prior to the AEX process. In some embodiments, the samples comprising EVs can be pretreated by contacting the sample with nuclease prior to the MMC process. In some embodiments, the sample comprising EVs can be clarified prior to contacting the sample with nuclease. In some embodiments, the sample comprising EVs can be clarified using depth filtration prior to contacting the sample with nuclease.

In some embodiments, the nuclease can be a DNase, an RNase, or a mixture of both. In some embodiments, the nuclease can be BENZONASE®, deoxynuclease I, deoxynuclease II, micrococcal nuclease, RNase A, RNase H, RNase III, RNase L, RNase P, RNase PhyM, RNase T1, RNase T2, RNase U2, or RNase V. In some embodiments, the nuclease can be BENZONASE® or DENARASE®. The present methods can also require a nuclease digestion for a period of time that allows for complete digestion of nucleic acid. In some aspects, the nuclease digestion occurs for greater than 1 hour. In some aspects, the nuclease digestion occurs for greater than 2 hours. In some aspects, the nuclease digestion occurs for greater than 2 hours. In some aspects, the nuclease digestion occurs for greater than 3 hours. In some aspects, the nuclease digestion occurs for greater than 4 hours. In some aspects, the nuclease digestion occurs for greater than 5 hours. In some aspects, the nuclease digestion occurs for greater than 6 hours. In some aspects, the nuclease digestion occurs for greater than 7 hours. In some aspects, the nuclease digestion occurs for greater than 8 hours. In some aspects, the nuclease digestion occurs for greater than 15 hours. In some aspects, the nuclease digestion occurs for greater than 2 hours. In some aspects, the nuclease digestion occurs for greater than 20 hours.

A cofactor can also be added to the nuclease to improve and/or retain enzyme activity of the nuclease. In some aspects, the nuclease requires magnesium. In some aspects, the cofactor is added in a salt form such as magnesium chloride. In some aspects, the magnesium chloride is added at a concentration of from about 1 mM to about 1000 mM.

In some aspects, the magnesium chloride is added at a concentration of from about 1 mM to about 100 mM. In some aspects, the magnesium chloride is added at a concentration of from about 1 mM to about 10 mM, from about 1 mM to about 4 mM, from about 1.5 mM to about 3.5 mM, from about 1.5 mM to about 3 mM, from about 1.5 mM to about 2.5 mM, from about 1.5 mM to about 2 mM, or from about 2 mM to about 3 mM. In some aspects, the magnesium chloride is added at a concentration of about 1 mM, about 2 mM, about 3 mM, or about 4 mM. In some aspects, the magnesium chloride is added at a concentration of about 1 mM. In some aspects, the magnesium chloride is added at a concentration of about 2 mM. In some aspects, the magnesium chloride is added at a concentration of about 5 mM. In some aspects, the magnesium chloride is added at a concentration of about 10 mM. In some aspects, the magnesium chloride is added at a concentration of about 50 mM. In some aspects, the magnesium chloride is added at a concentration of about 100 mM.

In some embodiments, the nuclease is mixed with the sample comprising EVs to have a final concentration from about 5 U/ml to about 500 U/ml. In some embodiments, the final concentration of the sample comprising EVs and nuclease can be from about 10 U/ml to about 200 U/ml. In some embodiments, the final concentration of the sample comprising EVs and nuclease can be from about 20 U/ml to about 150 U/ml. In some embodiments, the final concentration of the sample comprising EVs and nuclease can be from about 50 U/ml to about 100 U/ml. In some embodiments, the final concentration of the sample comprising EVs and nuclease can be about 100 U/ml.

In some embodiments, the sample comprising EVs can be pretreated by ultrafiltration/diafiltration (UF/DF). The process of UF/DF is often used to concentrate a therapeutic product and exchange the buffer in which it resides. In some embodiments of the present disclosure, the process of UF/DF can be used to remove impurities from EVs. In some embodiments, the process comprises using excipients to remove impurities from the surface of the EVs. In some embodiments, the impurities, which are smaller than the pore size of the UF/DF membrane, permeate through the membrane and are removed. In some embodiments, a subsequent diafiltration step can be used to remove the excipient. In some embodiments, the sample comprising EVs can be pretreated by UF/DF prior to the CEX process. In some embodiments, the sample comprising EVs can be pretreated by UF/DF prior to the AEX process. In some embodiments, the sample comprising EVs can be pretreated by UF/DF prior to the MMC process. In some embodiments, the sample comprising EVs can be contacted with nuclease before pretreatment with UF/DF. In some embodiments, the sample comprising EVs can be clarified by depth filtration before pretreatment with UF/DF. In some embodiments, the sample comprising EVs can be clarified by depth filtration, contacted with nuclease, then pretreated with UF/DF.

In certain embodiments, the UF/DF removes cells and/or cell debris from the sample comprising the EVs. In some embodiments, the filtration may be conducted with successive filtrations. In some embodiments, the successive filtrations occur through filters with decreasing porosity. In some embodiments, the process of UF/DF comprises filtration through one or more filters that have a porosity above 0.2 In some embodiments, the process of UF/DF comprises filtration through one or more filters that have a porosity of from about 0.1 μm to about 20 In some embodiments, the process of UF/DF comprises filtration through one or more filters that have a porosity about 0.2 μm to about 10 In some embodiments, the process of UF/DF comprises a first filtration through a filter that can have a porosity of from about 8 μm to about 12 In some embodiments, the process of UF/DF comprises a second filtration through a filter that can have a porosity of from about 0.8 μm to about 1.2 In some embodiments, the process of UF/DF comprises a third filtration through a filter that can have a porosity of from about 0.4 μm to about 0.6 In some embodiments, the process of UF/DF comprises a fourth filtration through a filter that can have a porosity of from about 0.2 μm to about 0.3 μm.

In some embodiments, the UF/DF filtration can comprise a pre-filtration. In some embodiments, the pre-filtration can be conducted on a pre-filter. In some embodiments, the pre-filter comprises cellulose acetate, polypropylene, and/or polyether sulfone. In some embodiments, the pre-filter comprises cellulose acetate. In some embodiments, the pre-filter has a porosity from about 1 μm to about 5 μm. In some embodiments, the pre-filter has a porosity from about 2 μm to about 4 μm. In some embodiments, the pre-filter has a porosity of about 3 μm.

In some embodiments, the process of ultrafiltration can be used to concentrate the sample comprising EVs. In some embodiments, the process of ultrafiltration can be used to purify the sample comprising EVs. In some embodiments, a sample comprising EVs can be subjected to an ultrafiltration. In some embodiments, the sample comprising EVs is subjected to ultrafiltration after treatment with a nuclease. In some embodiments, the sample comprising EVs is pretreated by clarification with depth filtration prior to ultrafiltration. In some embodiments, the sample comprising EVs is pretreated by clarification with depth filtration and treated with nuclease prior to ultrafiltration.

Tangential ultrafiltration (also called tangential flow filtration, or "TFF") comprises concentrating and fractionating a solution between two compartments (filtrate and retentate), separated by membranes that have molecular weight cut-off thresholds. The separation can be carried out by applying a flow in the retentate compartment and a transmembrane pressure between this compartment and the filtrate compartment. In some embodiments, the sample comprising EVs is subjected to ultrafiltration wherein the ultrafiltration is TFF. In instances where a large scale purification is being conducted, the TFF process can be repeated multiple times. In some embodiments, the TFF process is not repeated. In some embodiments, the TFF can be repeated at least two times, at least three times, at least four times, at least five times, at least six times, at least seven times, at least eight times, at least nine times, at least 10 times, at least 11 times, at least 12 times, at least 13 times, at least 14 times, at least 15 times, at least 16 times, at least 17 times, at least 18 times, at least 19 times, at least 20 times, at least 21 times, at least 22 times, at least 23 times, at least 24 times, at least 25 times, at least 26 times, at least 27 times, at least 28 times, at least 29 times, at least 30 times, at least 31 times, at least 32 times, at least 33 times, at least 34 times, at least 35 times, at least 36 times, at least 37 times, at least 38 times, at least 39 times, or at least 40 times. In some embodiments, the TFF can be repeated about four times. In some embodiments, the TFF can be repeated about five times. In some embodiments, the TFF can be repeated about six times. In some embodiments, the TFF can be repeated about seven times.

In some embodiments, the TFF system comprises spiral membranes (Millipore, Amicon), flat membranes, and/or hollow fibers (Amicon, Millipore, Sartorius, Pall, GF, Sepracor). In some embodiments, the ultrafiltration system comprises hollow fibers. In some embodiments, the hollow fibers are selected from modified polyethersulfone (Spectrum), polysulfone (Spectrum, GE), mixed cellulose ester (Spectrum), and/or polyethersulphone (Spectrum, GE) fibers.

In some embodiments, the TFF membranes can have a molecular weight cut-off threshold below 1500 kDa. In some embodiments, the TFF membranes can have a molecular weight cut-off threshold of from about 300 kDa to about 1000 kDa. In some embodiments, the TFF membranes can have a molecular weight cut-off threshold of about 300 kDa. In some embodiments, the TFF membranes can have a molecular weight cut-off threshold of about 500 kDa. In some embodiments, the TFF membranes can have a molecular weight cut-off threshold of about 750 kDa. In some embodiments, the TFF membranes can have a molecular weight cut-off threshold of about 1000 kDa. In some embodiments, the TFF membranes can have a molecular weight cut-off threshold of from about 10 kDa to about 100 kDa. In some embodiments, the TFF membranes can have a molecular weight cut-off threshold of about 10 kDa. In some embodiments, the TFF membranes can have a molecular weight cut-off threshold of about 30 kDa. In some embodiments, the TFF membranes can have a molecular weight cut-off threshold of about 50 kD. In some embodiments, the TFF membranes can have a molecular weight cut-off threshold of about 70 kDa. In some embodiments, the TFF membranes can have a molecular weight cut-off threshold of about 100 kDa. In some embodiments, the TFF membranes can have a molecular weight cut-off threshold of about 50 nm.

In some embodiments, the sample comprising EVs is subjected to diafiltration. In certain embodiments, the sample comprising the EVs is concentrated by TFF before being subjected to diafiltration. In some embodiments, diafiltration is used to exchange the buffer of the sample comprising EVs with formulation buffer. In some embodiments, diafiltration can be conducted by ultrafiltration. In some embodiments, diafiltration can be conducted by chromatography. In some embodiments, diafiltration can be conducted by ultracentrifugation. In some embodiments, diafiltration can be conducted through a dialysis bag.

In some embodiments, diafiltration can be performed with an ultrafiltration system. In some embodiments, where the sample comprising EVs has been concentrated by ultrafiltration, the diafiltration step may be combined easily therewith, using the same methodology. In certain embodiments, the samples comprising EVs are diafiltered by ultrafiltration using the same TFF membrane as used in the concentration step. This embodiment is advantageous since both steps can be performed essentially in the same device with limited intervention and manipulation of the EVs, i.e., by mere modification of the products introduced into the hollow fiber.

In some embodiments, the diafiltration filter can have a cut-off between about 30 kDa to about 1000 kDa. In some embodiments, the diafiltration filter can have a cut-off between about 200 kDa to about 750 kDa. In some embodiments, the diafiltration filter can have a molecular weight cut-off of about 100 kDa. In some embodiments, the diafiltration filter can have a molecular weight cut-off of about 300 kDa. In some embodiments, the diafiltration filter can have a molecular weight cut-off of about 750 kDa. In some embodiments, the diafiltration filter can have a molecular weight cut-off of about 750 kDa.

In some embodiments, the volume of buffer can be from about 1 to about 20 times the volume of the EV concentrate formed in the ultrafiltration. In some embodiments, the volume of buffer can be from about 1 to about 10 times the volume of EV concentrate formed in the ultrafiltration.

In some embodiments, the excipient comprises one or more excipients. In some embodiments, the excipient is selected from arginine, lysine, glycine, histidine, calcium, sodium, lithium, potassium, iodide, magnesium, iron, zinc, manganese, urea, propylene glycol, aluminum, ammonium, guanidinium polyethylene glycol, EDTA, EGTA, a detergent, chloride, sulfate, carboxylic acids, sialic acids, phosphate, acetate, glycine, borate, formate, perchlorate, bromine, nitrate, dithiothreitol, beta mercaptoethanol, tri-n-butyl phosphate, and/or mixtures thereof.

In some embodiments, the excipient can be a detergent. In some embodiments, the detergent can be selected from cetyl trimethylammonium chloride, octoxynol-9, TRITON™ X-100 (i.e., polyethylene glycol p-(1,1,3,3-tetramethylbutyl)-phenyl ether) and TRITON™ CG-110 available from Sigma-Aldrich; sodium dodecyl sulfate; sodium lauryl sulfate; deoxycholic acid; Polysorbate 80 (i.e., Polyoxyethylene (20) sorbitan monooleate); Polysorbate 20 (i.e., Polyoxyethylene (20) sorbitan monolaurate); alcohol ethoxylate; alkyl polyethylene glycol ether; decyl glucoside; octoglucosides; SafeCare; ECOSURF™ EH9, ECOSURF™ EH6, ECOSURF™ EH3, ECOSURF™ SA7, and ECOSURF™ SA9 available from DOW Chemical; LUTENSOL™ M5, LUTENSOL™ XL, LUTENSOL™ XP and APG™ 325N available from BASF; TOMADOL™ 900 available from AIR PRODUCTS; NATSURF™ 265 available from CRODA; SAFECARE™ 1000 available from Bestchem, TERGITOL™ L64 available from DOW; caprylic acid; CHEMBETAINE™ LEC available from Lubrizol; and/or Mackol DG.

In certain embodiments, UF/DF can be conducted before or after one or more of the chromatographic steps described herein to further purify the samples comprising EVs. In some embodiments, the samples comprising EVs are pretreated with TFF and are also subjected to TFF after chromatography. In some embodiments, the TFF conditions during pretreatment are the same as those used in the TFF performed after chromatography. In some embodiments, the TFF conditions during pretreatment are different from those used in the TFF after chromatography.

In some embodiments, the present methods include the following:
(i) subjecting a sample comprising the EVs to a clarification process, e.g., a depth filtration (depth-filtration processed sample);
(ii) contacting the depth-filtration processed sample with a CEX resin (CEX processed sample);
(iii) contacting the CEX-processed sample with an AEX resin (AEX processed sample); and
(iv) contacting the AEX-processed sample with a MMC resin (MMC processed sample).

In other embodiments, the present methods include the following:
(i) subjecting a sample comprising EVs to a nuclease (nuclease processed sample);
(ii) subjecting the nuclease treated sample to ultrafiltration and/or diafiltration (UF/DF processed sample);
(iii) contacting the UF/DF treated sample with a CEX resin (CEX processed sample);
(iv) contacting the CEX-processed sample with an AEX resin (AEX processed sample); and
(v) contacting the AEX-processed sample with a MMC resin (MMC processed sample).

In other embodiments, the present methods include the following:

(i) subjecting a sample comprising EVs to ultrafiltration and/or diafiltration (UF/DF processed sample);
(ii) contacting the UF/DF treated sample with a CEX resin (CEX processed sample);
(iii) contacting the CEX-processed sample with an AEX resin (AEX processed sample); and
(iv) contacting the AEX-processed sample with a MMC resin (MMC processed sample).

In other embodiments, the present methods include the following:
(i) subjecting a sample comprising EVs to a nuclease (nuclease processed sample);
(ii) contacting the UF/DF treated sample with a CEX resin (CEX processed sample);
(iii) contacting the CEX-processed sample with an AEX resin (AEX processed sample); and
(iv) contacting the AEX-processed sample with a MMC resin (MMC processed sample).

In other embodiments, the present methods include the following:
(i) subjecting a sample comprising the EVs to a depth filtration (depth-filtration processed sample);
(ii) subjecting the nuclease treated sample to ultrafiltration and/or diafiltration (UF/DF processed sample);
(iii) contacting the UF/DF treated sample with a CEX resin (CEX processed sample);
(iv) contacting the CEX-processed sample with an AEX resin (AEX processed sample); and
(v) contacting the AEX-processed sample with a MMC resin (MMC processed sample).

In other embodiments, the present methods include the following:
(i) subjecting a sample comprising the EVs to a depth filtration (depth-filtration processed sample);
(ii) subjecting the depth filtered sample to a nuclease (nuclease processed sample);
(iii) subjecting the nuclease treated sample to ultrafiltration and/or diafiltration (UF/DF processed sample);
(iv) contacting the UF/DF treated sample with a CEX resin (CEX processed sample);
(v) contacting the CEX-processed sample with an AEX resin (AEX processed sample); and
(vi) contacting the AEX-processed sample with a MMC resin (MMC processed sample).

In other embodiments, the present methods include the following:
(i) subjecting a sample comprising the EVs to a depth filtration (depth-filtration processed sample);
(ii) subjecting the depth filtered sample to a nuclease (nuclease processed sample);
(iii) subjecting the nuclease treated sample to ultrafiltration and/or diafiltration (UF/DF processed sample);
(iv) contacting the UF/DF treated sample with a CEX resin (CEX processed sample);
(v) contacting the CEX-processed sample with an AEX resin (AEX processed sample); and
(vi) contacting the AEX-processed sample with a MMC resin (MMC processed sample), wherein the pH of a CEX loading buffer in the CEX process is lower than the pH of an AEX loading buffer in the AEX process.

VI. Incubation and/or Storage

The present methods can also include one or more incubation and/or storage steps during production and bioprocessing in order to maintain product quality, and/or to further improve product quality. In some aspects, an incubation and/or storage step occurs during pretreatment (i.e, before, during, or after a clarification step, nuclease treatment, ultrafiltration/diafiltration, or any combination thereof). In some aspects, an incubation and/or storage step occurs after ultrafiltration/diafiltration but before chromatography (i.e., AEX, CEX, or MMC chromatography). In some aspects, an incubation and/or storage step occurs between CEX and AEX chromatography, between AEX and CEX chromatography, between CEX and MMC chromatography, or between AEX and MMC chromatography. The methods of the present disclosure can also include multiple incubation and/or storage steps. The methods can include one incubation or storage step, two incubation and/or storage steps, three incubation and/or storage steps, four incubation and/or storage steps, or five incubation and/or storage steps. In some aspects, an incubation and/or storage step occurs for about 1 day to about 10 days. In some aspects, an incubation and/or storage step occurs for about 1 day to about 8 days. In some aspects, an incubation and/or storage step occurs for about 1 day to about 6 days, about 1 day to about 10 days, about 1 day to about 15 days, about 1 day to about 2 days, less than or equal to about 7 days, less than or equal to about 4 days, less than or equal to about 4 days, less than or equal to about 72 hours, less than or equal to about 48 hours, or less than or equal to about 24 hours. The temperature of the incubation and/or storage step can also be modified to ensure proper product quality. For example, the temperature of the incubation and/or storage step can be between about 15° C. and about 25° C. in order to allow for a complete digestion of nucleic acid present in a sample by an added nuclease during a pretreatment step. In some aspects, an incubation and/or storage step occurs at a temperature of about 1° C. to about 25° C., about 2° C. to about 20° C., about 2° C. to about 15° C., about 2° C. to about 10° C., about 2° C. to about 8° C., about 15° C. to about 25° C., about 15° C. to about 20° C., or about 20° C. to about 25° C.

VII. Post Treatment after Chromatographies

The present methods also include one or more post treatment methods after subjecting the sample comprising EVs to the chromatographies described herein. In some embodiments, the post treatment can be ultrafiltration/diafiltration (UF/DF). The UF/DF is used to concentrate the EVs purified by the chromatography steps described herein and exchange the buffer in the chromatography purified EVs. In certain embodiments of the present disclosure, the process of UF/DF can be used to further remove impurities from the chromatography purified EVs. In some embodiments, the sample comprising EVs can be clarified prior to the UF/DF. In some embodiments, the sample comprising EVs can be clarified by depth filtration prior to the UF/DF.

In some embodiments, the UF/DF in the post treatment process is the same as the UF/DF in the pre-treatment process described above. In some embodiments, the UF/DF in the post treatment process is different from the UF/DF in the pre-treatment process described above. In some embodiments, the post treatment process includes a tangential flow filtration. The TFF in the post treatment process (TFF2) can be the same as the TFF in the pre-treatment (TFF1). In other embodiments, the TFF in the post treatment process (TFF2) is different from the TFF in the pre-treatment (TFF1).

In some embodiments, the present methods include the following:
(i) contacting a sample with a CEX resin (CEX processed sample);

(ii) contacting the CEX-processed sample with an AEX resin (AEX processed sample);
(iii) contacting the AEX-processed sample with a MMC resin (MMC processed sample); and
(iv) subjecting the MMC processed sample to a UF/DF.

In some embodiments, the present methods include the following:
(i) subjecting a sample comprising EVs in a pre-treatment process,
(ii) contacting the pre-treated sample with a CEX resin (CEX processed sample);
(iii) contacting the CEX-processed sample with an AEX resin (AEX processed sample);
(iv) contacting the AEX-processed sample with a MMC resin (MMC processed sample); and
(v) subjecting the MMC processed sample to a UF/DF.

In some embodiments, the present methods include the following:
(i) subjecting a sample comprising EVs to ultrafiltration and/or diafiltration (UF/DF processed sample);
(ii) contacting the UF/DF treated sample with a cation exchange chromatography (CEX) resin (CEX processed sample);
(iii) contacting the CEX-processed sample with an anion exchange chromatography (AEX) resin (AEX processed sample);
(iv) contacting the AEX-processed sample with mixed-mode chromatography (MMC) resin (MMC processed sample); and
(v) subjecting the MMC processed sample to a UF/DF.

In some embodiments, the present methods include the following:
(i) subjecting a sample comprising the EVs to a depth filtration (depth-filtration processed sample);
(ii) subjecting the depth filtered sample to a nuclease (nuclease processed sample);
(iii) subjecting the nuclease treated sample to ultrafiltration and/or diafiltration (UF/DF processed sample);
(iv) contacting the UF/DF treated sample with a CEX resin (CEX processed sample);
(v) contacting the CEX-processed sample with an AEX resin (AEX processed sample);
(vi) contacting the AEX-processed sample with a MMC resin (MMC processed sample); and
(vii) subjecting the MMC processed sample to a UF/DF.

In some embodiments, the present methods include the following:
(i) subjecting a sample comprising the EVs to a depth filtration (depth-filtration processed sample);
(ii) subjecting the depth filtered sample to a nuclease (nuclease processed sample);
(iii) subjecting the nuclease treated sample to ultrafiltration and/or diafiltration (UF/DF processed sample);
(iv) contacting the UF/DF treated sample with a CEX resin (CEX processed sample);
(v) contacting the CEX-processed sample with an AEX resin (AEX processed sample);
(vi) contacting the AEX-processed sample with a MMC resin (MMC processed sample); and
(vii) subjecting the MMC processed sample to a UF/DF, wherein the pH of a CEX loading buffer is lower than the pH of an AEX loading buffer.

VIII. Extracellular Vesicles Purified by Present Methods

The present disclosure also includes extracellular vesicles (EVs) purified by the present disclosure. In some embodiments, the EVs purified by the present methods include lower impurities, e.g., total protein impurities, than EVs purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In other embodiments, the EVs purified by the present methods include lower perlecan protein level than EVs purified by an AEX process or an AEX process followed by a hydrophobic interaction chromatography (HIC) process as measured by an AlphaLISA. In other embodiments, the EVs purified by the present methods include lower agrin protein level than EVs purified by an AEX process or an AEX process followed by a hydrophobic interaction chromatography (HIC) process as measured by an ELISA.

In some embodiments, the present disclosure provides a pharmaceutical composition comprising the purified EVs described herein and a pharmaceutically acceptable carrier. In some embodiments, the present disclosure provides a composition comprising EVs and protein impurities, wherein the protein impurities are lower than a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the present disclosure provides a composition comprising EVs and protein impurities, wherein the protein impurities are at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay.

In some embodiments, the protein impurities are at least about 5%, e.g., 5% to 10%, 5% to 20%, 5% to 25%, or 5% to 30%, lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 10%, e.g., 10% to 15%, 10% to 20%, 10% to 25%, 10% to 30%, 10% to 35%, 10% to 30%, 10% to 95%, 20% to 90%, 50% to 90%, or 80% to 90% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 11% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 12% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 13% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 14% lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay. In some embodiments, the protein impurities are at least about 15%, e.g., 15% to 20%, 15% to 25%, 15% to 30%, 15% to 35%, 15% to 40%, 20% to 25%, 20% to 30%, 20% to 35%, or 20% to 40%, lower in the purified EV composition compared to a reference EV composition purified by an AEX process, an AEX process followed by a hydrophobic interaction chromatography (HIC) process, or a density gradient ultracentrifugation process ("Opti"), wherein the protein impurities are measured by a bicinchoninic acid (BCA) assay.

In some embodiments, the present disclosure provides a composition comprising EVs and protein, e.g., perlecan, impurities, wherein the perlecan protein level is lower than a reference EV composition purified by an AEX process or an AEX process followed by a hydrophobic interaction chromatography (HIC) process, wherein the protein impurities are measured by an AlphaLisa assay. In some embodiments, the present disclosure provides a composition comprising EVs and perlecan protein, wherein the perlecan protein level is at least about 5%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, or at least about 40% lower in the purified EV composition compared to a reference EV composition purified by an AEX process or an AEX process followed by a hydrophobic interaction chromatography (HIC) process, wherein the protein impurities are measured by an AlphaLisa assay.

In some embodiments, the perlecan protein level is at least about 5%, e.g., 5% to 10%, 5% to 20%, 5% to 25%, or 5% to 30%, lower in the purified EV composition compared to a reference EV composition purified by an AEX process or an AEX process followed by a hydrophobic interaction chromatography (HIC) process, wherein the perlecan protein level is measured by an AlphaLisa assay. In some embodiments, the perlecan protein level is at least about 10%, e.g., 10% to 15%, 10% to 20%, 10% to 25%, 10% to 30%, 10% to 35%, or 10% to 30% lower in the purified EV composition compared to a reference EV composition purified by an AEX process or an AEX process followed by a hydrophobic interaction chromatography (HIC) process, or a density gradient ultracentrifugation process ("Opti"), wherein the perlecan protein level is measured by an AlphaLisa assay. In some embodiments, the perlecan protein level is at least about 11% lower in the purified EV composition compared to a reference EV composition purified by an AEX process or an AEX process followed by a hydrophobic interaction chromatography (HIC) process, wherein the perlecan protein level is measured by an AlphaLisa assay. In some embodiments, the perlecan protein level is at least about 12% lower in the purified EV composition compared to a reference EV composition purified by an AEX process or an AEX process followed by a hydrophobic interaction chromatography (HIC) process, wherein the perlecan protein level is measured by an AlphaLisa assay. In some embodiments, the perlecan protein level is at least about 13% lower in the purified EV composition compared to a reference EV composition purified by an AEX process or an AEX process followed by a hydrophobic interaction chromatography (HIC) process, wherein the perlecan protein level is measured by an AlphaLisa assay. In some embodiments, the perlecan protein level is at least about 14% lower in the purified EV composition compared to a reference EV composition purified by an AEX process or an AEX process followed by a hydrophobic interaction chromatography (HIC) process, wherein the perlecan protein level is measured by an AlphaLisa assay. In some embodiments, the perlecan protein level is at least about 15%, e.g., 15% to 20%, 15% to 25%, 15% to 30%, 15% to 35%, 15% to 40%, 20% to 25%, 20% to 30%, 20% to 35%, or 20% to 40%, lower in the purified EV composition compared to a reference EV composition purified by an AEX process or an AEX process followed by a hydrophobic interaction chromatography (HIC) process, wherein the perlecan protein level is measured by an AlphaLisa assay.

In some embodiments, the agrin protein level is at least about 5%, e.g., 5% to 10%, 5% to 20%, 5% to 25%, or 5% to 30%, lower in the purified EV composition compared to a reference EV composition purified by an AEX process or an AEX process followed by a hydrophobic interaction chromatography (HIC) process, wherein the agrin protein level is measured by an ELISA assay. In some embodiments, the agrin protein level is at least about 10%, e.g., 10% to 15%, 10% to 20%, 10% to 25%, 10% to 30%, 10% to 35%, or 10% to 30% lower in the purified EV composition compared to a reference EV composition purified by an AEX process or an AEX process followed by a hydrophobic interaction chromatography (HIC) process, or a density gradient ultracentrifugation process ("Opti"), wherein the agrin protein level is measured by an ELISA assay. In some embodiments, the agrin protein level is at least about 11% lower in the purified EV composition compared to a reference EV composition purified by an AEX process or an AEX process followed by a hydrophobic interaction chromatography (HIC) process, wherein the agrin protein level is measured by an ELISA assay. In some embodiments, the agrin protein level is at least about 12% lower in the purified EV composition compared to a reference EV composition purified by an AEX process or an AEX process followed by a hydrophobic interaction chromatography (HIC) process, wherein the agrin protein level is measured by an ELISA assay. In some embodiments, the agrin protein level is at least about 13% lower in the purified EV composition compared to a reference EV composition purified by an AEX process or an AEX process followed by a hydrophobic interaction chromatography (HIC) process, wherein the agrin protein level is measured by an ELISA assay. In some embodiments, the agrin protein level is at least about 14% lower in the purified EV composition compared to a reference EV composition purified by an AEX process or an AEX process followed by a hydrophobic interaction chromatography (HIC) process, wherein the agrin protein level is measured by an ELISA assay. In some embodiments, the agrin protein level is at least about 15%, e.g., 15% to 20%, 15% to 25%, 15% to 30%, 15% to 35%, 15% to 40%, 20% to 25%, 20% to 30%, 20% to 35%, or 20% to 40%, lower in the purified EV composition compared to a reference EV composition purified by an AEX process or an AEX process followed by a hydrophobic interaction chromatography (HIC) process, wherein the agrin protein level is measured by an ELISA assay.

In some embodiments, compositions comprising the purified EVs have a higher potency than a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 5%, e.g., 5% to 10%, 5% to 15%, 5% to 20%, 5% to 25%, 5% to 30%, 5% to 35%, 5% to 40%, 5% to 45%, 5% to 50%, e.g., 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 10%, e.g., 10% to 15%, 10% to 20%, 10% to 25%, 10% to 30%, 10% to 35%, 10% to 40%, 10% to 45%, 10% to 50%, 10% to 55%, or 10% to 60%, e.g., 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, or 60%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 11% higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 15%, e.g., 15% to 20%, 15% to 25%, 15% to 30%, 15% to 35%, 15% to 40%, 15% to 45%, 15% to 50%, 15% to 55%, or 15% to 60%, e.g., 16%, 17%, 18%, 19%, 20%, 21%, 22%, 23%, 24%, 25%, 26%, 27%, 28%, 29%, 30%, 35%, 40%, 45%, 50%, 55%, or 60%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 20%, e.g., 20% to 25%, 20% to 30%, 20% to 35%, 20% to 40%, 20% to 45%, 20% to 50%, 20% to 55%, or 20% to 60%, e.g., 20%, 21%, 22%, 23%, 24%, 25%, 26%, 27%, 28%, 29%, 30%, 35%, 40%, 45%, 50%, 55%, or 60%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 25%, e.g., 25% to 30%, 25% to 35%, 25% to 40%, 25% to 45%, 25% to 50%, 25% to 55%, or 25% to 60%, e.g., 25%, 26%, 27%, 28%, 29%, 30%, 35%, 40%, 45%, 50%, 55%, 60%, 65%, 70%, 75%, or 80%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 30%, e.g., 30% to 35%, 30% to 40%, 30% to 45%, 30% to 50%, 30% to 55%, or 30% to 60%, e.g., 30%, 35%, 40%, 45%, 50%, 55%, 60%, 65%, 70%, 75%, 80%, 80%, 85%, or 90%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 35%, e.g., 35% to 40%, 35% to 45%, 35% to 50%, 35% to 55%, or 35% to 60%, e.g., 35%, 40%, 45%, 50%, 55%, 60%, 65%, 70%, 75%, 80%, 80%, 85%, or 90%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 40%, e.g., 40% to 45%, 40% to 50%, 40% to 55%, or 40% to 60%, e.g., 40%, 45%, 50%, 55%, 60%, 65%, 70%, 75%, 80%, 80%, 85%, or 90%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 45%, e.g., 45% to 50%, 45% to 55%, or 45% to 60%, e.g., 45%, 50%, 55%, 60%, 65%, 70%, 75%, 80%, 80%, 85%, or 90%, higher than that of a reference composition comprising EVs purified by an AEX process, an AEX process followed by a hydrophobic interaction chromatography (HIC) process, or a density gradient ultracentrifugation process ("Opti"). In some embodiments, the potency of the composition comprising the purified EVs is at least about 50% higher than that of a reference composition comprising EVs purified by an AEX process, an AEX process followed by a hydrophobic interaction chromatography (HIC) process, or a density gradient ultracentrifugation process ("Opti").

In some aspects, the purified EVs according to the present disclosure is at least 75% pure. In some aspects, the purified EVs according to the present disclosure is at least about 80% pure. In some aspects, the purified EVs according to the present disclosure is at least about 85% pure. In some aspects, the purified EVs according to the present disclosure is at least about 90% pure. In some aspects, the purified EVs according to the present disclosure is at least about 95% pure. In some aspects, the purified EVs according to the present disclosure is at least about 96% pure. In some aspects, the purified EVs according to the present disclosure is at least about 97% pure. In some aspects, the purified EVs according to the present disclosure is at least about 98% pure. In some aspects, the purified EVs according to the present disclosure is at least about 99% pure. In some aspects, the purified EVs according to the present disclosure is about 100% pure.

In some embodiments, the present disclosure provides a method of administering a composition comprising purified EVs to a subject in need thereof. In some embodiments, the present disclosure provides a method of treating a disease or condition in a subject in need thereof comprising administering to the subject a composition comprising purified EVs.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

EXAMPLES

The following examples are put forth so as to provide those of ordinary skill in the art with a complete disclosure and description of how to make and use the embodiments described herein, and are not intended to limit the scope of the appended claims, nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., s or sec, second(s); min, minute(s); h or hr, hour(s).

The embodiments described herein employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pa.: Mack Publishing Company, 2005); Carey and Sundberg Advanced Organic Chemistry 3rd Ed. (Plenum Press) Vols A and B (1992).

Example 1: Multistep Chromatographic Methods for Preparing EVs

Example 1-1: Pretreatment of Samples Comprising EVs

HEK293 cells grown in a bioreactor were harvested and clarified with depth filtration media. The samples were then treated with Benzonase® (MilliporeSigma) endonuclease to digest nucleic acids. Samples were incubated with Benzonase® and 1 mM or 2 mM $MgCl_2$ for more than 10 hours. The samples can optionally be incubated for longer to allow for additional nuclease digestion, for of a period of about 2-5 days at 15° C. to about 25° C. The nuclease treated pool was concentrated approximately 10× with a tangential flow filtration (TFF) with a 1000 kDa MWCO Biomax membrane (MilliporeSigma) and diafiltered into 37 mM MES acid, 20 mM NaOH, 137 mM NaCl, pH 6.2.

Example 1-2: Cation Exchange Chromatography (CEX)

The samples obtained from the tangential flow filtration (TFF) were purified with a CEX chromatography in a weak partitioning mode, where EVs are bound more weakly than impurities. Desired products were recovered from high load challenges and a post-load flush. Specifically, a CEX column containing POROS XS50 was equilibrated with a buffer containing 175 mM Na+, 37 mM MES, pH 6.1. The column was then challenged with the product obtained from TFF, at the rate of $3.4 \times 10^{12}$ particles per mL of CEX resin in the loading buffer of a similar pH and conductivity to the equilibration buffer. The flow-through during loading and subsequent application of two column volumes (CV) of equilibration buffer was collected ("CEX pool"). The column was subsequently stripped with 2 M NaCl, 50 mM Tris, pH 7.4 and sanitized with 1 M NaOH, before being stored in 20% ethanol, 150 mM NaCl, 50 mM Tris, pH 7.4. As shown in Table 4, the amount of impurities found in the flowthrough was significantly reduced compared to the amount found in the load prior to CEX. Overall particle yield (NTA) from the process was 76%.

TABLE 4

| Protein Impurity | Load (µg/1 × $10^{11}$ particles) | Flowthrough (µg/1 × $10^{11}$ particles) |
|---|---|---|
| BCA | 207 | 119 |
| Agrin | 84 | 28 |
| Perlecan | 120 | 19 |

Example 1-3: Anion Exchange Chromatography (AEX)

The CEX pool was purified with an AEX chromatography unit operation in bind-elute mode. For loading, the CEX pool was titrated to pH 7.4 with 1 M Tris, pH 8.0 and the anion concentration was raised to 550 mM Cl— by adding 5 M NaCl. An AEX device containing SARTOBIND® Q membranes (8 mm bed depth) was equilibrated with 550 mM NaCl, 50 mM Tris, pH 7.4. The column was then challenged with $3.2 \times 10^{12}$ particles of CEX pool per mL of AEX resin with the loading buffer containing a similar pH and conductivity to the equilibration buffer.

Following loading, ten CVs of equilibration buffer were passed over the column prior to elution. Elution buffer consisting of 1200 mM NaCl, 50 mM Tris, pH 7.4 was applied to the column with approximately 5 CVs of column effluent comprising the AEX elution pool ("AEX pool"). The column was subsequently stripped with 2 M NaCl, 50 mM Tris, pH 7.4 and sanitized with 1 M NaOH, before being stored in 20% ethanol, 150 mM NaCl, 50 mM Tris, pH 7.4.

The AEX step decreased the amount of protein (BCA) impurities from 119 $\mu g/1 \times 10^{11}$ particles in the load to 53 $\mu g/1 \times 10^{11}$ particles in the elution pool. No significant clearance of agrin or perlecan was observed. Particle yield (NTA) across this step, a measure of product recovery, was 37%.

Example 1-4: Depth Filtration

The AEX pool was diluted to $1 \times 10^{11}$ particles/mL in 1200 mM NaCl, 50 mM Tris, pH 7.4 to ensure an adequate volumetric challenge for the subsequent depth filtration step. A V100P adsorptive depth filter (Pall) was first equilibrated with 100 L/m$^2$ of reverse-osmosis purified and deionized water (RODI), followed by 100 L/m$^2$ of 1200 mM NaCl, 50 mM Tris, pH 7.4. The diluted AEX pool was then processed through the filter at a challenge of 46 L/m$^2$ with a flux of 150 L/m$^2$/h ("Depth filtered AEX pool"). Product yield was maximized by the inclusion of a post-load flush of equilibration buffer. No significant reduction of protein was noted and particle yield (NTA) across this step, a measure of product recovery, was 68%.

Example 1-5: Mixed Mode Chromatography (MMC)

The depth filtered AEX pool was purified with mixed mode chromatography unit operated in flowthrough mode. Hypercel CMM (Pall), a resin with functional groups supporting CEX and hydrophobic interactions (mixed mode, "MMC"), was packed into a column. The column can also be optionally linked in series with another column, such as CaptoCore700, a MMC column. The column was equilibrated with 1 M NaCl, 50 mM Tris, pH 7.4. The column was then challenged with $1.5 \times 10^{12}$ particles of depth filtered AEX pool per mL of MMC resin with the buffer matrix containing a similar pH and conductivity to the equilibration buffer. The flowthrough during the load and a subsequent five CVs of equilibration buffer were collected as the MMC product pool ("MMC pool"). The column was subsequently equilibrated with 1 M NaCl, 50 mM Tris, pH 7.4 and sanitized with 1 M NaOH, before being stored in 20% ethanol, 150 mM NaCl, 50 mM Tris, pH 7.4. As shown in Table 5, the amount of protein impurity found in the flowthrough after purification was reduced compared the amount contained in the load prior to chromatography. Particle yield (NTA) across this step, a measure of product recovery, was 77%.

TABLE 5

| Protein Impurity | Load ($\mu g/1 \times 10^{11}$ particles) | Flowthrough ($\mu g/1 \times 10^{11}$ particles) |
| --- | --- | --- |
| BCA | 52 | 42 |
| Agrin | 43 | 24 |
| Perlecan | 29 | 19 |

Example 1-6: Ultrafiltration/Diafiltration

The MMC pool was then concentrated approximately 10× with a tangential flow filtration (TFF) with a 750 kDa MWCO mPES MicroKros hollow fiber membrane and diafiltered into 5 diavolumes of 0.003 M sodium phosphate dibasic, 0.001 M potassium phosphate monobasic, 154 mM sodium chloride, 5% (w/v) sucrose, pH 7.4. In addition to concentration and diafiltration, this TFF step decreased the amount of two protein impurities as summarized below in Table 6. There was not a significant change in normalized BCA concentration. Particle yield (NTA) across this step, a measure of product recovery, was 77%.

TABLE 6

| Protein Impurity | Load ($\mu g/1 \times 10^{11}$ particles) | Pool ($\mu g/1 \times 10^{11}$ particles) |
| --- | --- | --- |
| Agrin | 24 | 4 |
| Perlecan | 19 | 2 |

Throughout Examples 1-1 through 1-6, 0.22 um or 0.45 µm membrane filtration was employed to reduce bioburden and endotoxin. Membrane filtration steps were included before Benzonase, first TFF, CEX, AEX, MMC, and TFF2 as well as after the second TFF.

The overall particle yield (NTA) from clarified harvest to DSI was 4%.

Example 1-7: Density Gradient Ultracentrifugation (OPTIPREP®)

Cell culture supernatant containing exosomes was collected from high density suspension cultures of HEK293 SF cells after 7-9 days. Cell culture supernatant was serially centrifuged, with the supernatant of the previous spin serving as the input for the subsequent spin: cell culture supernatant was centrifuged at 5,000×g for 30 minutes, the supernatant collected and the pellet discarded; the supernatant was then centrifuged at 16,000×g for 30 minutes and the supernatant collected and the pellet discarded; the supernatant was then centrifuged at 133,900×g for 3 hours, and the resulting supernatant discarded and the pellet collected and resuspended in 1 mL of PBS. The resuspended 133,900×g pellet was further purified by running in an OPTIPREP™ Iodixanol gradient: a 4-tier sterile gradient was prepared by mixing 3 mL of OPTIPREP™ (60% Iodixanol) with 1 mL of resuspended pellet to generate 4 mL of 45% Iodixanol, then overlaid serially with 3 mL 30% Iodixanol, 2 mL 22.5% Iodixanol, 2 mL 17.5% Iodixanol, and 1 mL PBS in a 12 mL Ultra-Clear (344059) tube for a SW 41 Ti rotor. The gradient was ultracentrifuged at 150,000×g for 16 hours at 4° C. Ultracentrifugation resulted in a Top Fraction known to contain exosomes, a Middle Fraction containing cell debris of moderate density, and a Bottom Fraction containing high density aggregates and cellular debris. The exosome layer was gently collected from the top ~2 mL of the tube, diluted in ~32 mL PBS in a 38.5 mL Ultra-Clear (344058) tube and centrifuged at 10,000×g for 30 minutes, the supernatant collected and ultracentrifuged at 133,900×g for 3 hours at 4° C. to pellet the purified exosomes. The pelleted exosomes were then resuspended in a minimal volume of PBS (~200 µL) and stored at 4° C. Final purified concentration of exosomes was determined using nanoparticle tracking analysis (NTA).

Figure 4:
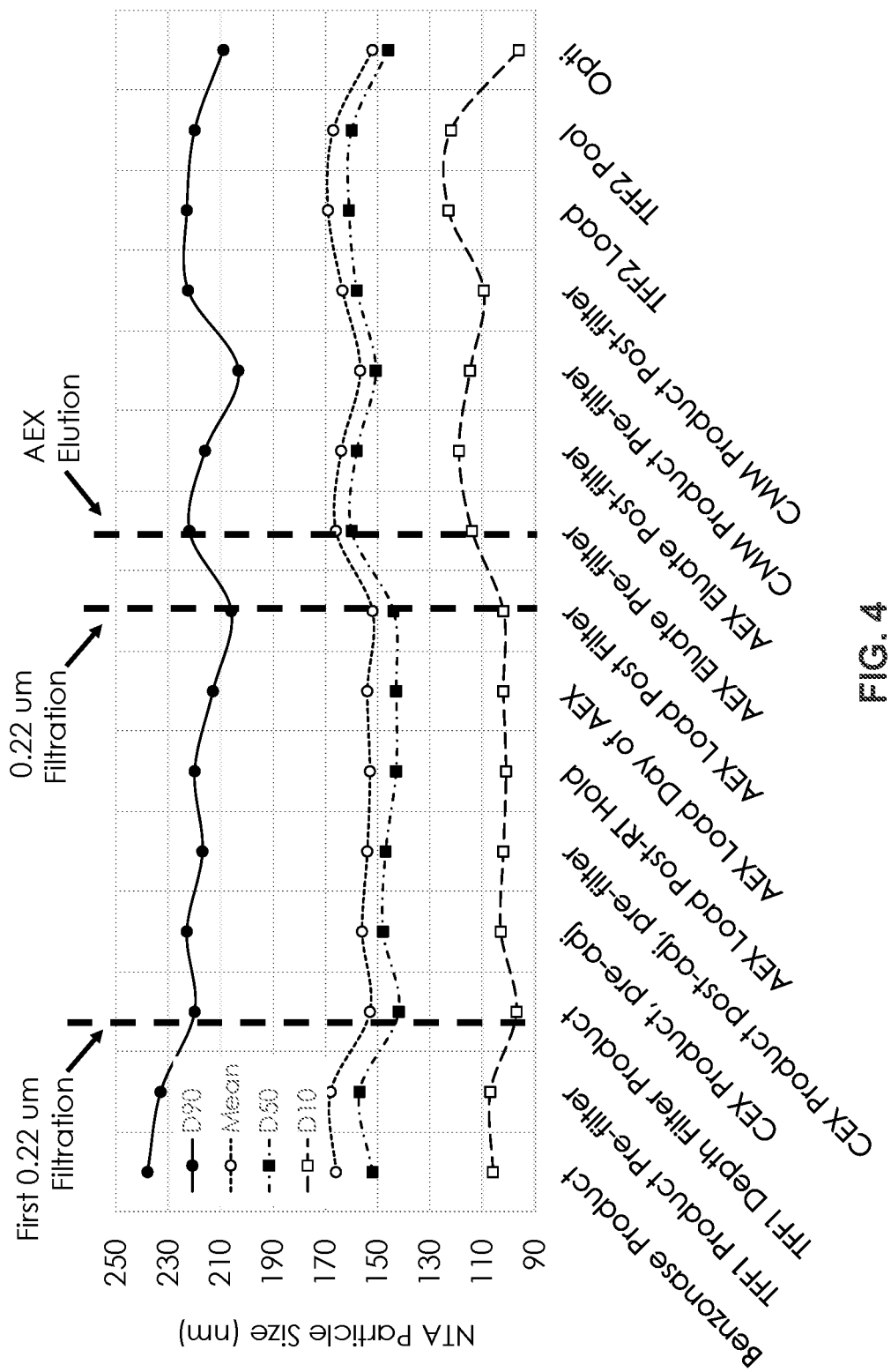
FIG. 4 shows particle characteristics throughout the purification process measured with NTA. D10, D50, and D90 are the diameters at which 10%, 50%, and 90%, respectively, of a sample's mass is comprised of smaller particles.

Example 1-8: Characterization of EVs Prepared by Multistep Chromatographic Method EVs prepared by the multistep chromatographic method had compositions similar to EVs prepared using density gradient medium, OPTIPREP" (Stemcell Technologies, Inc.). FIG. 3 shows particle yields across the EV production process. The figure shows that the process development using multistep chromatographic methods improved product yield across batches. FIG. 4 also shows particle characteristics throughout the purification process measured with nanoparticle tracking analysis (NTA).

Figure 6A:
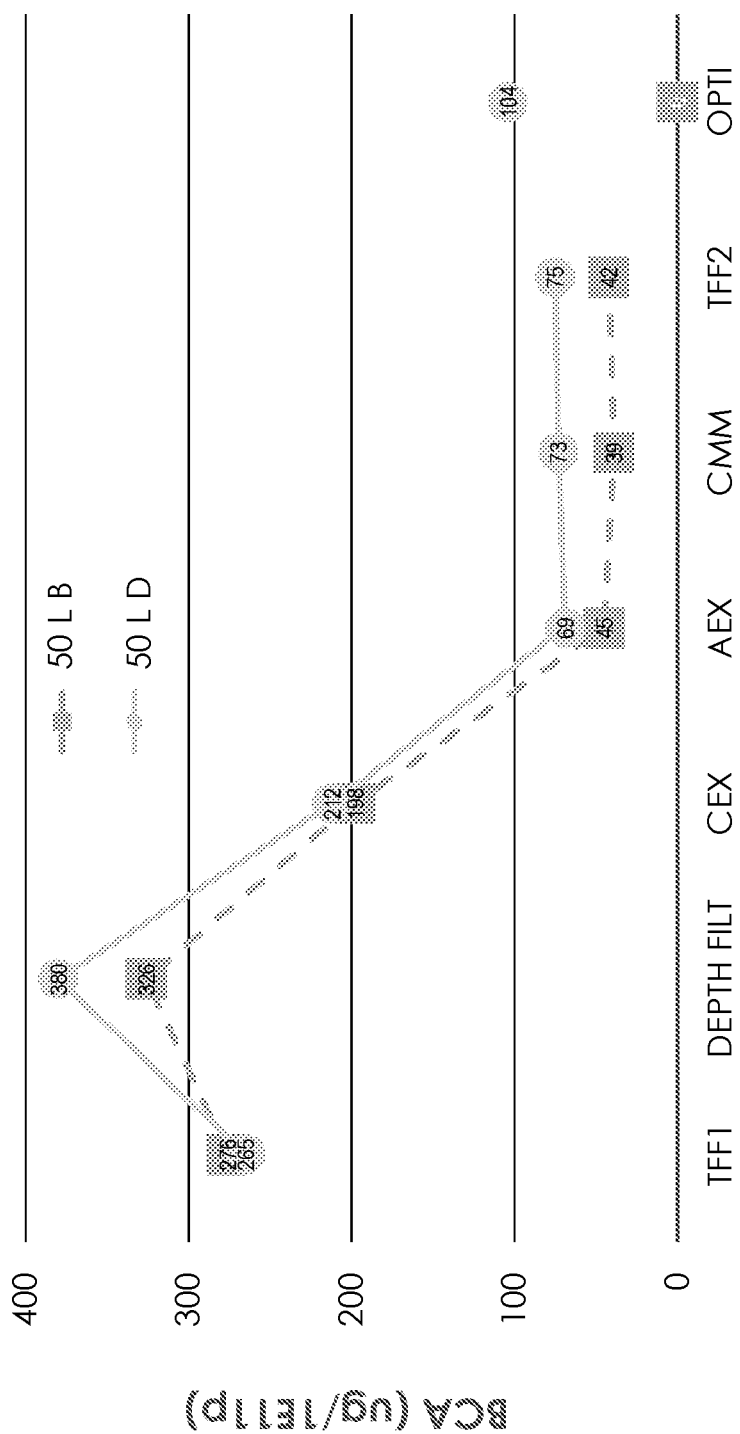
FIG. 6A shows the level of impurities measured by a BCA assay throughout the purification process in comparison to a density gradient ultracentrifugation process ("Opti").
Figure 6B:
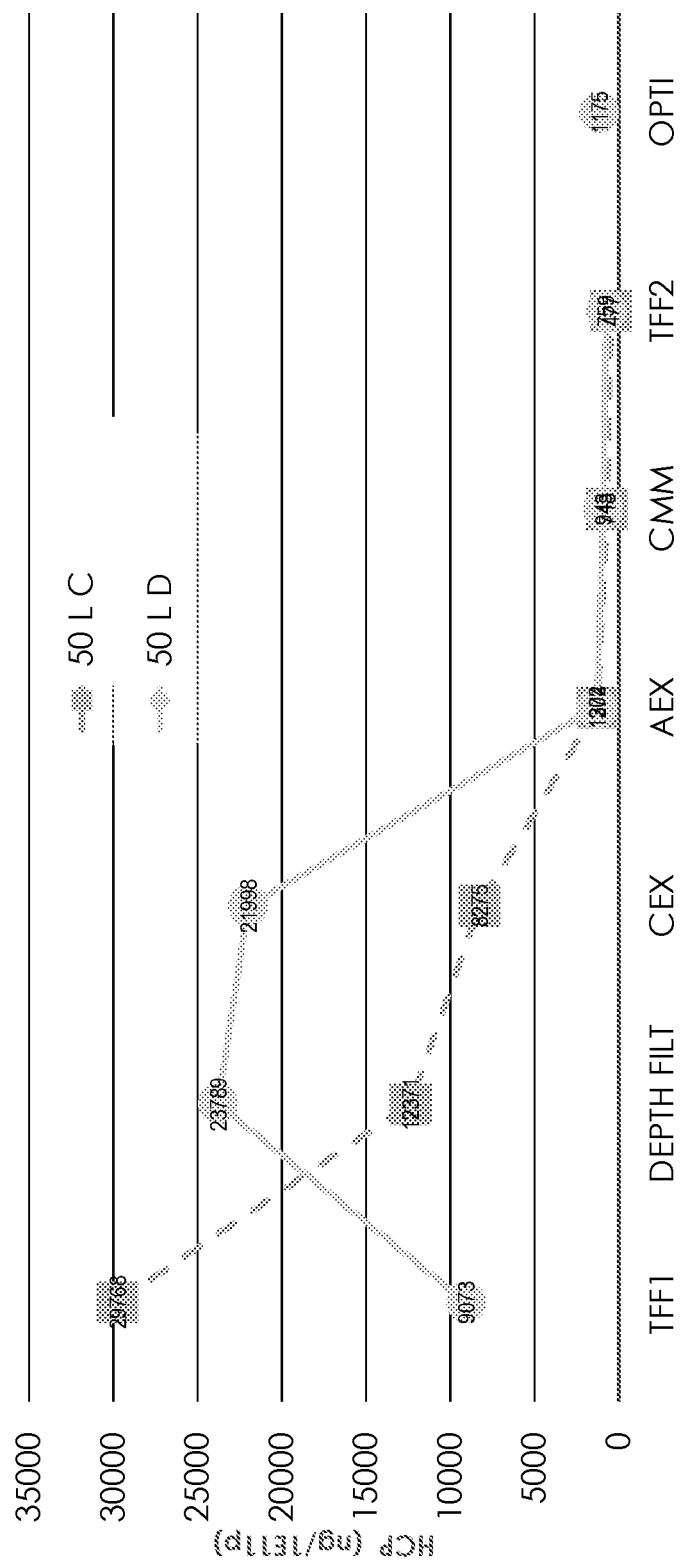
FIG. 6B shows the level of host cell protein (HCP) impurities throughout the purification process, e.g., CEX-AEX-CMM, in comparison to a density gradient ultracentrifugation process ("Opti"), as measured by an ELISA.
Figure 6C:
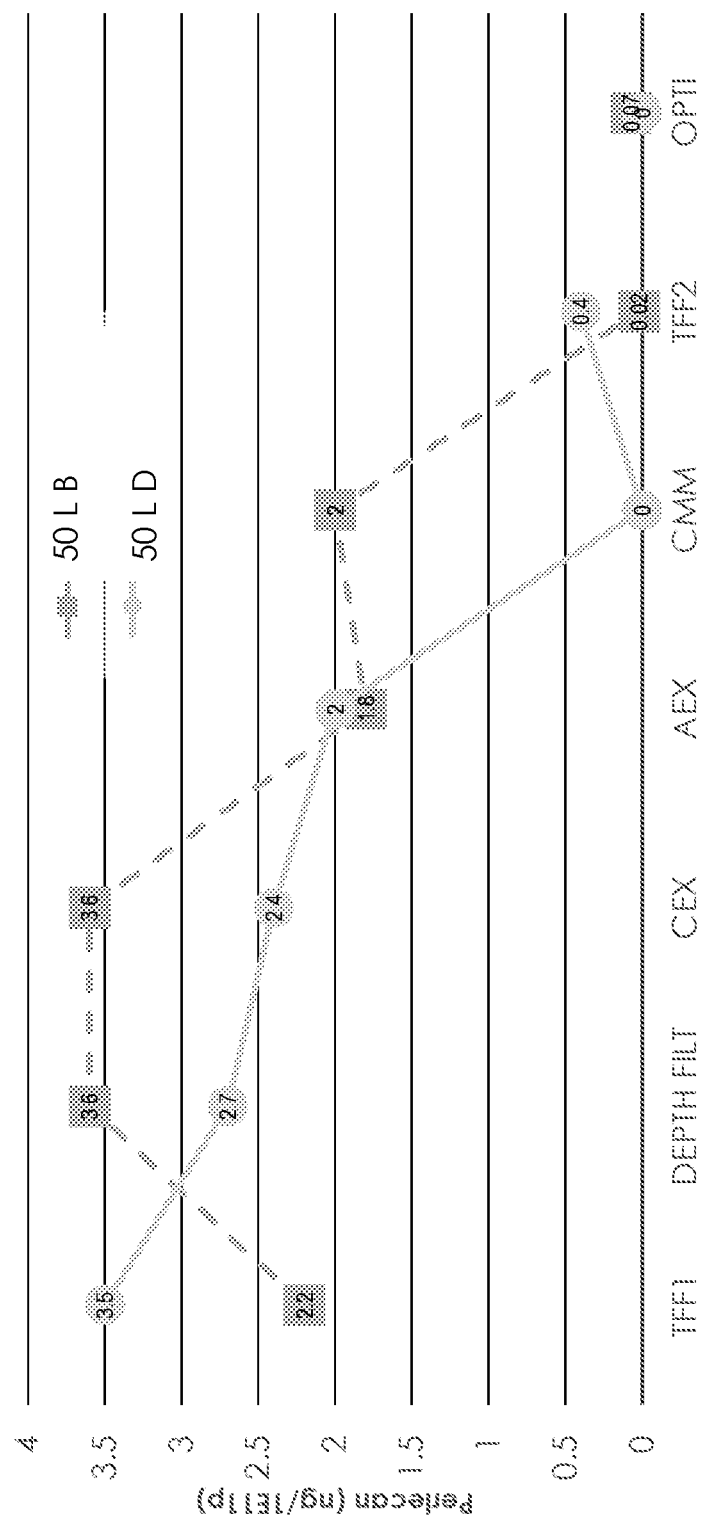
FIG. 6C shows the level of an impurity protein, perlecan throughout the purification step, e.g., CEX-AEX-CMM in comparison to a density gradient ultracentrifugation process ("Opti"), as measured by an AlphaLISA assay.
Figure 6D:
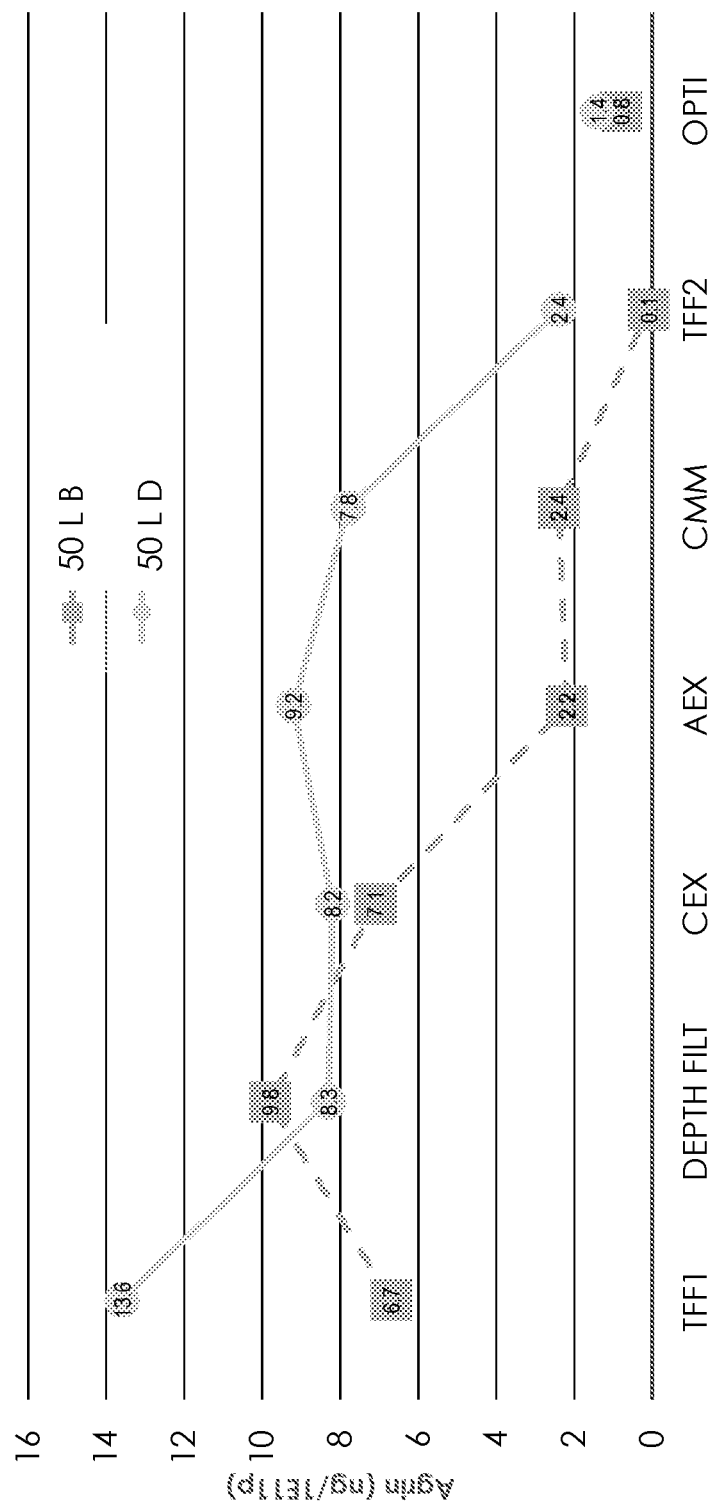
FIG. 6D shows the level of an impurity protein, agrin throughout the purification step, e.g., CEX-AEX-CMM, in comparison to a density gradient ultracentrifugation process ("Opti"), as measured by an ELISA assay.

Proteomics analysis of EVs purified by the multistep chromatographic methods indicated that their composition was similar to Opti-purified material albeit with more agrin and fewer histones, as summarized in Table 7 and FIGS. 6A-D and 7A-B. Specifically, FIG. 6A shows the total protein impurities measured by a BCA assay. FIG. 6A shows that the amount of total protein impurities drops significantly when the CEX and the AEX processes are combined. Similarly, FIG. 6B shows that the combination of the CEX and AEX (and MMC) significantly reduces host cell proteins (HCP). FIG. 6C shows that the multistep chromatographic method of the present disclosure significantly reduces the Perlecan protein level at MMC or at TFF2. FIG. 6D shows that the Agrin level is reduced significantly at the AEX, MMC, and TFF2.

TABLE 7

| Protein Impurity | Multistep chromatographic method purified EVs (μg/1 × $10^{11}$ particles) | Opti-purified EVs (μg/1 × $10^{11}$ particles) |
|---|---|---|
| BCA | 48 | 75 |
| Agrin | 4 | 1 |
| Perlecan | 2 | 0 |

Figure 7B:
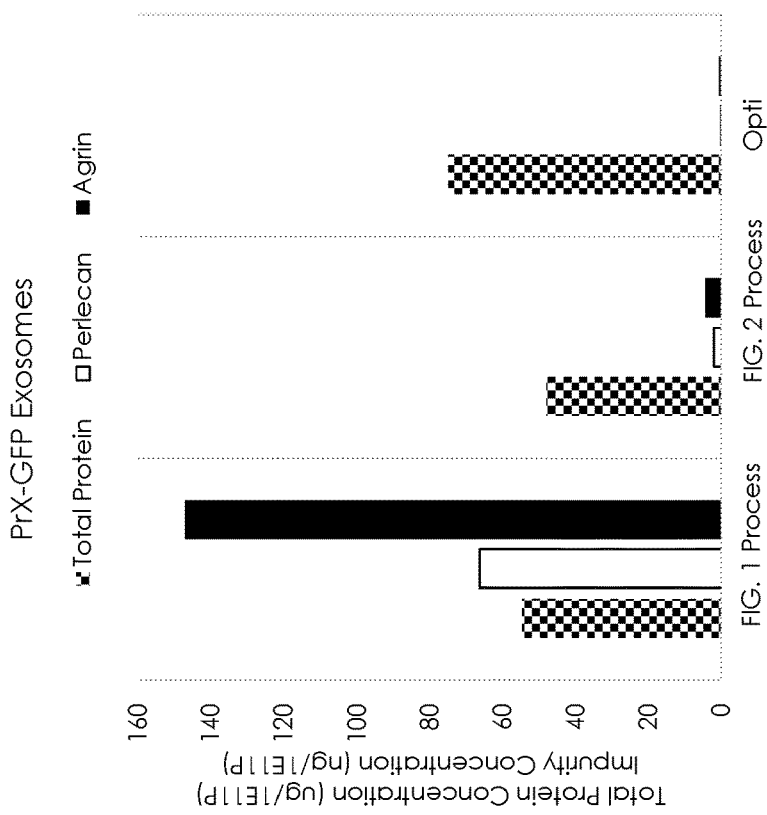
FIG. 7B shows the total protein impurities, Perlecan protein, and Agrin protein level of the purification process (middle) of EVs with Scaffold X fused to GFP compared to a purification process of an AEX process followed by an HIC process (FIG. 1) and a density gradient ultracentrifugation process ("Opti"). The total protein impurities were measured by a BCA assay, the Perlecan protein level is measured by an AlphaLisa, and the Agrin level is measured by an ELISA.
Figure 7A:
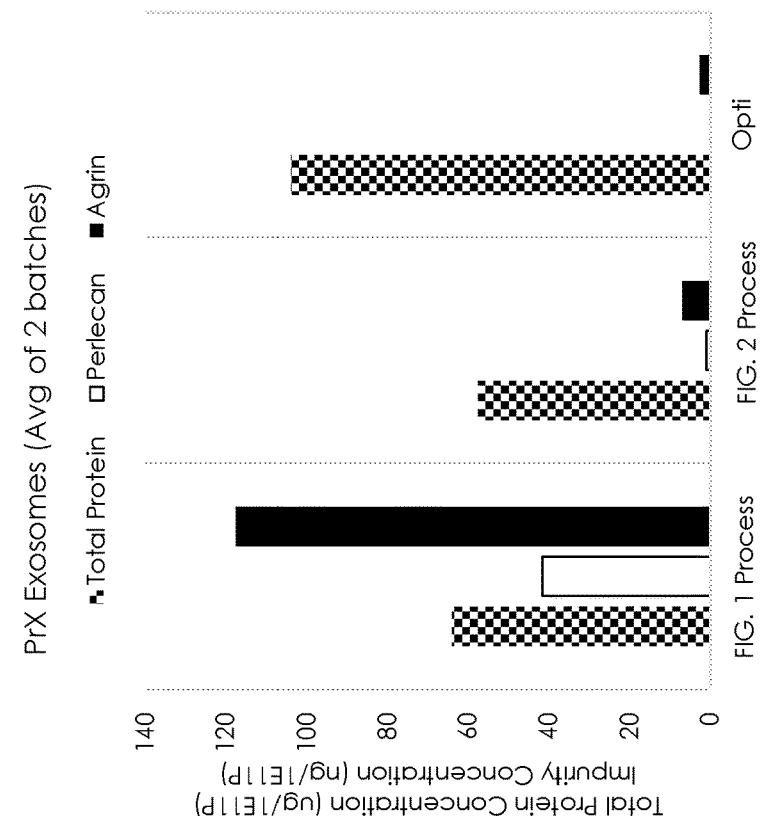
FIG. 7A shows the total protein impurities, perlecan protein, and agrin protein levels in the purification process (middle) of exemplary Scaffold X EVs compared to a purification process of an AEX process followed by an HIC process (FIG. 1) and a density gradient ultracentrifugation process ("Opti").
Figure 8:
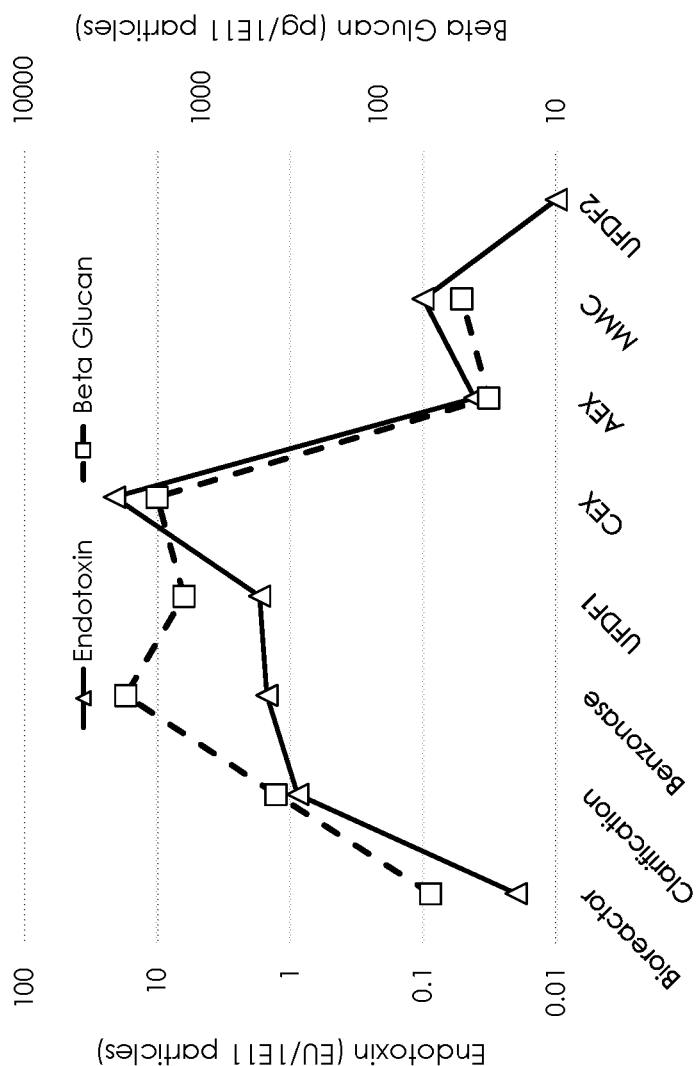
FIG. 8 shows endotoxin and beta glucan clearance across the described EV production processes. The clearance level was quantified using ENDOSAFE® PTS™. Hollow data points denote values below the limit of quantification. Levels of endotoxin and beta glucan increase during the clarification and Benzonase steps due to impurities leaching from the depth filters and as well the background environmental bioburden that can be present during purification operations.

FIG. 7A shows the amounts of perlecan, agrin, and BCA in the sample pool obtained in the purification process (middle) of EVs with Scaffold X compared to a purification process of an AEX process followed by an HIC process (FIG. 1) and a density gradient ultracentrifugation process ("Opti") as described in Example 1-7. FIG. 7B shows the total protein impurities, Perlecan protein, and Agrin protein level of the purification process (middle) of EVs with Scaffold X fused to GFP compared to a purification process of an AEX process followed by an HIC process (FIG. 1) and a density gradient ultracentrifugation process ("Opti") as described in Example 1-7. The total protein impurities were measured by a BCA assay, the Perlecan protein level is measured by an AlphaLisa, and the Agrin level is measured by an ELISA. The multi chromatographic process clearly has fewer total protein impurities than the sample purified by Opti purified EVs or the sample purified by the FIG. 1 process. In addition, the EVs prepared by the present methods show a lower amount of BCA protein compared to the Opti-purification process.

Figure 2:
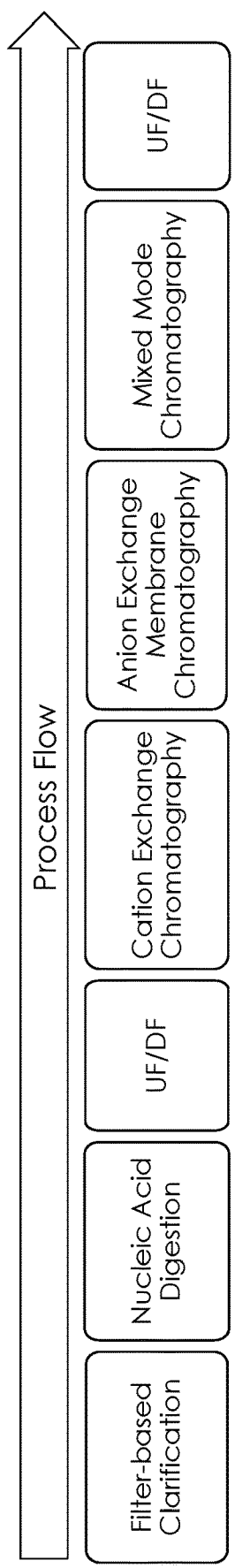
FIG. 2 shows a schematic of a large-scale purification process of extracellular vesicles (EVs) comprising a cation exchange chromatography (CEX) process followed by an anion exchange chromatography (AEX) and mixed mode chromatography process.
Figure 9B:
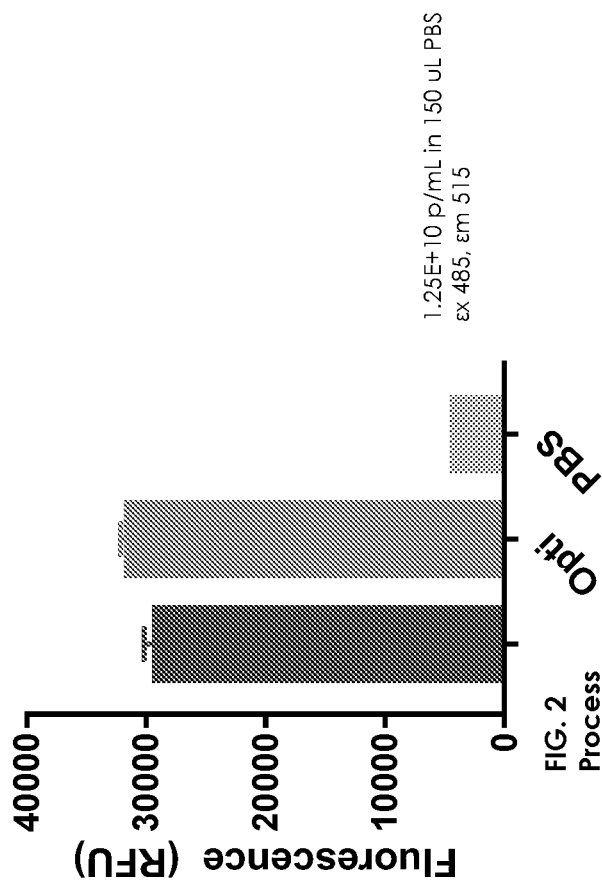
FIG. 9B shows Green Fluorescent Protein ("GFP") quantification of the described EV production process and a density gradient ultracentrifugation process ("Opti").
Figure 9A:
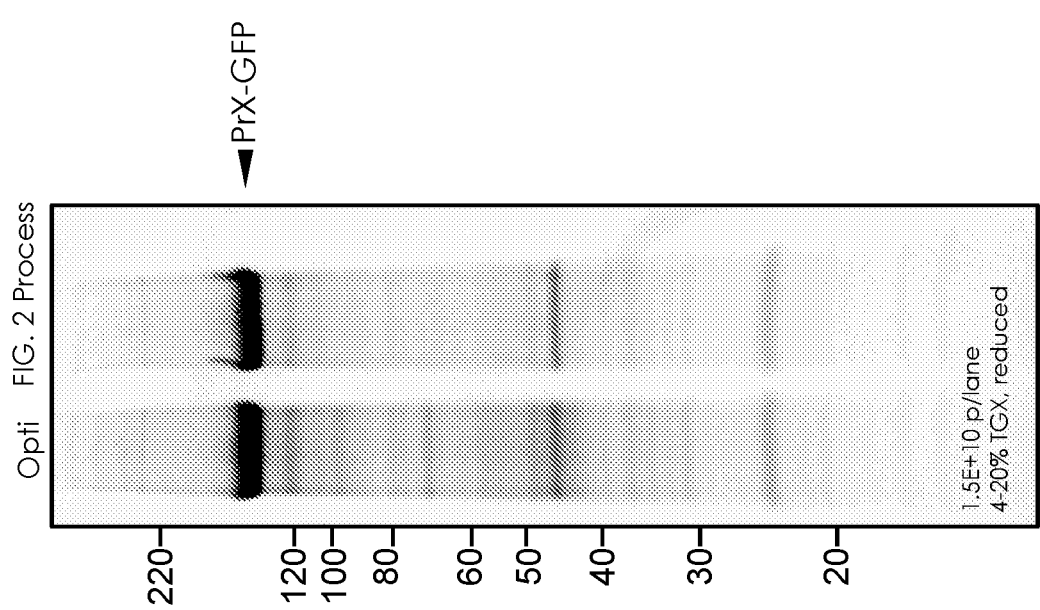
FIG. 9A is a polyacramide gel showing total protein fingerprint similarities between the described EV production process and a density gradient ultracentrifugation process ("Opti").
Figure 10A:
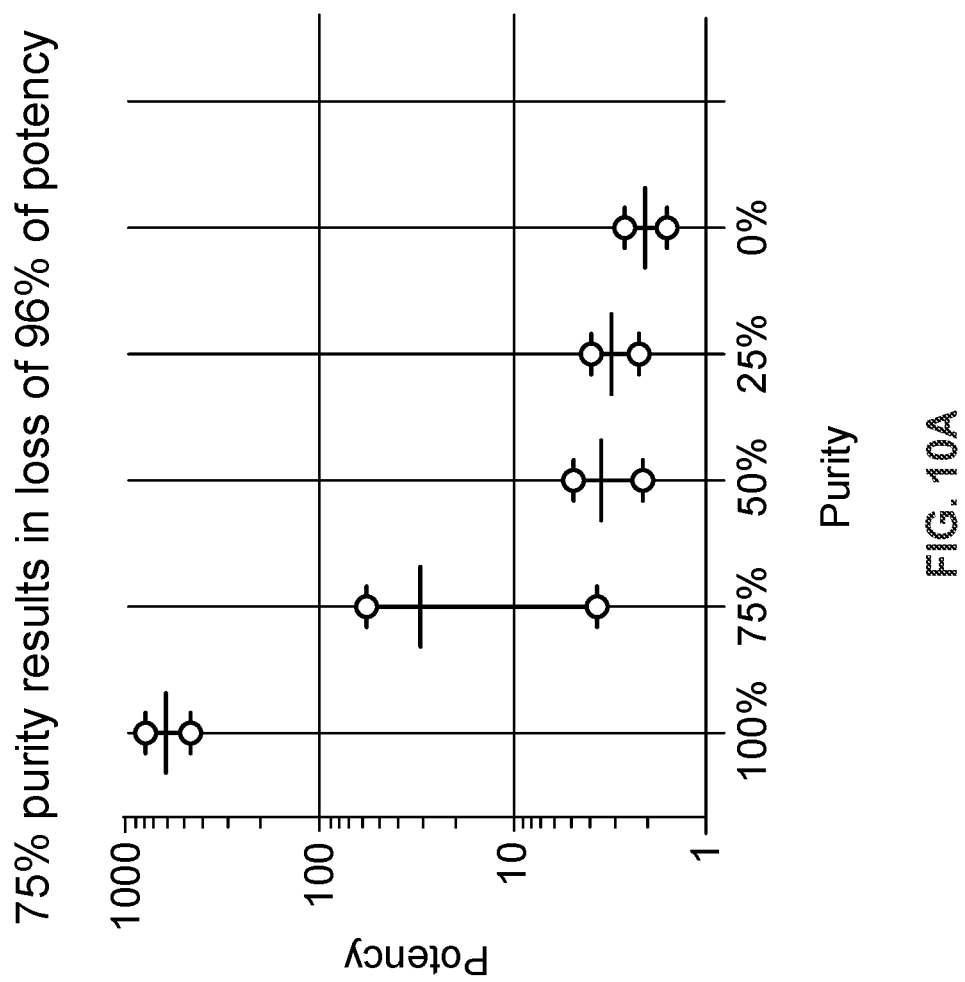
FIG. 10A shows the correlation between EV purity and potency.
Figure 10B:
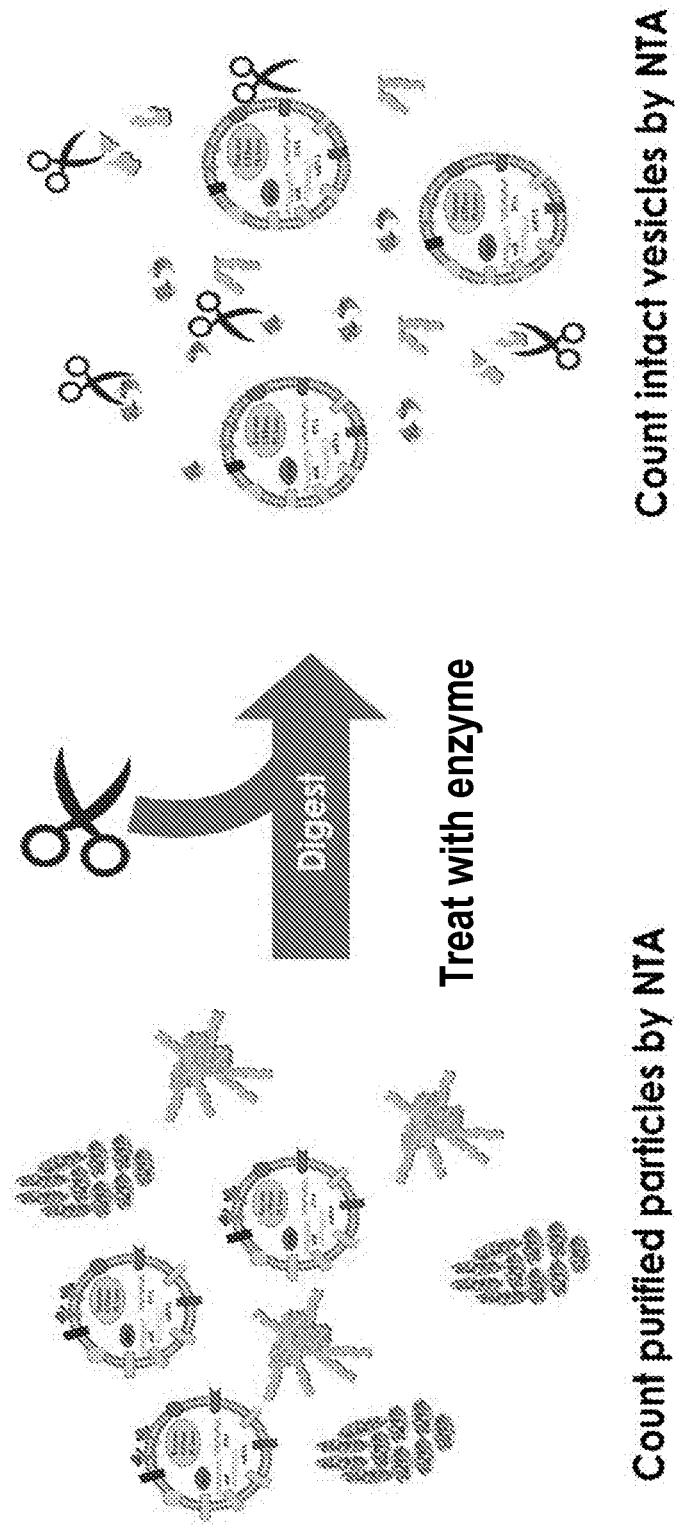
FIG. 10B shows an analytical method to uncover particulate impurities in EV. Identifying true impurity burden allows removal of the impurities and can result in an ultra pure product. Non-vesicular particles (e.g., protein aggregates) are impurities that need to be removed.
Figure 11A:
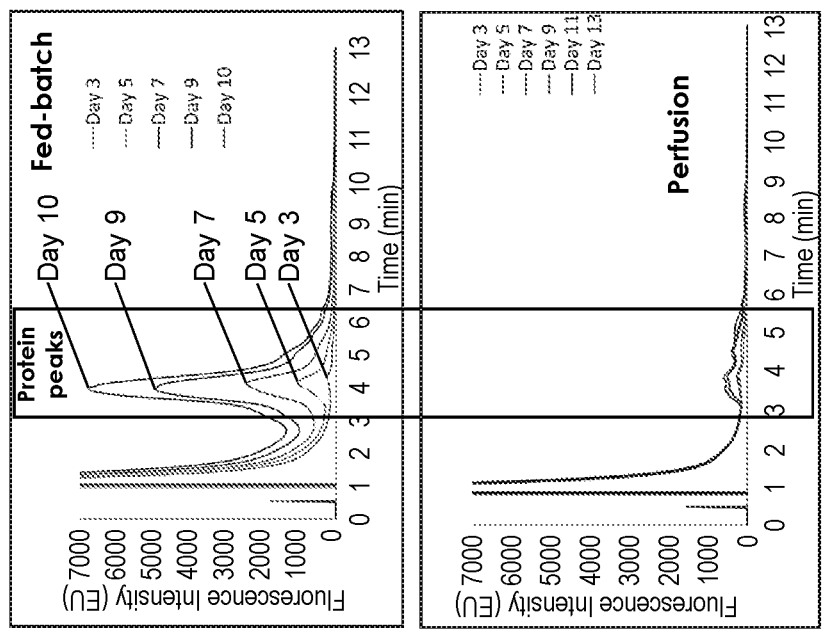
FIG. 11A shows a small-scale production of EV viability and protein impurities peaks in fluorescence intensity (EU).
Figure 11B:
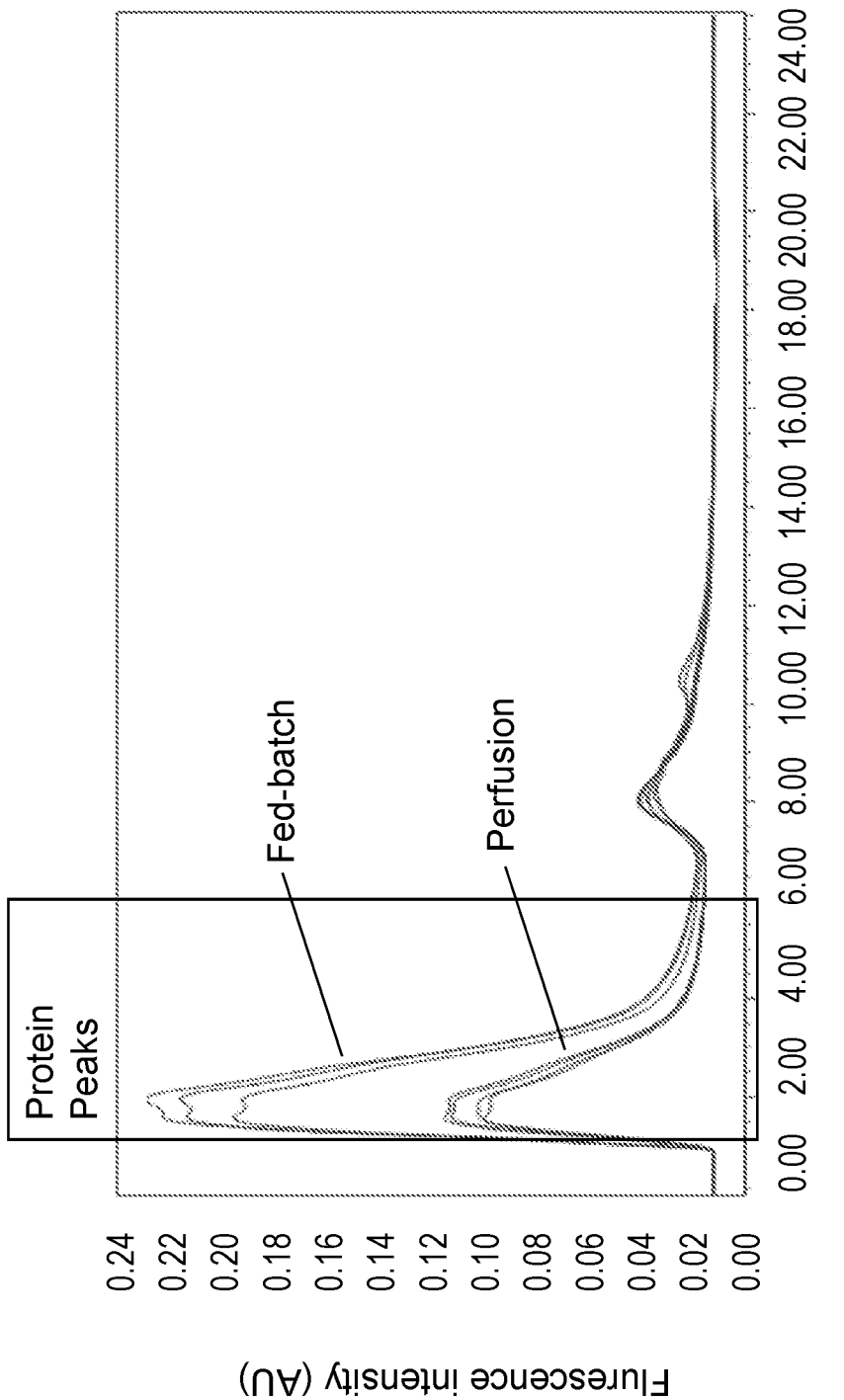
FIG. 11B shows comparison of the 50 L fed-batch and 10 L perfusion cell culture runs and the protein elution gradients.

FIG. 9A shows a polyacramide gel showing total protein fingerprint similarities between the described EV production process of FIG. 2 and a density gradient ultracentrifugation process ("Opti") described in Example 1-7. The total protein fingerprint of the FIG. 2 process is comparable to that of the Opti process. FIG. 9B shows Green Fluorescent Protein ("GFP") quantification of the described EV production process of FIG. 2 and an Opti process described in Example 1-7. The amount of exosomes obtained from the FIG. 2 process is comparable to that of the Opti process.

Example 2: Methods of Sterile Filtering Exosomes

Sterile filtration of exosomes is performed by applying positive pressure with a peristaltic pump. Silicone tubing is connected to the inlet and outlet of a filter with an absolute pore size of 0.22 μm. The tubing at the inlet of the filter is placed in the feed bottle or connected to the feed bag while the tubing at the outlet end of the filter is either placed in a bottle or connected to a bag to collect the filtrate. The tubing between the feed vessel and the filter inlet is positioned in the head of a peristaltic pump to generate the positive pressure and drive flow through the filter. Filtration is performed at temperatures ranging from 15 to 25° C. with feeds ranging from 1-5 cP in viscosity.

This method of sterile filtration can be applied to all purification process intermediates, drug substance intermediates, and drug products for different exosome constructs. Pre-treatment for filter feeds may include centrifugation, depth filtration, normal flow filtration, tangential flow filtration, nuclease treatment, ion exchange chromatography, hydrophobic interaction chromatography, and mixed mode chromatography. Parameters such as flux, volumetric load challenge, and load concentration may vary based on exosome construct and process intermediate. The differences in these parameters are outlined in Table 8.

TABLE 8

| Exosome Type | Process Step | Flux Range (LMH) | Load Challenge Range (L/m2) | Load Concentration Range (p/mL) |
|---|---|---|---|---|
| Native | Clarified Harvest | TBD | TBD | 5E9-5E11 |
|  | Post-Harvest Intermediates | 300-3500 | 50-200 | 5E9-5E13 |
| Protein X | Clarified Harvest | 100-150 | 40-80 | 1E10-1E12 |
|  | Post-Harvest Intermediates | 300-500 | 100-300 | 1E10-5E13 |
| IL12 | Clarified Harvest | 50-100 | 50-150 | 1E9-1E11 |
|  | Post-Harvest Intermediates | 300-500 | 50-250 | 1E9-5E13 |

Example 3: Bioreactor Production

Figure 12A:
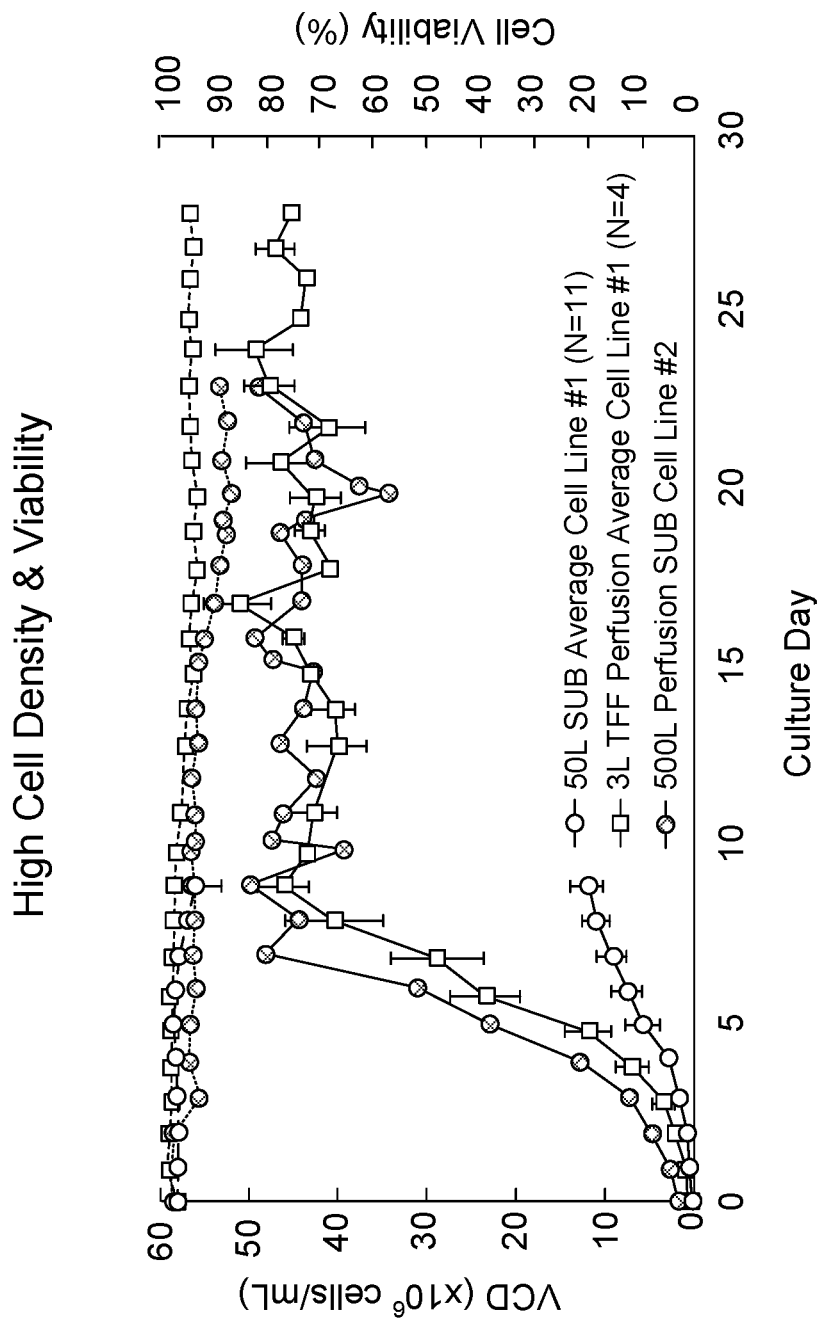
FIGS. 12A and 12B show a comparison of the 50 L single-use bioreactor (SUB), 3 L TFF Perfusion culture, and 500 L Perfusion single-use bioreactor production processes with respect to viable cell density and/or particle titer over the course of a cell culture process.
Figure 12B:
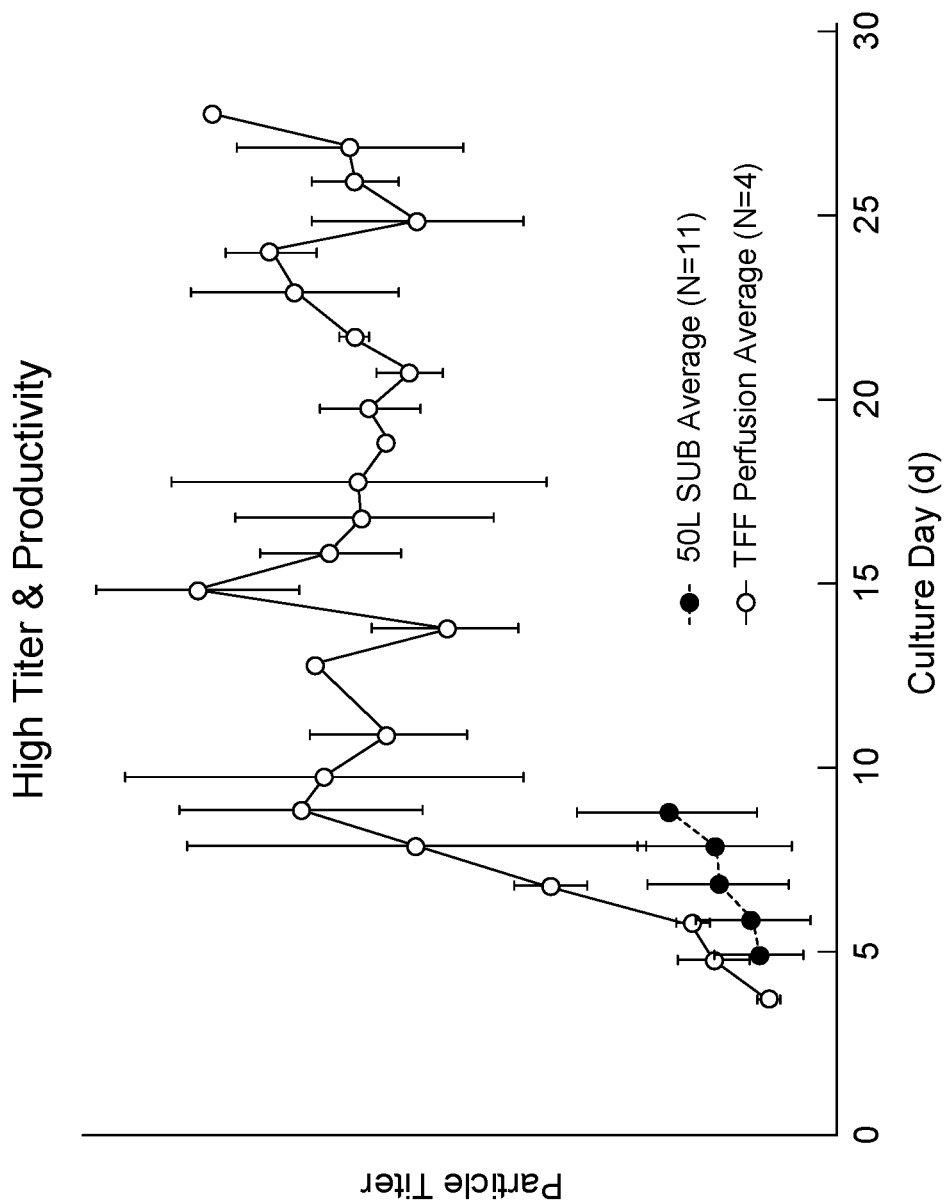

Bioreactor Productivity runs were tested across a range of bioreactors. A 50 L single-use bioreactor, 3 L TFF Perfusion reactor, and 500 L Perfusion single-use bioreactor were used across a production run time of approximately 10-30 days, and the viable cell density (VCD) and particle titer productivity results can be see in FIGS. 12A-12B.

Example 4: Multistep Chromatographic Methods for Preparing EVs with IL-12

Example 4-1: Pretreatment of Samples Comprising EVs

HEK293 cells grown in a perfusion bioreactor were harvested and clarified with depth filtration media. The samples were then treated with Benzonase® (MilliporeSigma) endonuclease to digest nucleic acids. Samples were incubated with Benzonase® and 1 mM or 2 mM $MgCl_2$ for more than 10 hours. The samples can optionally be incubated for longer to allow for additional nuclease digestion, for of a period of about 2-5 days at 15° C. to about 25° C. Upon completion of the Benzonase® digestion samples are further clarified through a series of membrane filters operated in series. Samples are clarified at a feed flux of 50-100 L/m²/hr through a Sartorius Sartopore 2 0.8/0.45 µm membrane filter operated in series with a Sartorius Sartopore 2 XLG 0.8/0.2 µm membrane filter.

Example 4-2: Anion Exchange Chromatography (AEX)

The Benzonase filtrate was purified with an AEX chromatography unit operation in bind-elute mode. For loading, the Benzonase® filtrate was titrated to 550 mM Cl— with 0.05 M Tris, 2M NaCl, pH 7.4. An AEX device containing SARTOBIND® Q membranes (8 mm bed depth) was equilibrated with 500 mM NaCl, 10 mM EDTA, 50 mM Tris, pH 7.4. The column was then challenged with $6.3\times10^{12}$ particles of Benzonase® filtrate per mL of AEX resin with the loading buffer containing a similar pH and conductivity to the equilibration buffer.

Following loading, ten CVs of equilibration buffer were passed over the column prior to elution. Elution buffer consisting of 1200 mM NaCl, 10 mM EDTA, 50 mM Tris, pH 7.4 was applied to the column with approximately 5 CVs of column effluent comprising the AEX elution pool ("AEX pool"). The column was subsequently stripped with 2 M NaCl, 50 mM Tris, pH 7.4 and sanitized with 1 M NaOH, before being stored in 20% ethanol, 150 mM NaCl, 50 mM Tris, pH 7.4.

The AEX step decreased the amount of protein (BCA) impurities from 5584 µg/1×10¹¹ particles in the load to 43 µg/1×10¹¹ particles in the elution pool. No significant clearance of agrin or perlecan was observed. Particle yield (NTA) across this step, a measure of product recovery, was 24%.

Example 4-3: Mixed Mode Chromatography (MMC)

The AEX pool was purified with mixed mode chromatography unit operated in flowthrough mode. Hypercel CMM (Pall), a resin with functional groups supporting CEX and hydrophobic interactions (mixed mode, "MMC"), was packed into a column and operated in series with another column, CaptoCore700, a MMC column. The series of columns were equilibrated with 1 M NaCl, 10 mM EDTA, 50 mM Tris, pH 7.4. The column was then challenged with $1.8\times10^{12}$ particles of AEX pool per mL of MMC resin with the buffer matrix containing a similar pH and conductivity to the equilibration buffer. The flowthrough during the load and a subsequent two CVs of equilibration buffer were collected as the MMC product pool ("MMC pool"). The column was subsequently equilibrated with 1 M NaCl, 50 mM Tris, pH 7.4 and sanitized with 1 M NaOH, before being stored in 20% ethanol, 150 mM NaCl, 50 mM Tris, pH 7.4. As shown in Table 9, the amount of total protein impurity found in the flowthrough after purification was reduced compared the amount contained in the load prior to chromatography, Agrin and DNA impurity amounts remained relatively unchanged. Particle yield (NTA) across this step, a measure of product recovery, was 65%.

TABLE 9

| Protein Impurity | Load (per 1 × 10¹¹ particles) | Flowthrough (per 1 × 10¹¹ particles) |
| --- | --- | --- |
| BCA | 43 µg | 19 µg |
| Agrin | 141 µg | 132 µg |
| DNA (qPCR) | 0.99 ng | 1.08 ng |

Example 4-4: Ultrafiltration/Diafiltration

The MMC pool was then concentrated approximately 10× with a tangential flow filtration (TFF) with a 500 kDa MWCO mPES MicroKros hollow fiber membrane and diafiltered into 5 diavolumes of 0.015 M sodium phosphate dibasic, 0.005 M potassium phosphate monobasic, 49.6 mM sodium chloride, 5% (w/v) sucrose, pH 7.2. In addition to concentration and diafiltration, this TFF step decreased the amount of a protein impurity as summarized below in Table 10. There was not a significant change in normalized BCA concentration. Particle yield (NTA) across this step, a measure of product recovery, was 98%.

TABLE 10

| Protein Impurity | Load (µg/1 × 10¹¹ particles) | Pool (µg/1 × 10¹¹ particles) |
| --- | --- | --- |
| Agrin | 132 | 54 |

Throughout Examples 4-1 through 4-4, 0.22 um or 0.45 µm membrane filtration was employed to reduce bioburden and endotoxin. Membrane filtration steps were included before AEX, MMC, and TFF2 as well as after the TFF. The overall particle yield (NTA) from Benzonase Filtrate® to DSI was 15%.

---

What is claimed is:

1. A method of preparing EVs comprising:
   (i) subjecting a sample comprising the EVs to a depth filtration (depth-filtration processed filtrate sample);
   (ii) contacting the depth-filtration processed filtrate sample to a nuclease (nuclease processed sample);
   iii) contacting the nuclease processed sample to ultrafiltration and/or diafiltration (UF/DF processed filtrate sample);
   (iv) contacting the UF/DF processed filtrate sample with a cation exchange chromatography (CEX) resin (CEX-processed sample);
   (v) contacting the CEX-processed sample with an anion exchange chromatography (AEX) resin (AEX-processed sample);
   (vi) contacting the AEX-processed sample with mixed-mode chromatography (MMC) resin (MMC processed sample); and
   (vii) subjecting the MMC processed sample to a UF/DF.

2. The method of claim 1, wherein the EVs are originated from cells comprising a transgene.

3. The method of claim 2, wherein the transgene encodes a protein comprising an EV protein.

4. The method of claim 3, wherein the EV protein is Prostaglandin F2 Receptor Negative Regulator (PTGFRN), Basigin (BSG), Immunoglobulin superfamily member 3 (IGSF3), Immunoglobulin superfamily member 2 (IGSF2), Integrin beta-1 (ITGB1), Integrin alpha-4 (ITGA4), 4F2 cell-surface antigen heavy chain (SLC3A2), ATP transporter, or BASP1, or a fragment or a modification thereof.

5. The method of claim 4, wherein the EV protein is linked to a biologically active molecule.

6. The method of claim 5, wherein the CEX resin, the AEX resin, and/or the MMC resin comprises a base matrix, wherein the base matrix is a membrane, a monolith, a hydrogel, a porous device, a nanofiber, a composite resin, or a beaded resin.

7. The method of claim 6, wherein the base matrix comprises cellulose, agarose, polystyrene derivatives, polyvinylether, silica, methacrylate derivatives, glass, ceramic hydroxyapatite, or acrylamide.

8. The method of claim 1, wherein the sample is obtained from perfusion cell culture, fed batch cell culture, or batch cell culture.

9. The method of claim 1, further comprising contacting the sample with magnesium and/or EDTA.

10. The method of claim 1, wherein the pH of the CEX loading buffer is lower than the pH of the AEX loading buffer.

* * * * *